US010375956B2

United States Patent
Aspinall et al.

(10) Patent No.: US 10,375,956 B2
(45) Date of Patent: *Aug. 13, 2019

(54) HERBICIDALLY ACTIVE 2-(SUBSTITUTED-PHENYL)-CYCLOPENTANE-1,3-DIONE COMPOUNDS AND DERIVATIVES THEREOF

(71) Applicant: Syngenta Limited, Guilford, Surrey (GB)

(72) Inventors: Ian Henry Aspinall, Bracknell (GB); Stephane Andre Marie Jeanmart, Stein (CH); James Nicholas Scutt, Bracknell (GB); John Benjamin Taylor, Bracknell (GB)

(73) Assignee: Syngenta Limited, Guildford, Surrey (GB)

(*) Notice: Subject to any disclaimer, the term of this patent is extended or adjusted under 35 U.S.C. 154(b) by 509 days.

This patent is subject to a terminal disclaimer.

(21) Appl. No.: 14/896,472

(22) PCT Filed: Jun. 3, 2014

(86) PCT No.: PCT/EP2014/061509
§ 371 (c)(1),
(2) Date: Dec. 7, 2015

(87) PCT Pub. No.: WO2014/195327
PCT Pub. Date: Dec. 11, 2014

(65) Prior Publication Data
US 2016/0128326 A1 May 12, 2016

(30) Foreign Application Priority Data
Jun. 5, 2013 (GB) .................................. 1310047.4

(51) Int. Cl.
| | | |
|---|---|---|
| *A01N 35/06* | (2006.01) | |
| *A01N 37/02* | (2006.01) | |
| *A01N 43/40* | (2006.01) | |
| *A01N 43/54* | (2006.01) | |
| *A01N 43/56* | (2006.01) | |
| *C07C 49/683* | (2006.01) | |
| *C07C 49/747* | (2006.01) | |
| *C07C 49/753* | (2006.01) | |
| *C07C 69/013* | (2006.01) | |
| *C07C 69/157* | (2006.01) | |
| *C07D 213/50* | (2006.01) | |
| *C07D 213/61* | (2006.01) | |
| *C07D 231/16* | (2006.01) | |
| *C07D 239/30* | (2006.01) | |
| *A01N 37/08* | (2006.01) | |

(52) U.S. Cl.
CPC ............ *A01N 35/06* (2013.01); *A01N 37/02* (2013.01); *A01N 37/08* (2013.01); *A01N 43/40* (2013.01); *A01N 43/54* (2013.01); *A01N 43/56* (2013.01); *C07C 49/683* (2013.01); *C07C 49/747* (2013.01); *C07C 49/753* (2013.01); *C07C 69/013* (2013.01); *C07C 69/157* (2013.01); *C07D 213/50* (2013.01); *C07D 213/61* (2013.01); *C07D 231/16* (2013.01); *C07D 239/30* (2013.01); *C07C 2601/10* (2017.05)

(58) Field of Classification Search
None
See application file for complete search history.

(56) References Cited

U.S. PATENT DOCUMENTS 9,107,415 B2 * 8/2015 Avery .................. C07C 49/683

FOREIGN PATENT DOCUMENTS

| WO | 2010000773 A1 | 1/2010 |
|---|---|---|
| WO | 2010069834 A1 | 6/2010 |
| WO | 2011151199 A1 | 12/2011 |
| WO | 2013/079708 A1 | 6/2013 |

OTHER PUBLICATIONS

International search report of International Application No. PCT/EP2014/061509, dated Aug 9, 2014.

* cited by examiner

*Primary Examiner* — Hasan S Ahmed
*Assistant Examiner* — Frank Choi
(74) *Attorney, Agent, or Firm* — Baker & Hostetler LLP; Toni-Junell Herbert

(57) ABSTRACT

The present invention relates to a compound of formula (I): wherein: $R^8$ and $R^9$, independently of each other, are hydrogen, fluorine or $C_1$-$C_3$alkyl; $R^{10}$ is hydrogen or methyl (preferably hydrogen); and the other substituents are as defined herein; and wherein the compound of formula (I) is optionally present as an agrochemically acceptable salt thereof. These compounds are thought to be suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

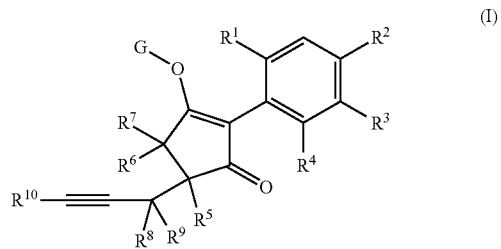

25 Claims, No Drawings

HERBICIDALLY ACTIVE 2-(SUBSTITUTED-PHENYL)-CYCLOPENTANE-1,3-DIONE COMPOUNDS AND DERIVATIVES THEREOF

RELATED APPLICATION INFORMATION

This application is a 371 of International Application No. PCT/EP2014/061509, filed 3 Jul. 2014, which claims priority to Great Britain Application No. 1310047.4, filed 5 Jun. 2013, the contents of which are incorporated herein by reference in their entireties.

The present invention relates to novel, herbicidally active cyclopentanedione compounds, specifically 2-(substituted-phenyl)-cyclopentane-1,3-dione compounds, and derivatives thereof (e.g. enol ketone tautomer derivatives thereof), to processes for their preparation, to herbicidal compositions comprising those compounds, and to their use in controlling weeds such as grassy monocotyledonous weeds, especially in crops of useful plants, or in inhibiting undesired plant growth.

U.S. Pat. No. 4,338,122 (assignee Union Carbide Corp.) discloses 2-aryl-1,3-cyclopentanedione compounds exhibiting acaricidal and herbicidal activity. WO 96/01798 (Bayer AG) and its derived U.S. Pat. No. 5,840,661 disclose 2-aryl-cyclopentane-1,3-dione derivatives and their use as pesticides and herbicides. WO 96/03366 (Bayer AG) and its derived U.S. Pat. No. 5,808,135 disclose fused 2-(2,4,6-trimethylphenyl)cyclopentane-1,3-dione derivatives and their use as pesticides and herbicides.

WO 99/43649 A1 (Bayer AG) discloses inter alia (4-aryl-phenyl)-substituted or (4-heteroaryl-phenyl)-substituted cyclic keto-enols, including several types of cyclic diones and derivatives thereof. WO 99/48869 A1 (Bayer AG) discloses inter alia (3-aryl-phenyl)-substituted or (3-heteroaryl-phenyl)-substituted cyclic keto-enols, including several types of cyclic diones and derivatives thereof.

WO 01/17972 A2 (Syngenta Participations AG) discloses (4-methyl-phenyl)-substituted (such as 4-methyl-2,6-diethyl-phenyl-substituted) heterocycles (e.g. heterocyclic diones) or cyclopentane-1,3-dione derivatives, suitable for use as herbicides. WO 01/74770 (Bayer AG), its equivalent US 2003/0216260 A1, and its derived AU patent 782557 (AU 200144215C) disclose $C_2$-phenyl-substituted cyclic ketoenols and their use as pesticides and herbicides.

WO 03/013249 A1 (Bayer AG) and its equivalent US 2005/0054535 A1 disclose selective herbicidal compositions comprising (a) a (substituted-phenyl)-substituted cyclic ketoenol and (b) a compound which improves crop plant compatibility, in particular cloquintocet-mexyl or mefenpyr-diethyl. In WO 03/013249 A1 and US 2005/0054535 A1, the cyclic ketoenol (whose tautomer is a cyclic dione) can for example be a 2-(substituted-phenyl)-cyclopentane-1,3-dione, or a derivative (e.g. ester or carbonate derivative) thereof.

WO 2007/068427 A2 (Bayer CropScience AG) and its equivalent US 2009/0227563 A1 disclose a composition comprising (a) a (substituted-phenyl)-substituted cyclic ketoenol as a herbicide, and (b) an ammonium and/or phosphonium salt to boost activity. In WO 2007/068427 A2 and US 2009/0227563 A1, the cyclic ketoenol (whose tautomer is a cyclic dione) can for example be a 2-(substituted-phenyl)-cyclopentane-1,3-dione or a derivative (e.g. ester or carbonate derivative) thereof.

WO 2009/019005 A2 (Syngenta Limited) discloses fused bicyclic and oxygen-bridged cyclopentanedione derivatives, specifically 10-oxatricyclo-[5.2.1.0$^{2,6}$]decane-3,5-diones and derivatives, which are substituted by substituted-phenyl and which have herbicidal activity.

WO 2010/000773 A1 (Syngenta Limited) discloses 5-(heterocyclylalkyl)-3-hydroxy-2-phenyl-cyclopent-2-enones and certain derivatives thereof as herbicides.

WO 2010/069834 A1 (Syngenta Participations AG and Syngenta Limited) discloses cyclopentane-1,3-diones having both heteroarylmethyl- and 2-(substituted-phenyl)-substituents on the cyclopentane ring, and derivatives thereof containing latentiating groups; these compounds are disclosed as having herbicidal properties.

WO 2011/007146 A1 (Syngenta Limited) discloses certain 2-(substituted-phenyl)-cyclopentane-1,3-dione derivatives having herbicidal and/or plant-growth-inhibiting properties, in which at the 4-position of the cyclopentane-1,3-dione there is a substituent A-CHR$^4$— in which A is unsubstituted or substituted $C_3$-$C_7$cycloalkyl or A is optionally substituted phenyl.

Other cyclopentane-1,3-dione compounds substituted by substituted-phenyl and having herbicidal activity are described in WO 2010/089210 A1 and WO 2010/102848 A1 (both Syngenta Limited).

WO 2010/102758 A2 (Bayer CropScience AG) discloses (haloalkylmethoxy-)-phenyl-substituted cyclic keto-enols as pest control agents and/or as herbicides.

Copending PCT application PCT/EP2012/074118, filed on 30 Nov. 2012 and published on 6 Jun. 2013 as WO 2013/079672 A1 (Syngenta Limited and Syngenta Participations AG) discloses that certain substituted spiroheterocyclic pyrrolidine dione compounds, having an alkynyl-phenyl-headgroup, have herbicidal properties.

Copending PCT application PCT/EP2012/074172, filed on 30 Nov. 2012 and published on 6 Jun. 2013 as WO 2013/079708 A1 (Syngenta Limited and Syngenta Participations AG) discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl and at the 2-position by (specifically) either methyl or chlorine, and derivatives of the enol ketone tautomer of such cyclopentanediones, which have herbicidal activity and/or plant-growth-inhibiting properties, especially in the control of grassy monocotyledonous weeds and/or when used post-emergence.

2-(Substituted-phenyl)-cyclopentane-1,3-dione compounds, and derivatives of the enol ketone tautomer of such cyclopentane-1,3-diones, which have an alkynyl-methyl- or similar substituent on the cyclopentane-1,3-dione, and which have herbicidal activity and/or plant-growth-inhibiting properties, especially in the control of grassy monocotyledonous weeds and/or when used post-emergence, have now been found, which are encompassed by the present invention.

Some of the exemplified compounds within the following formula (I) according to the present invention are efficacious vs grassy monocotyledonous weeds and appear to be selective for grassy (e.g. warm-climate grassy) monocotyledonous weed control when applied post-emergence in crops of soybean and/or (in some cases) in crops of sugarbeet and/or winter wheat (e.g. see Biological Examples 2 and 3 and the exemplified Compounds hereinafter for details). That is: some of the exemplified compounds according to the invention appear to have a lower post-emergence phytotoxicity on soybean and/or sugarbeet and/or winter wheat than on certain warm-climate grassy monocotyledonous weeds (see e.g. Biological Examples 2 and 3 for details).

Therefore, in a first aspect of the present invention, there is provided a compound of formula (I):

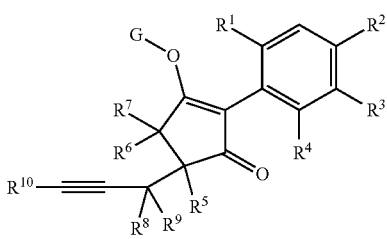

(I)

wherein:
$R^1$ is methyl, ethyl, n-propyl, cyclopropyl, trifluoromethyl, vinyl, ethynyl, fluorine, chlorine, bromine, methoxy, difluoromethoxy or trifluoromethoxy; and
either (a): $R^2$ is $R^{2A}$ and $R^3$ is $R^{3A}$;
or (b): $R^2$ is $R^{2B}$ and $R^3$ is $R^{3B}$;
wherein:
$R^{3A}$ is hydrogen, methyl, fluorine or chlorine; and
$R^{2A}$ is hydrogen, methyl, ethyl, n-propyl, isopropyl, cyclopropyl, $C_1$-$C_2$fluoroalkyl, vinyl, prop-1-enyl, —C≡C—$R^{2AA}$, halogen, or ($C_1$-$C_2$fluoroalkyl)-methoxy-; wherein $R^{2AA}$ is hydrogen, fluorine, trifluoromethyl, ethyl or cyclopropyl;
or $R^{2A}$ is phenyl optionally substituted by 1, 2 or 3 substituents independently being halogen, $C_1$-$C_2$alkyl, $C_1$-$C_2$fluoroalkyl, methoxymethyl, vinyl, ethynyl, $C_1$-$C_3$alkoxy, $C_1$-$C_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
or $R^{2A}$ is monocyclic heteroaryl optionally substituted by 1, 2 or 3 substituents independently being halogen, $C_1$-$C_2$alkyl, $C_1$-$C_2$fluoroalkyl, methoxymethyl, vinyl, ethynyl, $C_1$-$C_3$alkoxy, $C_1$-$C_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
and wherein
$R^{2B}$ is hydrogen, methyl or fluorine; and
either $R^{3B}$ is phenyl optionally substituted by 1, 2 or 3 substituents independently being halogen, $C_1$-$C_2$alkyl, $C_1$-$C_2$fluoroalkyl, methoxymethyl, vinyl, ethynyl, $C_1$-$C_2$alkoxy, $C_1$-$C_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
or $R^{3B}$ is monocyclic heteroaryl optionally substituted by 1, 2 or 3 substituents independently being halogen, $C_1$-$C_2$alkyl, $C_1$-$C_2$fluoroalkyl, methoxymethyl, vinyl, ethynyl, $C_1$-$C_2$alkoxy, $C_1$-$C_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
and wherein
$R^4$ is hydrogen, methyl, ethyl, n-propyl, cyclopropyl, trifluoromethyl, vinyl, ethynyl, fluorine, chlorine, bromine, $C_1$-$C_3$alkoxy, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-; and $R^5$, $R^6$ and $R^7$, independently of each other, are hydrogen, $C_1$-$C_5$alkyl (in particular $C_1$-$C_4$alkyl, e.g. $C_1$-$C_2$alkyl), $C_2$-$C_3$ alkenyl (in particular ethenyl-$CH_2$—), $C_2$-$C_3$alkynyl (in particular ethynyl-$CH_2$—), $C_1$-$C_2$fluoroalkyl or $C_1$-$C_2$alkoxy$C_1$-$C_2$alkyl;
provided that: either (i) at least two of $R^5$, $R^6$ and $R^7$ are hydrogen, or (ii) two of $R^5$, $R^6$ and $R^7$ are methyl and the remaining one of $R^5$, $R^6$ and $R^7$ is hydrogen; and
$R^8$ and $R^9$, independently of each other, are hydrogen, fluorine or $C_1$-$C_3$alkyl; and
$R^{10}$ is hydrogen or methyl;
and wherein:
G is hydrogen; an agriculturally acceptable metal, or an agriculturally acceptable sulfonium or ammonium group; or
G is —C($X^a$)—$R^a$, —C($X^b$)—$X^c$—$R^b$, —C($X^d$)—N($R^c$)—$R^d$, —$SO_2$—$R^e$, —P($X^e$)(R)—$R^g$, —$CH_2$—$X^f$—$R^h$;
or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkyl-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;
wherein $X^a$, $X^b$, $X^c$, $X^d$, $X^e$ and $X^f$ are independently of each other oxygen or sulfur (preferably oxygen); and wherein
$R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{18}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{18}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt (e.g. agriculturally acceptable metal, sulfonium or ammonium salt) thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_5$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine. More preferably, in various aspects and/or embodiments of the invention, halogen is fluorine or chlorine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium.

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine.

Preferred quaternary ammonium bases suitable for salt formation correspond, for example, to the formula [N($R_a R_b R_c R_d$)]OH, wherein $R_a$, $R_b$, $R_c$ and $R_d$ are each independently of the others hydrogen, $C_1$-$C_4$alkyl. Further suitable tetraalkylammonium bases with other anions can be obtained, for example, by anion exchange reactions.

Preferred tertiary sulfonium bases suitable for salt formation correspond, for example, to the formula [S$R_e R_f R_g$]OH, wherein $R_e$, $R_f$ and $R_g$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions.

It should be understood that in those compounds of formula I, where G is a metal, ammonium or sulfonium as mentioned above and as such represents a cation, the corresponding negative charge is largely delocalised across the O—C=C—C=O unit.

The compounds of formula I according to the invention also include hydrates which may be formed during the salt formation.

The latentiating groups (i.e. leaving or removeable groups) within G (for example, without limitation, the latentiating groups where G is —C($X^a$)—$R^a$ or —C($X^b$)—$X^c$—$R^b$, et al.) are generally selected to allow their removal, typically by one or a combination of biochemical, chemical or physical processes, to afford the corresponding compound of formula (I) where G is H, before, during or following (preferably during or following) application of the compound of formula (I) to the treated area (e.g. field) or to plants. Examples of these processes include enzymatic cleavage or other in/on-plant cleavage (e.g. cleavage of ester and/or carbonate moieties), chemical hydrolysis, and/or photolysis. Some compounds bearing such groups G occasionally offer certain advantages or different technical properties, such as improved and/or more consistent and/or different penetration of the cuticula of the plants treated, increased and/or different tolerance of certain crops, improved and/or different compatibility or stability in formulated mixtures containing other herbicides, herbicide safeners, plant growth regulators, fungicides or insecticides, or reduced and/or different leaching properties in soils.

The preferred (including more preferred, most preferred, et al.), suitable and/or particular values of the substituents in, or other features of, the compound of formula (I), in particular (and without limitation): G, $R^1$, $R^2$, $R^{2A}$, $R^{2AA}$, $R^{2B}$, $R^3$, $R^{3A}$, $R^{3B}$, $R^4$, $R^{4A}$, $R^{4B}$, $R^{4C}$, $R^5$, $R^6$, $R^7$, $R^8$, $R^9$, $R^{10}$, $R^{11}$, $R^{11B}$, $R^{12}$, $R^{12A}$, $R^{12AA}$, $R^{12B}$, $R^{13}$, $R^{13A}$, $R^{13AA}$, $R^{13B}$, $R^{14}$, $R^{14A}$, $R^{14B}$, $R^{15}$, $R^{16}$, $R^a$, $R^b$, $R^c$, $R^d$, $R^e$, $R^f$, $R^g$, $R^h$, $X^a$, $X^b$, $X^c$, $X^d$, $X^e$, and/or $X^f$; are set out below (and/or generally herein), and can be either taken alone or taken together with one or more of any other preferred (including more preferred, most preferred, et al.), suitable and/or particular values of the substituents in, or other features of, the compound of formula (I), in any and all possible combination(s) thereof.

Preferably, e.g. in all aspects and/or embodiments of the invention, G is hydrogen; an agriculturally acceptable metal (e.g. an agriculturally acceptable alkali metal or alkaline earth metal), or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined herein. More preferably, G is hydrogen, or an agriculturally acceptable alkali metal (e.g. lithium, sodium or potassium) or an agriculturally acceptable alkaline earth metal (e.g. calcium or magnesium), or —C($X^a$)—$R^a$ or —C($X^b$)—$X^c$—$R^b$.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, $X^a$, $X^b$, $X^c$, $X^d$, $X^e$ and/or $X^f$ are oxygen; and/or $X^c$ is sulfur. More preferably, $X^a$, $X^b$, $X^c$, $X^d$, $X^e$ and $X^f$ are oxygen; and/or $X^c$ is sulfur.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

More preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl, or $C_1$-$C_4$alkoxy$C_1$-$C_4$alkyl.

Preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

More preferably, $R^b$ is $C_1$-$C_{10}$alkyl (e.g. $C_1$-$C_6$alkyl), $C_2$-$C_5$alkenyl-$CH_2$— (e.g. $C_2$-$C_3$alkenyl-$CH_2$—), $C_2$-$C_4$alkenyl-CH(Me)- (e.g. $C_2$-$C_3$alkenyl-CH(Me)-), $C_2$-$C_5$alkynyl-$CH_2$— (e.g. $C_2$-$C_3$alkynyl-$CH_2$—), $C_2$-$C_4$alkynyl-CH(Me)- (e.g. $C_2$-$C_3$alkynyl-CH(Me)-), $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

In a particularly preferable embodiment, G is hydrogen, —C($X^a$)—$R^a$ or —C($X^b$)—$X^c$—$R^b$.

In another preferable embodiment, G is hydrogen, or an agriculturally acceptable alkali metal or alkaline earth metal, or an agriculturally acceptable sulfonium or ammonium group. In a particular embodiment, G is hydrogen, or an agriculturally acceptable alkali metal (e.g. lithium, sodium or potassium) or an agriculturally acceptable alkaline earth metal (e.g. calcium or magnesium).

Most preferably, G is hydrogen.

Preferably, e.g. in all aspects and/or embodiments of the invention, $R^1$ is methyl, ethyl, cyclopropyl, ethynyl, fluorine, chlorine, bromine, methoxy, difluoromethoxy or trifluoromethoxy.

Preferably, e.g. in all aspects and/or embodiments of the invention, $R^1$ is methyl, ethyl, ethynyl, fluorine, chlorine, bromine, methoxy, difluoromethoxy or trifluoromethoxy.

More preferably, e.g. in all aspects and/or embodiments of the invention, $R^1$ is methyl, fluorine, chlorine, bromine, difluoromethoxy or trifluoromethoxy.

Even more preferably, $R^1$ is methyl, fluorine, chlorine or bromine.

Still more preferably, $R^1$ is methyl, fluorine or chlorine.

Most preferably, e.g. in all aspects and/or embodiments of the invention, $R^1$ is fluorine or chlorine.

In the invention, either (a): $R^2$ is $R^{2A}$ and $R^3$ is $R^{3A}$; or (b): $R^2$ is $R^{2B}$ and $R^3$ is $R^{3B}$.

Most preferably, e.g. in all aspects and/or embodiments of the invention, $R^2$ is $R^{2A}$ and $R^3$ is $R^{3A}$.

Preferably, e.g. in all aspects and/or embodiments of the invention, $R^{3A}$ is hydrogen or methyl.

Most preferably, e.g. in all aspects and/or embodiments of the invention, $R^{3A}$ is hydrogen.

When $R^{2A}$ is halogen, then preferably it is chlorine or bromine.

When $R^{2A}$ is ($C_1$-$C_2$fluoroalkyl)-methoxy-, then preferably it is $C_1$fluoroalkyl-methoxy-, such as $CF_3CH_2O$ or $CHF_2CH_2O$.

$R^{2A}$ can be —C≡C—$R^{2AA}$. Preferably, $R^{2AA}$ is hydrogen, fluorine or trifluoromethyl. More preferably, $R^{2AA}$ is hydrogen.

Preferably, e.g. in all aspects and/or embodiments of the invention, $R^{2A}$ is hydrogen, methyl, ethyl, vinyl, prop-1-enyl, —C≡C—$R^{2AA}$ (in particular, —C≡C—$R^{2AA}$ wherein $R^{2AA}$ is hydrogen), halogen (in particular chlorine or bromine), or $C_1$fluoroalkyl-methoxy- (in particular, $CF_3CH_2O$ or $CHF_2CH_2O$);

or $R^{2A}$ is phenyl optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro;

or $R^{2A}$ is monocyclic 6-membered or 5-membered heteroaryl (e.g. pyridin-2-yl, pyridin-3-yl, pyrimidin-2-yl, pyrimidin-5-yl, pyridazin-3-yl, or pyrazol-1-yl) optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro.

Preferably, e.g. in all aspects and/or embodiments of the invention, $R^{2A}$ is methyl, ethyl, vinyl, prop-1-enyl, —C≡C—$R^{2AA}$ (in particular, —C≡C—$R^{2AA}$ wherein $R^{2AA}$ is hydrogen), halogen (in particular chlorine or bromine), or $C_1$fluoroalkyl-methoxy- (in particular, $CF_3CH_2O$ or $CHF_2CH_2O$);

or $R^{2A}$ is phenyl optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro;

or $R^{2A}$ is monocyclic 6-membered or 5-membered heteroaryl (e.g. pyridin-2-yl, pyridin-3-yl, pyrimidin-2-yl, pyrimidin-5-yl, pyridazin-3-yl, or pyrazol-1-yl) optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro.

More preferably, e.g. in all aspects and/or embodiments of the invention, $R^{2A}$ is methyl, —C≡C—$R^{2AA}$ (in particular, —C≡C—$R^{2AA}$ wherein $R^{2AA}$ is hydrogen), chlorine or bromine;

or $R^{2A}$ is phenyl optionally substituted by 1, 2 or 3 (preferably 1 or 2) substituents independently being halogen (in particular fluorine, chlorine or bromine, more particularly fluorine or chlorine), $C_1$fluoroalkyl, $C_1$fluoroalkoxy or cyano;

or $R^{2A}$ is monocyclic 6-membered or 5-membered heteroaryl (e.g. pyridin-2-yl, pyridin-3-yl, pyrimidin-2-yl, pyrimidin-5-yl, pyridazin-3-yl, or pyrazol-1-yl) optionally substituted by 1, 2 or 3 (preferably 1 or 2) substituents independently being halogen (in particular fluorine, chlorine or bromine, more particularly fluorine or chlorine), $C_1$fluoroalkyl, $C_1$fluoroalkoxy or cyano.

Still more preferably, e.g. in all aspects and/or embodiments of the invention, $R^{2A}$ is methyl or —C≡C—$R^{2AA}$ wherein $R^{2AA}$ is hydrogen;

or $R^{2A}$ is phenyl substituted by 1, 2 or 3 (preferably 1 or 2) substituents independently being fluorine, chlorine or bromine (preferably independently being fluorine or chlorine);

or $R^{2A}$ is monocyclic 6-membered or 5-membered heteroaryl (e.g. pyridin-2-yl, pyridin-3-yl, pyrimidin-2-yl, pyrimidin-5-yl, pyridazin-3-yl, or pyrazol-1-yl) substituted by 1, 2 or 3 (preferably 1 or 2) substituents independently being fluorine, chlorine or bromine (preferably independently being fluorine or chlorine).

Preferably, e.g. in all aspects and/or embodiments of the invention, when $R^{2A}$ is optionally substituted phenyl, then $R^{2A}$ is of sub-formula (a) or (a1):

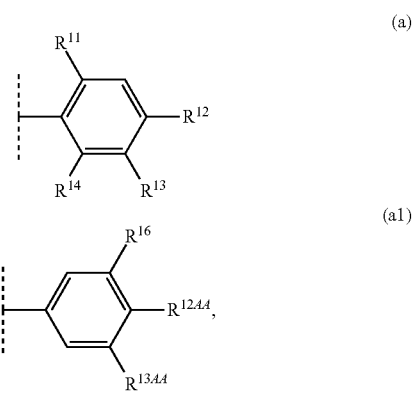

in which:

$R^{11}$ is hydrogen, fluorine or chlorine;

$R^{12}$ is halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;

$R^{13}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro; and $R^{14}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro; provided that one or more (preferably two or more) of $R^{11}$, $R^{13}$ and $R^{14}$ are hydrogen; and provided that either one or none (i.e. no more than one) of $R^{12}$, $R^{13}$ and $R^{14}$ are $C_1$-$C_2$alkyl, $C_1$-$C_2$alkoxy or nitro; and $R^{12AA}$ is hydrogen, fluorine or chlorine (in particular hydrogen or fluorine);

$R^{13AA}$ is fluorine or chlorine (in particular fluorine); and $R^{16}$ is hydrogen, fluorine or chlorine (in particular hydrogen or fluorine);

provided that when $R^{12AA}$ is fluorine or chlorine, then $R^{16}$ is fluorine or chlorine; and provided that either one or none (i.e. no more than one) of $R^{13AA}$ and $R^{16}$ are chlorine.

More preferably, when $R^{2A}$ is optionally substituted phenyl, then $R^{2A}$ is of sub-formula (a). $R^{2A}$ being of sub-formula (a1) is less preferred than sub-formula (a).

In the above-mentioned preferred or more preferred embodiment wherein $R^{2A}$ is of sub-formula (a), preferably, two or more of $R^{11}$, $R^{13}$ and $R^{14}$ are hydrogen.

Most preferably, $R^{11}$ is hydrogen.

Preferably, $R^{12}$ is halogen (in particular fluorine, chlorine or bromine) or $C_1$fluoroalkyl (e.g. trifluoromethyl), $C_1$fluoroalkoxy (e.g. difluoromethoxy or trifluoromethoxy), or cyano. More preferably, $R^{12}$ is halogen; even more preferably fluorine, chlorine or bromine.

Most preferably, $R^{12}$ is fluorine or chlorine.

Preferably, $R^{13}$ is hydrogen, fluorine or chlorine; more preferably hydrogen or fluorine.

Most preferably, $R^{13}$ is hydrogen.

Preferably, $R^{14}$ is hydrogen, halogen (in particular fluorine, chlorine or bromine, more particularly fluorine or chlorine), or $C_1$fluoroalkyl (e.g. trifluoromethyl).

More preferably, $R^{14}$ is hydrogen or halogen; even more preferably hydrogen, fluorine, chlorine or bromine.

Most preferably, $R^{14}$ is hydrogen, fluorine or chlorine; in particular hydrogen or fluorine.

For the above preferred $R^{11}$, $R^{12}$, $R^{13}$ and/or $R^{14}$ features, then, e.g. as previously mentioned: one or more (preferably two or more) of $R^{11}$, $R^{13}$ and $R^{14}$ are hydrogen; and either one or none (i.e. no more than one) of $R^{12}$, $R^{13}$ and $R^{14}$ are $C_1$-$C_2$alkyl, $C_1$-$C_2$alkoxy or nitro.

Preferably, e.g. in all aspects and/or embodiments of the invention, when $R^{2A}$ is optionally substituted monocyclic heteroaryl (e.g. monocyclic 6-membered or 5-membered heteroaryl, in particular pyridin-2-yl, pyridin-3-yl, pyrimidin-2-yl, pyrimidin-5-yl, pyridazin-3-yl, or pyrazol-1-yl)), then $R^{2A}$ is of sub-formula (b), (c), (d), (e), (f) or (g):

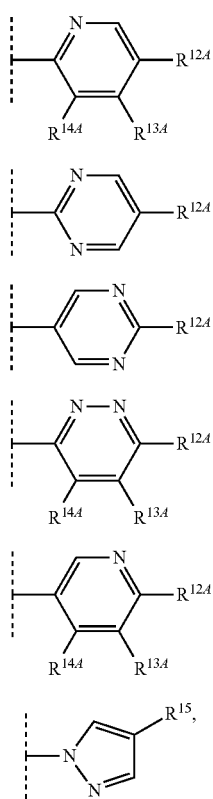

in which:

$R^{12A}$ is halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;

$R^{13A}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro; and $R^{14A}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;

provided that either one or none (i.e. no more than one) of $R^{12A}$, $R^{13A}$ and $R^{14A}$ are $C_1$-$C_2$alkyl, $C_1$-$C_2$alkoxy or nitro;

and $R^{15}$ is hydrogen, halogen (in particular fluorine, chlorine or bromine, more particularly fluorine or chlorine), methyl, $C_1$fluoroalkyl (e.g. trifluoromethyl), $C_1$fluoroalkoxy (e.g. difluoromethoxy or trifluoromethoxy), or cyano.

In the above-mentioned preferred embodiments wherein $R^{2A}$ is of sub-formula (b), (e) or (f), preferably, one or both of $R^{13A}$ and $R^{14A}$ are hydrogen.

Preferably, $R^{12A}$ is halogen (in particular fluorine, chlorine or bromine) or $C_1$fluoroalkyl (e.g. trifluoromethyl), $C_1$fluoroalkoxy (e.g. difluoromethoxy or trifluoromethoxy), or cyano. More preferably, $R^{12A}$ is halogen; even more preferably fluorine, chlorine or bromine.

Most preferably, $R^{12A}$ is fluorine or chlorine; in particular chlorine.

Preferably, $R^{13A}$ is hydrogen, fluorine or chlorine; more preferably hydrogen or fluorine.

Most preferably, $R^{13A}$ is hydrogen.

Preferably, $R^{14A}$ is hydrogen, halogen (in particular fluorine, chlorine or bromine, more particularly fluorine or chlorine), or $C_1$fluoroalkyl (e.g. trifluoromethyl).

More preferably, $R^{14A}$ is hydrogen or halogen; even more preferably hydrogen, fluorine, chlorine or bromine.

Most preferably, $R^{14A}$ is hydrogen, fluorine or chlorine; in particular hydrogen or fluorine.

For the above preferred $R^{12A}$, $R^{13A}$ and/or $R^{14A}$ features, then, e.g. as previously mentioned: either one or none (i.e. no more than one), more preferably none, of $R^{12A}$, $R^{13A}$ and $R^{14A}$ are $C_1$-$C_2$alkyl, $C_1$-$C_2$alkoxy or nitro.

Preferably, $R^{15}$ is hydrogen, fluorine, chlorine, methyl, $C_1$fluoroalkyl (e.g. trifluoromethyl), or $C_1$fluoroalkoxy (e.g. difluoromethoxy or trifluoromethoxy).

Most preferably $R^{15}$ is fluorine or chlorine, in particular chlorine.

More preferably, e.g. in all aspects and/or embodiments of the invention, when $R^{2A}$ is optionally substituted monocyclic heteroaryl (e.g. monocyclic 6-membered or 5-membered heteroaryl, in particular optionally substituted pyridin-2-yl, pyrimidin-2-yl, or pyrazol-1-yl)), then $R^{2A}$ is of sub-formula (b), (c) or (g), in particular (b) or (c), as defined herein.

Most preferably, e.g. in all aspects and/or embodiments of the invention, $R^{2A}$ is of sub-formula (a), (b), (c) or (g), in particular of sub-formula (a), (b) or (c), as defined herein. Most preferably, in this embodiment, $R^2$ is $R^{2A}$ and $R^3$ is $R^{3A}$.

In another particular embodiment (b) of the invention, $R^2$ is $R^{2B}$ and $R^3$ is $R^{3B}$.

Preferably, e.g. in all aspects and/or embodiments of the invention, $R^{2B}$ is hydrogen or methyl.

Most preferably, e.g. in all aspects and/or embodiments of the invention, $R^{2B}$ is hydrogen.

Preferably, e.g. in all aspects and/or embodiments of the invention, either $R^{3B}$ is phenyl optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro;

or $R^{3B}$ is monocyclic 6-membered heteroaryl (e.g. pyridin-2-yl, or pyrimidin-2-yl) optionally substituted by 1, 2 or 3 (preferably 1 or 2) substituents independently being halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro.

More preferably, e.g. in all aspects and/or embodiments of the invention, either $R^{3B}$ is phenyl optionally substituted by 1, 2 or 3 (preferably 1 or 2) substituents independently being halogen (in particular fluorine, chlorine or bromine, more particularly fluorine or chlorine), methyl, $C_1$fluoroalkyl, methoxy, $C_1$fluoroalkoxy or cyano, provided that either one or none (i.e. no more than one) of these optional substituents are methyl or methoxy;

or $R^{3B}$ is monocyclic 6-membered heteroaryl (e.g. pyridin-2-yl, or pyrimidin-2-yl) optionally substituted by 1, 2 or 3 (preferably 1 or 2) substituents independently being halogen (in particular fluorine, chlorine or bromine, more particularly fluorine or chlorine), methyl, $C_1$fluoroalkyl, methoxy, $C_1$fluoroalkoxy or cyano, provided that either one or none (i.e. no more than one) of these optional substituents are methyl or methoxy.

Still more preferably, e.g. in all aspects and/or embodiments of the invention, either $R^{3B}$ is phenyl substituted by 1, 2 or 3 (preferably 1 or 2) substituents independently being fluorine, chlorine or bromine (preferably independently being fluorine or chlorine);

or $R^{3B}$ is monocyclic 6-membered heteroaryl (e.g. pyridin-2-yl or pyrimidin-2-yl) substituted by 1, 2 or 3 (preferably 1 or 2) substituents independently being fluorine, chlorine or bromine (preferably independently being fluorine or chlorine).

Preferably, e.g. in all aspects and/or embodiments of the invention, when $R^{3B}$ is optionally

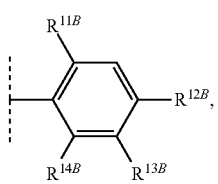
(a2)

substituted phenyl, then $R^{3B}$ is of sub-formula (a2):
in which
$R^{11B}$ is hydrogen, fluorine, chlorine, methyl, $C_1$fluoroalkyl, methoxy or $C_1$fluoroalkoxy;
$R^{12B}$ is halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;
$R^{13B}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro; and
$R^{14B}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;

provided that one or more (preferably two or more) of $R^{11B}$, $R^{13B}$ and $R^{14B}$ are hydrogen; and provided that either one or none (i.e. no more than one) of $R^{12B}$, $R^{13B}$ and $R^{14B}$ are $C_1$-$C_2$alkyl, $C_1$-$C_2$alkoxy or nitro.

Preferably, $R^{11B}$ is hydrogen, fluorine, chlorine, methyl or methoxy; most preferably hydrogen, fluorine or chlorine.

Preferably, $R^{12B}$ is fluorine, chlorine, $C_1$fluoroalkyl, methoxy or $C_1$fluoroalkoxy; more preferably fluorine or chlorine; most preferably chlorine.

Preferably, $R^{13B}$ is hydrogen or fluorine; most preferably hydrogen.

Preferably, $R^{14B}$ is hydrogen or fluorine; most preferably hydrogen.

Preferably, e.g. in all aspects and/or embodiments of the invention, when $R^{3B}$ is optionally substituted monocyclic heteroaryl (e.g. monocyclic 6-membered heteroaryl, in particular pyridin-2-yl or pyrimidin-2-yl), then $R^{3B}$ is of sub-formula (b1) or (c1):

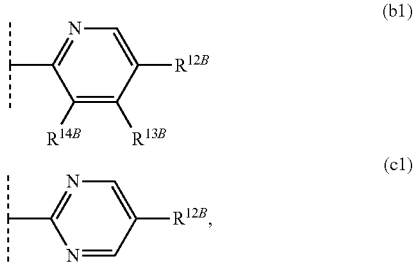

in which:
$R^{12B}$ is halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;
$R^{13B}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro; and
$R^{14B}$ is hydrogen, halogen (in particular fluorine, chlorine or bromine, more particularly fluorine or chlorine), $C_1$-$C_2$alkyl, $C_1$-$C_2$fluoroalkyl, $C_1$-$C_2$alkoxy, $C_1$-$C_2$fluoroalkoxy, cyano or nitro;
provided that either one or none (i.e. no more than one) of $R^{12B}$, $R^{13B}$ and $R^{14B}$ are $C_1$-$C_2$alkyl, $C_1$-$C_2$alkoxy or nitro.

Preferably, in sub-formula (b1) or (c1), $R^{12B}$ is fluorine, chlorine, $C_1$fluoroalkyl, methoxy or $C_1$fluoroalkoxy; more preferably fluorine or chlorine; most preferably chlorine. Preferably, in sub-formula (b1) or (c1), $R^{13B}$ is hydrogen or fluorine; most preferably hydrogen. Preferably, in sub-formula (b1) or (c1), $R^{14B}$ is hydrogen, fluorine or chlorine; most preferably hydrogen or fluorine.

More preferably, e.g. in all aspects and/or embodiments of the invention, $R^{3B}$ is optionally substituted phenyl. In this embodiment, then, even more preferably, $R^{3B}$ is of sub-formula (a2):

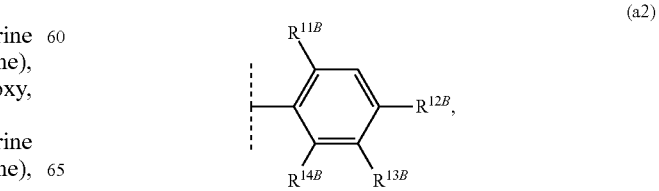

in which $R^{11B}$, $R^{12B}$, $R^{13B}$ and $R^{14B}$ are as defined herein.

In the invention, $R^4$ is hydrogen, methyl, ethyl, n-propyl, cyclopropyl, trifluoromethyl, vinyl, ethynyl, fluorine, chlorine, bromine, $C_1$-$C_3$alkoxy (e.g. methoxy, ethoxy, n-propoxy or isopropoxy), $C_1$-$C_2$fluoroalkoxy (e.g. monofluoromethoxy, difluoromethoxy or trifluoromethoxy; or more particularly $C_1$fluoroalkyl-methoxy- such as trifluoromethyl-methoxy- or difluoromethyl-methoxy-), $C_1$-$C_2$alkoxy-$C_1$-$C_3$alkoxy-, or $C_1$fluoroalkoxy-$C_1$-$C_3$alkoxy-.

Preferences for $R^4$ follow. Most of the following $R^4$ preferences are particularly preferred and/or particularly applicable when $R^2$ is $R^{2A}$ and $R^3$ is $R^{3A}$ (which is particularly preferred).

Preferably, when $R^4$ is $C_1$-$C_2$alkoxy-$C_1$-$C_3$alkoxy- or $C_1$fluoroalkoxy-$C_1$-$C_3$alkoxy-, then $R^4$ is $R^{4A}$O—CH($R^{4B}$)—CH($R^{4C}$)—O—;

wherein $R^{4A}$ is $C_1$-$C_2$alkyl (in particular methyl) or $C_1$fluoroalkyl (such as trifluoromethyl); and $R^{4B}$ and $R^{4C}$ are independently hydrogen or methyl, provided that one or both of $R^{4B}$ and $R^{4C}$ are hydrogen.

Preferably, $R^{4A}$ is methyl or $C_1$fluoroalkyl, more preferably methyl.

Preferably, both of $R^{4B}$ and $R^{4C}$ are hydrogen.

More preferably, when $R^4$ is $C_1$-$C_2$alkoxy-$C_1$-$C_3$alkoxy- or $C_1$fluoroalkoxy-$C_1$-$C_3$alkoxy- (in particular when $R^4$ is $R^{4A}$O—CH($R^{4B}$)—CH($R^{4C}$)—O—), then $R^4$ is MeO—CH$_2$—CH$_2$—O—.

Preferably, e.g. in all aspects and/or embodiments of the invention, $R^4$ is hydrogen, methyl, ethyl, n-propyl, cyclopropyl, vinyl, ethynyl, fluorine, chlorine, bromine, methoxy, ethoxy, n-propoxy, $C_1$-$C_2$fluoroalkoxy (e.g. monofluoromethoxy, difluoromethoxy or trifluoromethoxy; or more particularly $C_1$fluoroalkyl-methoxy- such as trifluoromethyl-methoxy- or difluoromethyl-methoxy-), or $R^{4A}$O—CH($R^{4B}$)—CH($R^{4C}$)—O— (in particular MeO—CH$_2$—CH$_2$—O—).

Preferably, e.g. in all aspects and/or embodiments of the invention, $R^4$ is methyl, ethyl, n-propyl, cyclopropyl, vinyl, ethynyl, fluorine, chlorine, bromine, methoxy, ethoxy, n-propoxy, $C_1$-$C_2$fluoroalkoxy (e.g. monofluoromethoxy, difluoromethoxy or trifluoromethoxy; or more particularly $C_1$fluoroalkyl-methoxy- such as trifluoromethyl-methoxy- or difluoromethyl-methoxy-), or $R^{4A}$O—CH($R^{4B}$)—CH($R^{4C}$)—O— (in particular MeO—CH$_2$—CH$_2$—O—).

Alternatively or additionally, preferably, e.g. in all aspects and/or embodiments of the invention, $R^4$ is hydrogen, methyl, ethyl, ethynyl, chlorine, methoxy, ethoxy, n-propoxy, $C_1$-$C_2$fluoroalkoxy (e.g. monofluoromethoxy, difluoromethoxy or trifluoromethoxy; or more particularly $C_1$fluoroalkyl-methoxy- such as trifluoromethyl-methoxy- or difluoromethyl-methoxy-), or $R^{4A}$O—CH($R^{4B}$)—CH($R^{4C}$)—O— (in particular MeO—CH$_2$—CH$_2$—O—).

More preferably, $R^4$ is not hydrogen. This is especially preferred when $R^2$ is $R^{2A}$ and $R^3$ is $R^{3A}$ (which is preferred).

More preferably, e.g. in all aspects and/or embodiments of the invention, $R^4$ is methyl, ethyl, ethynyl, fluorine, chlorine, methoxy, ethoxy, n-propoxy, $C_1$-$C_2$fluoroalkoxy (e.g. monofluoromethoxy, difluoromethoxy or trifluoromethoxy; or more particularly $C_1$fluoroalkyl-methoxy- such as trifluoromethyl-methoxy- or difluoromethyl-methoxy-), or MeO—CH$_2$—CH$_2$—O—.

Even more preferably, e.g. in all aspects and/or embodiments of the invention, $R^4$ is methyl, fluorine, chlorine, methoxy, ethoxy, $C_1$fluoroalkyl-methoxy- (in particular trifluoromethyl-methoxy- or difluoromethyl-methoxy-), or MeO—CH$_2$—CH$_2$—O—.

Still more preferably, e.g. in all aspects and/or embodiments of the invention, $R^4$ is methyl, chlorine or methoxy.

Yet more preferably, e.g. in all aspects and/or embodiments of the invention, $R^4$ is methyl or methoxy.

Most preferably, e.g. in all aspects and/or embodiments of the invention, $R^4$ is methoxy.

Preferences for $R^4$, which are particularly preferred and/or particularly applicable when $R^2$ is $R^{2B}$ and $R^3$ is $R^{3B}$ (which is less preferred), follow. In this embodiment, preferably, $R^4$ is hydrogen, methyl, fluorine or chlorine, in particular hydrogen, methyl or fluorine. In this embodiment, most preferably, $R^4$ is hydrogen.

Particularly preferably, e.g. in all aspects and/or embodiments of the invention:

$R^1$ is methyl, fluorine, chlorine, bromine, difluoromethoxy or trifluoromethoxy (or more preferably, $R^1$ is methyl, fluorine, chlorine or bromine; or even more preferably, $R^1$ is methyl, fluorine or chlorine); and either (a): $R^2$ is $R^{2A}$ and $R^3$ is $R^{3A}$;

or (b): $R^2$ is $R^{2B}$ and $R^3$ is $R^{3B}$;

and wherein:

$R^{3A}$ is hydrogen or methyl (or more preferably, $R^{3A}$ is hydrogen); and $R^{2A}$ is methyl, —C≡C—$R^{2AA}$ (in particular, —C≡C—$R^{2AA}$ wherein $R^{2AA}$ is hydrogen), chlorine or bromine (or more preferably, $R^{2A}$ is methyl or —C≡C—$R^{2AA}$ wherein $R^{2AA}$ is hydrogen); or $R^{2A}$ is of sub-formula (a) or (a1) as defined herein e.g. hereinabove (more preferably with the preferences as defined herein e.g. hereinabove);

or $R^{2A}$ is of sub-formula (b), (c), (d), (e), (f) or (g) as defined herein e.g. hereinabove (more preferably with the preferences as defined herein e.g. hereinabove);

(or, even more preferably, $R^{2A}$ is of sub-formula (a), (b), (c) or (g), still more preferably of sub-formula (a), (b) or (c), as defined herein e.g. hereinabove, in particular with the preferences as defined herein e.g. hereinabove);

and $R^{2B}$ is hydrogen or methyl (or more preferably, $R^{2B}$ is hydrogen); and either $R^{3B}$ is of sub-formula (a2) as defined herein e.g. hereinabove (more preferably with the preferences as defined herein e.g. hereinabove);

or $R^{3B}$ is of sub-formula (b1) or (c1) as defined herein e.g. hereinabove (more preferably with the preferences as defined herein e.g. hereinabove);

(or, even more preferably, $R^{3B}$ is of sub-formula (a2) as defined herein e.g. hereinabove, in particular with the preferences as defined herein e.g. hereinabove);

and wherein:

when $R^2$ is $R^{2A}$ and $R^3$ is $R^{3A}$ (which is particularly preferred), then $R^4$ is methyl, ethyl, ethynyl, fluorine, chlorine, methoxy, ethoxy, n-propoxy, $C_1$-$C_2$fluoroalkoxy (e.g. monofluoromethoxy, difluoromethoxy or trifluoromethoxy; or more particularly $C_1$fluoroalkyl-methoxy- such as trifluoromethyl-methoxy- or difluoromethyl-methoxy-), or MeO—CH$_2$—CH$_2$—O—;

(or, more preferably, when $R^2$ is $R^{2A}$ and $R^3$ is $R^{3A}$ (which is particularly preferred), then $R^4$ is methyl, fluorine, chlorine, methoxy, ethoxy, $C_1$fluoroalkyl-methoxy- (in particular trifluoromethyl-methoxy- or difluoromethyl-methoxy-), or MeO—CH$_2$—CH$_2$—O—;

or, even more preferably, when $R^2$ is $R^{2A}$ and $R^3$ is $R^{3A}$ (which is particularly preferred), then $R^4$ is methyl, chlorine or methoxy);

and, when $R^2$ is $R^{2B}$ and $R^3$ is $R^{3B}$ (which is less preferred), then $R^4$ is hydrogen, methyl, fluorine or chlorine, in particular hydrogen, methyl or fluorine (or more preferably, when $R^2$ is $R^{2B}$ and $R^3$ is $R^{3B}$, then $R^4$ is hydrogen).

As discussed before, most preferably, e.g. in all aspects and/or embodiments of the invention, $R^2$ is $R^{2A}$ and $R^3$ is $R^{3A}$.

In the invention, $R^5$, $R^6$ and $R^7$, independently of each other, are hydrogen, $C_1$-$C_5$alkyl (in particular $C_1$-$C_4$alkyl, e.g. $C_1$-$C_2$alkyl), $C_2$-$C_3$ alkenyl (in particular ethenyl-$CH_2$—), $C_2$-$C_3$alkynyl (in particular ethynyl-$CH_2$—), $C_1$-$C_2$fluoroalkyl or $C_1$-$C_2$alkoxy$C_1$-$C_2$alkyl (in particular methoxymethyl);

provided that: either (i) at least two of $R^5$, $R^6$ and $R^7$ are hydrogen, or (ii) two of $R^5$, $R^6$ and $R^7$ are methyl and the remaining one of $R^5$, $R^6$ and $R^7$ is hydrogen.

Preferably, e.g. in all aspects and/or embodiments of the invention, $R^5$, $R^6$ and $R^7$, independently of each other, are hydrogen, $C_1$-$C_2$alkyl, ethynyl-$CH_2$—, $C_1$fluoroalkyl or methoxymethyl;

provided that: either (i) at least two of $R^5$, $R^6$ and $R^7$ are hydrogen, or (ii) two of $R^5$, $R^6$ and $R^7$ are methyl and the remaining one of $R^5$, $R^6$ and $R^7$ is hydrogen.

More preferably, e.g. in all aspects and/or embodiments of the invention, $R^5$, $R^6$ and $R^7$, independently of each other, are hydrogen or methyl;

provided that: either (i) at least two of $R^5$, $R^6$ and $R^7$ are hydrogen, or (ii) two of $R^5$, $R^6$ and $R^7$ are methyl and the remaining one of $R^5$, $R^6$ and $R^7$ is hydrogen.

Most preferably, e.g. in all aspects and/or embodiments of the invention, all of $R^5$, $R^6$ and $R^7$ are hydrogen.

Preferably, e.g. in all aspects and/or embodiments of the invention, $R^8$ and $R^9$, independently of each other, are hydrogen or methyl.

Most preferably, e.g. in all aspects and/or embodiments of the invention, $R^8$ and $R^9$ are both hydrogen.

Most preferably, e.g. in all aspects and/or embodiments of the invention, $R^{10}$ is hydrogen.

In a more particularly preferable embodiment of the invention (which e.g. can apply to all aspects and/or embodiments of the invention), the compound of formula (I) is any of (e.g. any one of) compounds A1 to A29 or A30 to A41, as described and/or illustrated herein, present either as a free compound (i.e. a compound not substantially in the form of a salt) and/or (e.g. where chemically possible) present as an agrochemically acceptable salt (e.g. agriculturally acceptable metal, sulfonium or ammonium salt) thereof. Alternatively, in an also more particularly preferable embodiment of the invention (which e.g. can apply to all aspects and/or embodiments of the invention), the compound of formula (I) is any of (e.g. any one of) compounds A42 or A45, as described and/or illustrated herein, present either as a free compound (i.e. a compound not substantially in the form of a salt) and/or (e.g. where chemically possible) present as an agrochemically acceptable salt (e.g. agriculturally acceptable metal, sulfonium or ammonium salt) thereof.

In another preferable embodiment of the invention (which e.g. can apply to all aspects and/or embodiments of the invention), the compound of formula (I) is any of (e.g. any one of) the compounds disclosed in any of Tables 1 to 60, as described and/or illustrated herein, present either as a free compound (i.e. a compound not substantially in the form of a salt) and/or (e.g. where chemically possible) present as an agrochemically acceptable salt (e.g. agriculturally acceptable metal, sulfonium or ammonium salt) thereof.

In all embodiments or aspects of the invention, it is preferred that the compound of formula (I) is a compound of formula (IC):

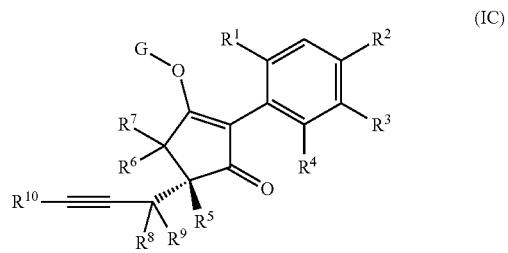

(IC)

wherein $R^1$, $R^2$, $R^3$, $R^4$, $R^5$, $R^6$, $R^7$, $R^8$, $R^9$, $R^{10}$, and G are as defined herein, and wherein 40% or more (in particular 45% or more) by molarity of the compound of formula (IC) has the indicated stereochemistry at the ring-carbon atom bonded to $R^5$ and —$CR^8R^9$—C≡C—$R^{10}$. For example, this broadest definition of formula (IC) includes compounds which are substantially racemic at the ring-carbon atom bonded to $R^5$ and —$CR^8R^9$—C≡C—$R^{10}$, and also includes compounds enriched with isomer(s) having the stereochemistry indicated at the ring-carbon atom bonded to $R^5$ and —$CR^8R^9$—C≡C—$R^{10}$.

More preferably, more than 50% (still more preferably more than 70% or more than 80%, most preferably more than 90% or more than 95%) by molarity of the compound of formula (IC) has the indicated stereochemistry at the ring-carbon atom bonded to $R^5$ and —$CR^8R^9$—C≡C—$R^{10}$. This more preferred definition of formula (IC) includes compounds enriched with isomer(s) having the stereochemistry indicated at the ring-carbon atom bonded to $R^5$ and —$CR^8R^9$—C≡C—$R^{10}$.

Depending on the nature of the substituents G, $R^1$, $R^2$, $R^3$, $R^4$, $R^5$, $R^6$, $R^7$, $R^8$, $R^9$, and $R^{10}$, compounds of formula (I) may exist in different isomeric or tautomeric forms.

For example, when G is hydrogen, compounds of formula (I) may exist in different tautomeric forms (of formulae (A), (A1) and (A2)), as shown below:

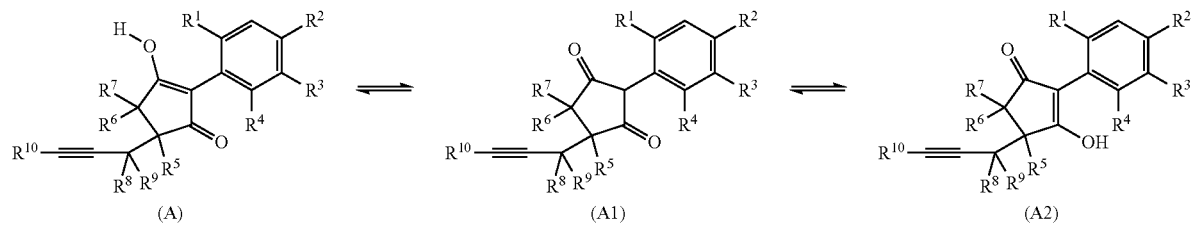

Also, when substituents contain double bonds, cis- and trans-isomers can exist.

This invention covers all such isomers and/or tautomers and/or mixtures thereof in all proportions. These isomers and/or tautomers are within the scope of the claimed compounds of formula (I).

According to a further aspect of the invention, there is provided a compound of formula (II):

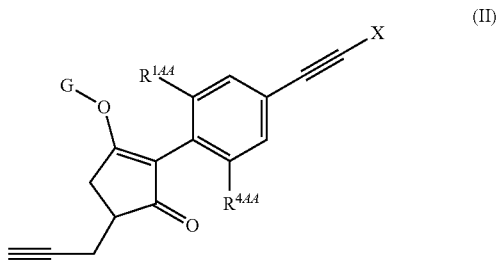

wherein:

X is methyl or chlorine;

$R^{1AA}$ is methoxy, ethoxy, $C_1$fluoroalkoxy (e.g. difluoromethoxy or trifluoromethoxy), ethyl, n-propyl, cyclopropyl or ethynyl;

$R^{4AA}$ is hydrogen, methoxy, ethoxy, $C_1$fluoroalkoxy (e.g. difluoromethoxy or trifluoromethoxy), or ethyl; and G is hydrogen, an agriculturally acceptable metal, or an agriculturally acceptable sulfonium or ammonium group; or G is —C(O)—$R^{AA}$ or —C(O)—$X^{CC}$—$R^{BB}$;

wherein $X^{CC}$ is oxygen or sulfur;

$R^{AA}$ is $C_1$-$C_{10}$alkyl, $C_2$-$C_6$alkenyl, $C_2$-$C_6$alkynyl, $C_3$-$C_6$cycloalkyl, $C_3$-$C_6$cycloalkyl-methyl-, $C_1$-$C_3$alkoxy$C_1$-$C_3$alkyl; phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or phenyl-methyl- in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; and $R^{BB}$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl, $C_3$-$C_6$cycloalkyl-methyl-, $C_1$-$C_3$alkoxy$C_1$-$C_3$alkyl; phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or phenyl-methyl- in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano;

and wherein the compound of formula (II) is optionally present as an agrochemically acceptable salt (e.g. agriculturally acceptable metal, sulfonium or ammonium salt) thereof.

Preferably, X is methyl. This is strongly preferred.

Preferably, $R^{1AA}$ is methoxy, ethoxy, difluoromethoxy, trifluoromethoxy, ethyl or n-propyl. More preferably, $R^{1AA}$ is methoxy, ethyl or n-propyl. Even more preferably, $R^{1AA}$ is methoxy or ethyl. Most preferably, $R^{1AA}$ is methoxy.

Preferably, $R^{4AA}$ is hydrogen, methoxy or ethyl. More preferably, $R^{4AA}$ is hydrogen or methoxy. Most preferably, $R^{4AA}$ is hydrogen.

Preferably, $R^{AA}$ is $C_1$-$C_6$alkyl, $C_3$-$C_6$cycloalkyl, $C_1$-$C_2$alkoxy$C_1$-$C_2$alkyl; or phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

Preferably, $R^{BB}$ is $C_1$-$C_6$alkyl, $C_2$-$C_5$alkenyl-$CH_2$—, $C_2$-$C_5$alkynyl-$CH_2$—, $C_3$-$C_6$cycloalkyl; or phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

Preferably, G is hydrogen, an agriculturally acceptable metal (e.g. an agriculturally acceptable alkali metal or alkaline earth metal), or an agriculturally acceptable sulfonium or ammonium group. Most preferably, G is hydrogen.

Particularly preferably, in the compound of formula (II):

X is methyl;

$R^{1AA}$ is methoxy, ethyl or n-propyl (more preferably, $R^{1AA}$ is methoxy or ethyl; or most preferably methoxy);

$R^{4AA}$ is hydrogen, methoxy or ethyl (more preferably, $R^{4AA}$ is hydrogen or methoxy; or most preferably hydrogen); and G is hydrogen, an agriculturally acceptable metal, or an agriculturally acceptable sulfonium or ammonium group (most preferably, G is hydrogen).

Particularly preferably, the compound of formula (II) is one of the following compounds:

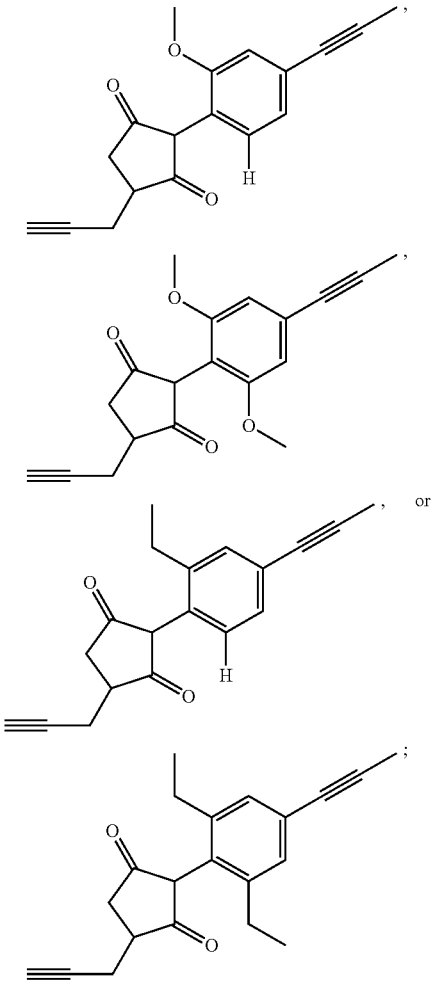

in each case optionally present as an agrochemically acceptable salt (e.g. agriculturally acceptable metal, sulfonium or ammonium salt) thereof.

Preferably, the compound of formula (II) is a compound of formula (IIC):

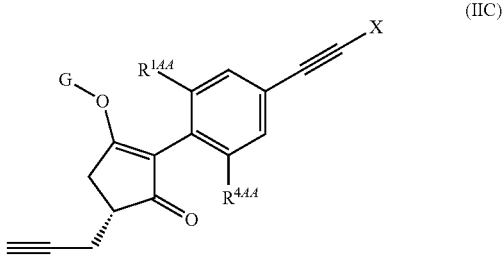

(IIC)

wherein X, $R^{1AA}$, $R^{4AA}$, and G are as defined herein, and wherein 40% or more (in particular 45% or more, preferably more than 50%, more preferably more than 70% or more than 90%) by molarity of the compound of formula (IIC) has the indicated stereochemistry at the ring-carbon atom bonded to —$CH_2$—C≡C—H.

A further aspect of the invention provides a herbicidal composition which comprises:

(i) a compound of formula (II), as defined herein, and (ii) an agrochemically acceptable carrier, diluent and/or solvent; and (iii) optionally one or more further herbicides and/or optionally a safener.

A further aspect of the invention provides a method of controlling grassy monocotyledonous weeds in crops of useful plants, comprising applying (e.g. post-emergence) a compound of formula (II), as defined herein, or a herbicidal composition comprising such a compound (e.g. as defined herein), to the weeds and/or to the plants and/or to the locus thereof. In this aspect, preferably, the crops of useful plants comprise wheat, barley, rye, triticale, sugarcane, soybean, peanut, pulse crops, cotton, rape, sunflower, linseed, sugarbeet, fodder beet, potato, and/or dicotyledonous vegetables. In this aspect, preferably, the grassy monocotyledonous weeds comprise (e.g. are) the preferred or particular grassy monocotyledonous weeds as defined herein e.g. for the compounds of formula (I).

Processes for Preparation of Compounds, e.g. Compounds of Formula (I)

Processes for preparation of compounds, e.g. a compound of formula (I) (which optionally can be an agrochemically acceptable salt thereof), are now described, and form further aspects of the present invention.

A compound of formula I, wherein G is:
—$C(X^a)$—$R^a$, —$C(X^b)$—$X^c$—$R^b$, —$C(X^d)$—$N(R^c)$—$R^d$, —$SO_2$—$R^e$, —$P(X^e)(R^f)$—$R^g$, —$CH_2$—$X^f$—$R^h$; or phenyl-$CH_2$— or phenyl-$CH(C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-$CH(C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_5$alkyl-C(O)—$CH_2$—, $C_1$-$C_6$alkoxy-C(O)—CH═CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;

may be prepared by treating a compound of formula (A), which is a compound of formula I wherein G is H, (a) with a reagent G1-Z, wherein G1-Z is an alkylating agent (wherein G1 is an organic group according to G within the compound of formula (I) and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—$CH_2$—$X^f$—$R^h$ wherein $X^f$ is oxygen, a chloromethyl alkyl sulfide Cl—$CH_2$—$X^f$—$R^h$ wherein $X^f$ is sulphur, a suitable optionally substituted benzyl halide (e.g. chloride) such as Cl—$CH_2$-[optionally substituted phenyl], [optionally substituted phenyl]-C(O)—$CH_2$-[halogen e.g. Cl], $C_1$-$C_6$alkoxy-C(O)—$CH_2$-[halogen e.g. Cl], $C_1$-$C_6$alkoxy-C(O)—CH═CH-[halogen e.g. Cl], a suitable alkenyl or alkynyl halide (e.g. chloride) such as $C_2$-$C_7$alken-1-yl-$CH_2$-[halogen e.g. Cl] or $C_2$-$C_7$alkyn-1-yl-$CH_2$-[halogen e.g. Cl], or another organic halide suitable for preparing a (non-carbonyl, non-thiocarbonyl carbon)-linked G (or G1) group; or (b) [e.g. to prepare carbonyl-carbon-linked or thiocarbonyl-carbon-linked G groups] with an acylating agent such as a carboxylic acid, HO—$C(X^a)R^a$, wherein $X^a$ is oxygen, an acid chloride, Cl—$C(X^a)R^a$, wherein $X^a$ is oxygen, or an acid anhydride, $[R^aC(X^a)]_2O$, wherein $X^a$ is oxygen, or an isocyanate, $R^cN$═C═O, or a carbamoyl chloride, Cl—$C(X^d)$—$N(R^c)$—$R^d$ (wherein $X^d$ is oxygen and with the proviso that neither $R^c$ or $R^d$ is hydrogen), or a thiocarbamoyl chloride Cl—$(X^d)$—$N(R^c)$—$R^d$ (wherein $X^d$ is sulfur and with the proviso that neither $R^c$ or $R^d$ is hydrogen), or a chloroformate, Cl—$C(X^b)$—$X^c$—$R^b$ (wherein $X^b$ and $X^c$ are oxygen), or a chlorothioformate Cl—$C(X^b)$—$X^c$—$R^b$ (wherein $X^b$ is oxygen and $X^c$ is sulfur), or a chlorodithioformate Cl—$C(X^b)$—$X^c$—$R^b$ (wherein $X^b$ and $X^c$ are sulfur), or an isothiocyanate, $R^cN$═C═S; or (c) by sequential treatment with carbon disulfide and an alkylating agent; or (d) with a phosphorylating agent such as a phosphoryl chloride, Cl—$P(X^e)(R^f)$—$R^g$; or (e) with a sulfonylating agent such as a sulfonyl chloride Cl—$SO_2$—$R^e$, preferably in the presence of at least one equivalent of base.

Where substituents $R^6$ and $R^7$ are not equal to substituents $R^5$ and —$CR^8R^9$—C≡C—$R^{10}$, the above-described reactions may produce, in addition to a compound of formula (I), a second compound of formula (IA).

This invention covers both a compound of formula (I) and a compound of formula (IA), together with mixtures of these compounds in any ratio.

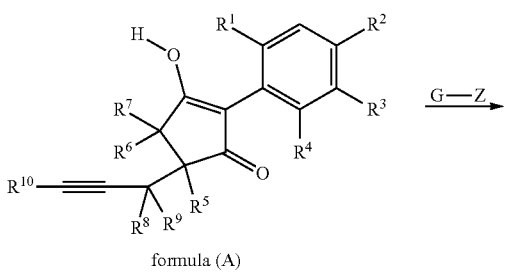

formula (A)

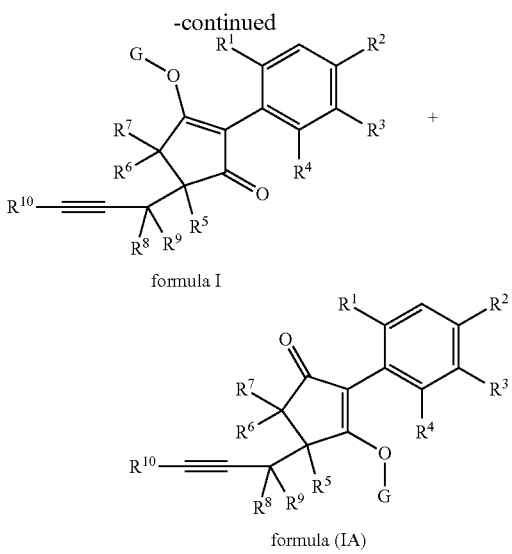

formula I formula (IA)

The O-alkylation of cyclic 1,3-diones is known; suitable methods are described, for example, by T. Wheeler, U.S. Pat. No. 4,436,666. Alternative procedures have been reported by M. Pizzorno and S. Albonico, *Chem. Ind. (London)*, (1972), 425-426; H. Born et al., *J. Chem. Soc.*, (1953), 1779-1782; M. G. Constantino et al., *Synth. Commun.*, (1992), 22 (19), 2859-2864; Y. Tian et al., *Synth. Commun.*, (1997), 27 (9), 1577-1582; S. Chandra Roy et al., *Chem. Letters*, (2006), 35 (1), 16-17; and/or P. K. Zubaidha et al., *Tetrahedron Lett.*, (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, or sodium hydride, and suitable organic bases include trialkylamines, such as trimethylamine or triethylamine, pyridines or other amine bases such as 1,4-diazobicyclo[2.2.2]-octane or 1,8-diazabicyclo[5.4.0]undec-7-ene. Preferred bases include triethylamine and pyridine. Suitable solvents for this reaction are selected to be compatible with the reagents and include ethers such as tetrahydrofuran or 1,2-dimethoxyethane or halogenated solvents such as dichloromethane or chloroform. Certain bases, such as pyridine or triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide or N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, *Tetrahedron Lett.*, (1999), 40 (43), 7595-7598; T. Isobe and T. Ishikawa, *J. Org. Chem.*, (1999), 64 (19), 6984-6988 and/or K. Nicolaou, T. Montagnon, G. Vassilikogiannakis, C. Mathison, *J. Am. Chem. Soc.*, (2005), 127(24), 8872-8888.

Phosphorylation of cyclic 1,3-diones may be effected e.g. using a phosphoryl halide or thiophosphoryl halide and a base e.g. by procedures analogous to those described by L. Hodakowski, U.S. Pat. No. 4,409,153.

Sulfonylation of a compound of formula (A) may be achieved e.g. using an alkyl or aryl sulfonyl halide, preferably in the presence of at least one equivalent of base, for example by the procedure of C. Kowalski and K. Fields, *J. Org. Chem.*, (1981), 46, 197-201.

A compound of formula (A) may be prepared via the cyclisation of a compound of formula (B), preferably in the presence of an acid or base, and optionally in the presence of a suitable solvent, by analogous methods to those described by T. Wheeler, U.S. Pat. No. 4,209,532. Compounds of formula (B) have been particularly designed as intermediates in the synthesis of the compounds of formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (B) wherein R is alkyl (preferably methyl or ethyl) may also be cyclised under basic conditions in the presence of at least one equivalent of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (B), wherein R is alkyl, may be produced from a compound of formula (B), wherein R is H, by esterification under known conditions, for example by treatment with an alcohol, R—OH, in the presence of an acid catalyst.

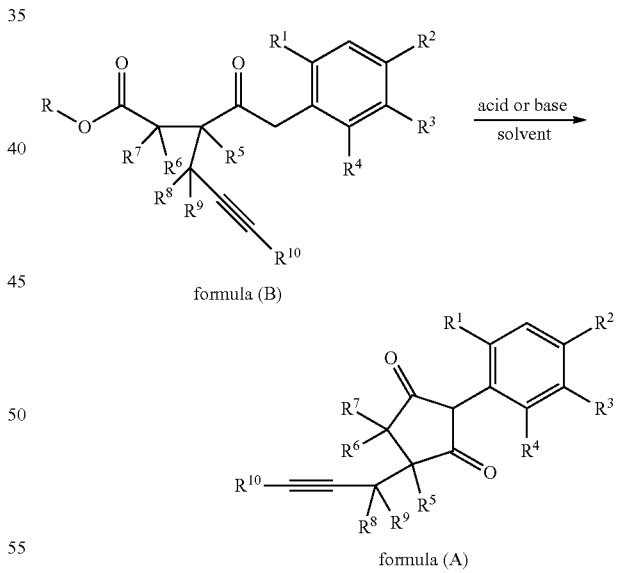

formula (B)

formula (A)

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, by similar processes to those described by, for example, T. Wheeler, U.S. Pat. No. 4,209,532. Alternatively, a compound of formula (B), wherein R is alkyl or H may be prepared from a compound of formula (C), wherein R' is alkyl (preferably methyl), through a Krapcho decarboxylation procedure under known conditions using known reagents (see for example G. Quallich, P. Morrissey, Synthesis, (1993), (1), 51-53).

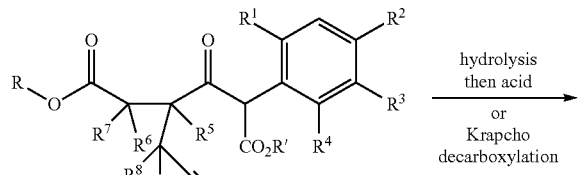

formula (C)

A compound of formula (C) wherein R' is as previously described and R is alkyl may be prepared by treating a compound of formula (D) with a suitable carboxylic acid chloride of formula (E) wherein R is alkyl under basic conditions. Suitable bases include potassium tert-butoxide, sodium bis(trimethyl-silyl)amide and lithium diisopropyl-amide and the reaction is preferably conducted in a suitable solvent, such as tetrahydrofuran or toluene, at a temperature between −78° C. and 30° C. Under similar conditions a compound of formula (C), wherein R is H, may also be prepared from a suitable anhydride of formula (F) and a compound of formula (D).

In a further approach a compound of formula (A), in particular wherein $R^2$ is optionally substituted phenyl; or optionally substituted heteroaryl, can be prepared directly from a compound of formula (G), wherein G is hydrogen or preferably $C_1$-$C_3$ alkyl, under standard cross-coupling conditions such as a Suzuki-Miyaura coupling. Similarly, a compound of formula (A), in particular wherein $R^3$ is optionally substituted phenyl or optionally substituted heteroaryl, can be prepared directly from a compound of formula (H) under standard cross-coupling conditions such as a Suzuki-Miyaura coupling. Conditions suitable for effecting the Suzuki-Miyaura cross-coupling of an aryl halide of formula (G) or formula (H) with an aryl- or heteroarylboronic acid of formula $R^2$—$B(OH)_2$, or a suitable salt or ester thereof, are known in the literature (see, for example K. Billingsley and S. Buchwald, J. Am. Chem. Soc., (2007), 129, 3358-3366; H. Stefani, R. Cella and A. Vieira, Tetrahedron, (2007), 63, 3623-3658; N. Kudo, M. Perseghini and G. Fu, Angew. Chem. Int. Ed., (2006), 45, 1282-1284; A. Roglans, A. Pla-Quintana and M. Moreno-Mañas, Chem. Rev., (2006), 106, 4622-4643; J-H Li, Q-M Zhu and Y-X Xie, Tetrahedron (2006), 10888-10895; S. Nolan et al., J. Org. Chem., (2006), 71, 685-692; M. Lysén and K. Köhler, Synthesis, (2006), 4, 692-698; K. Anderson and S. Buchwald, Angew. Chem. Int. Ed., (2005), 44, 6173-6177; Y. Wang and D. Sauer, Org. Lett., (2004), 6 (16), 2793-2796; I. Kondolff, H. Doucet and M, Santelli, Tetrahedron, (2004), 60, 3813-3818; F. Bellina, A. Carpita and R. Rossi, Synthesis (2004), 15, 2419-2440; H. Stefani, G. Molander, C-S Yun, M. Ribagorda and B. Biolatto, J. Org. Chem., (2003), 68, 5534-5539; A. Suzuki, Journal of Organometallic Chemistry, (2002), 653, 83; G. Molander and C-S Yun, Tetrahedron, (2002), 58, 1465-1470; G. Zou, Y. K. Reddy and J. Falck, Tetrahedron Lett., (2001), 42, 4213-7215; S. Darses, G. Michaud and J-P. Genêt, Eur. J. Org. Chem., (1999), 1877-1883; M. Beavers et al., WO2005/012243; J. Org. Chem. (1994), 59, 6095-6097; A. Collier and G. Wagner, Synthetic Communications, (2006), 36; 3713-3721).

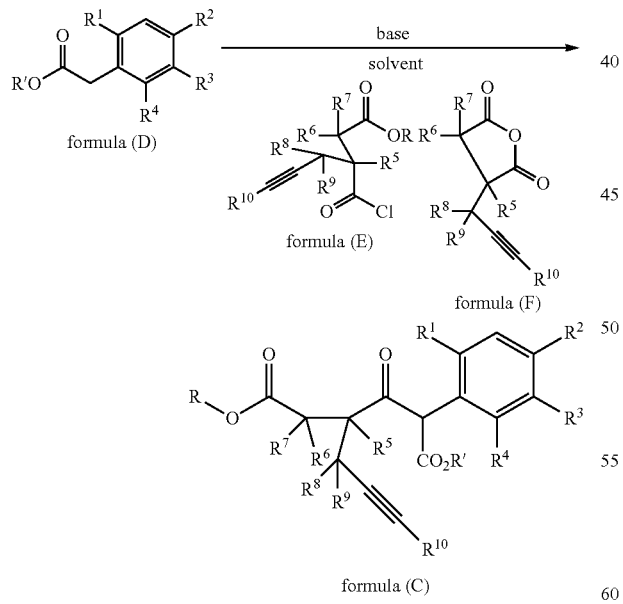

formula (D)

formula (E)

formula (F)

formula (C)

Compounds of formula (E) and formula (F) are known or can be prepared from known reagents using known methods. A compound of formula (D) can be prepared from known reagents using known methods, see for example those methods described in WO08/071405, WO08/110308, WO08/145336, WO09/019015 and WO09/074314.

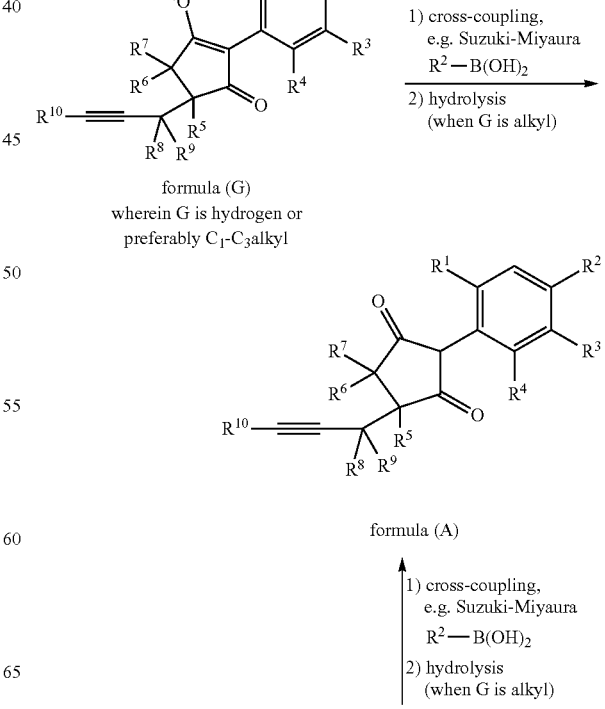

formula (G)
wherein G is hydrogen or preferably $C_1$-$C_3$alkyl 1) cross-coupling, e.g. Suzuki-Miyaura
$R^2$—$B(OH)_2$
2) hydrolysis (when G is alkyl)

formula (A)

1) cross-coupling, e.g. Suzuki-Miyaura
$R^2$—$B(OH)_2$
2) hydrolysis (when G is alkyl)

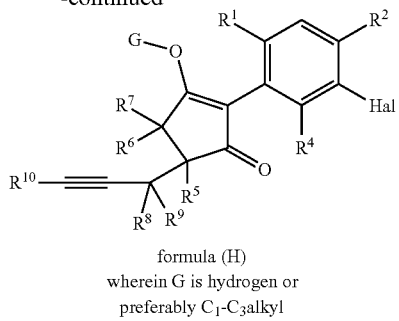

formula (H)
wherein G is hydrogen or
preferably $C_1$-$C_3$alkyl

Compounds of formula (G) (wherein G is hydrogen) and formula (H) (wherein G is hydrogen) can be prepared by methods analogous to those described for the preparation of compounds of formula (A) from compounds of formula (B), starting from appropriately substituted acyclic precursors.

In an alternative approach compounds of formula (A) can be prepared from compounds of formula (I) or compounds of formula (J) under similar conditions. Compounds of formula (I) and (J) can be derived from compounds of formula (G) and compounds of formula (H) respectively. Compounds of formula (G) and formula (H) can be converted to compounds of formula (I) and formula (J) using known transition-metal catalysed borylation chemistry (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363).

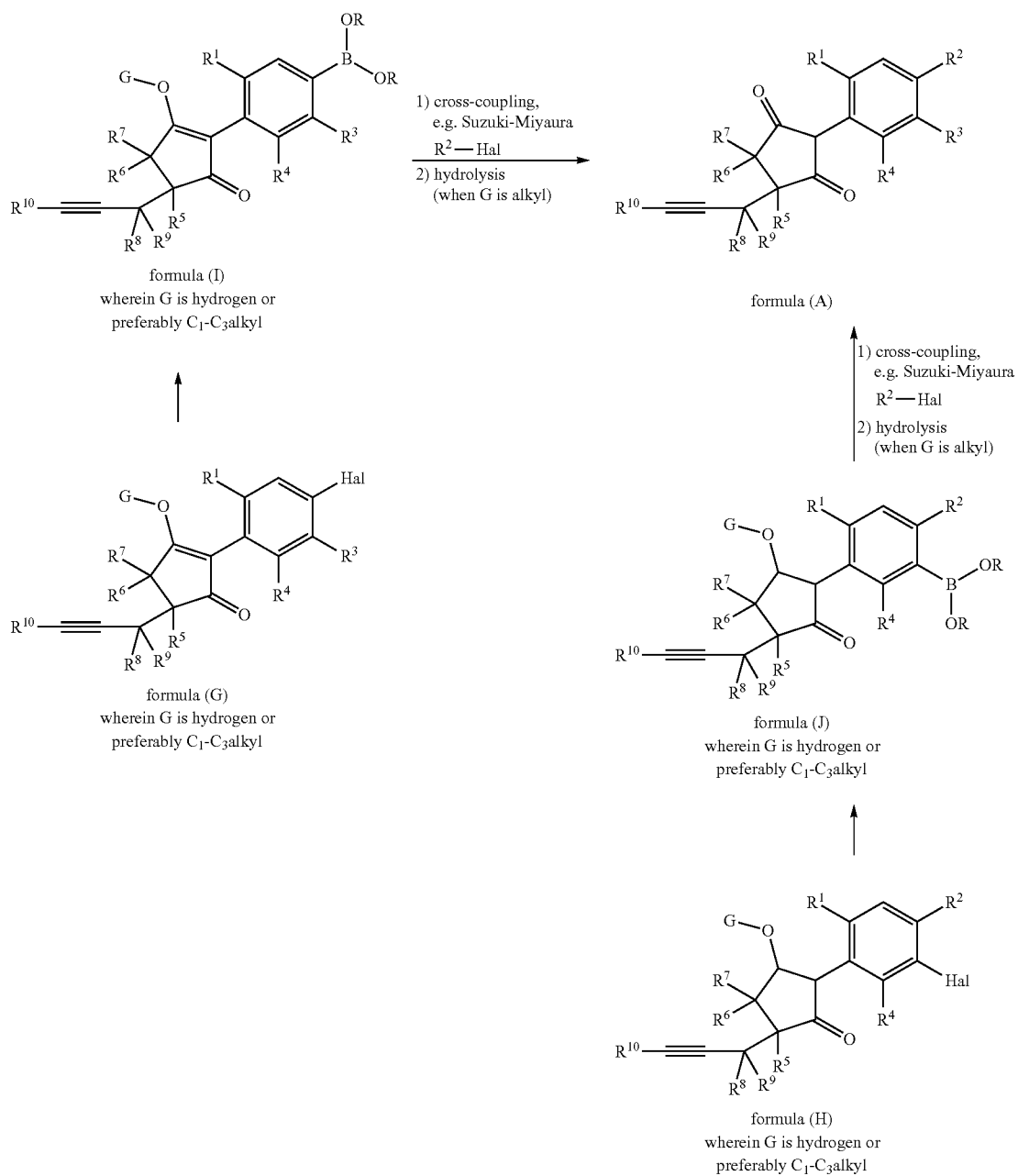

Alternatively a compound of formula (I) may be prepared from a compound of formula (L) by C—H borylation with a suitable borylating agent, a suitable catalyst system, in a suitable solvent at a suitable temperature. Similarly, a compound of formula (J) may be prepared from a compound of formula (K) by C—H borylation with a suitable borylating agent, a suitable catalyst system, in a suitable solvent at a suitable temperature. Suitable catalysts include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, Chemical Society Reviews (2011), 40(4), 1992-2002 and T. Ishiyama, N. Miyaura, Pure and Applied Chemistry (2006), 78(7), 1369-1375). Preferred conditions include treating a compound of formula (L) or (K) with 0.05-10% 1,5-cyclooctadiene)(methoxy)iridium(I) dimer (with respect to a compound of formula (L) or (K)), 0.05-10% 4,4'-di-tert-butyl-2,2'-dipyridyl (with respect to a compound of formula (L) or (K)), and 1-2 equivalents bis(pinacolato)diboron (with respect to a compound of formula (L) or (K)) in methyl tert-butyl ether at a temperature between 50° C.–150° C., optionally under microwave irradiation, as described by P. Harrisson, J. Morris, T. B. Marder, P. G. Steel, Organic Letters (2009), 11(16), 3586-3589.

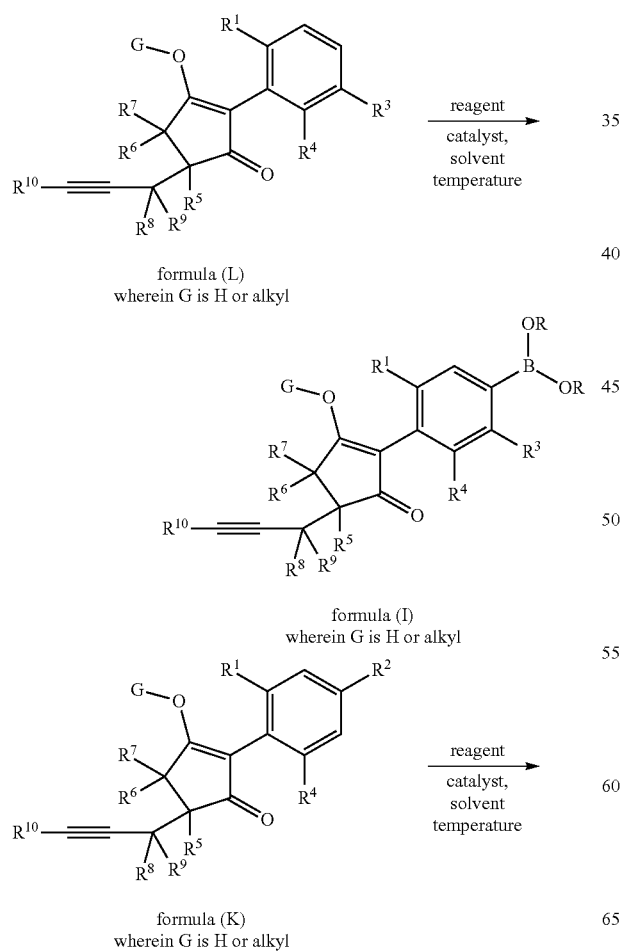

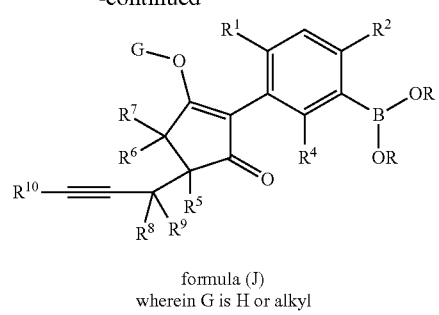

formula (J)
wherein G is H or alkyl

Compounds of formula (L) and formula (K), wherein G is hydrogen, can be prepared by methods analogous to those described for the preparation of compounds of formula (A) from compounds of formula (B), starting from appropriately substituted acyclic precursors.

Additionally, a compound of formula (A) may be prepared by the Pinacol rearrangement of a compound of formula (M) or a compound of formula (N), wherein R''' is $C_1$-$C_4$ alkyl (preferably methyl), under protic or Lewis acidic conditions (see, for example, Eberhardt, U. et. al. Chem. Ber. (1983), 116(1), 119-35 and Wheeler, T. N. U.S. Pat. No. 4,283,348). Preferred conditions include reacting a compound of formula (M) or (N) with trifluoroacetic acid at room temperature.

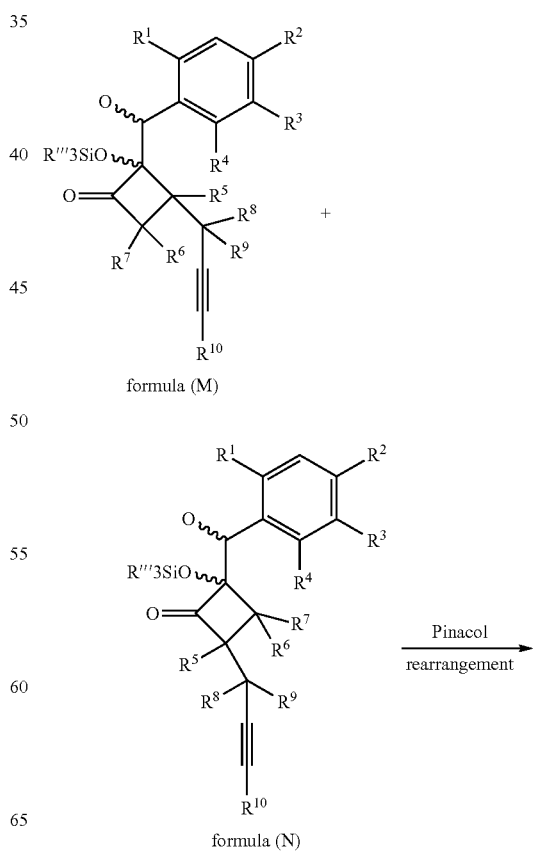

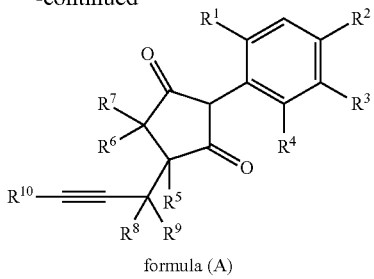

formula (A)

A compound of formula (M) and a compound of formula (N), wherein R''' is $C_1$-$C_4$ alkyl (preferably methyl), may be prepared by treating a compound of formula (P) with an aldehyde of formula (O) in the presence of an acid such as boron trifluoride, titanium chloride or magnesium iodide, optionally in a suitable solvent such as dichloromethane at a temperature between −80° C. and 30° C. (see, for example, Li, W.-D. Z. and Zhang, X.-X. Org. Lett. (2002), 4(20), 3485-3488; Shimada, J. et al. J. Am. Chem. Soc. (1984), 106(6), 1759-73; Eberhardt, U. et. al. Chem. Ber. (1983), 116(1), 119-35 and Wheeler, T. N. U.S. Pat. No. 4,283,348). A compound of formula (O) is known or can be prepared from known reagents using known methods.

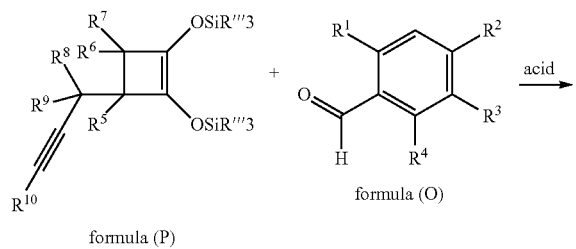

formula (P)  formula (O)

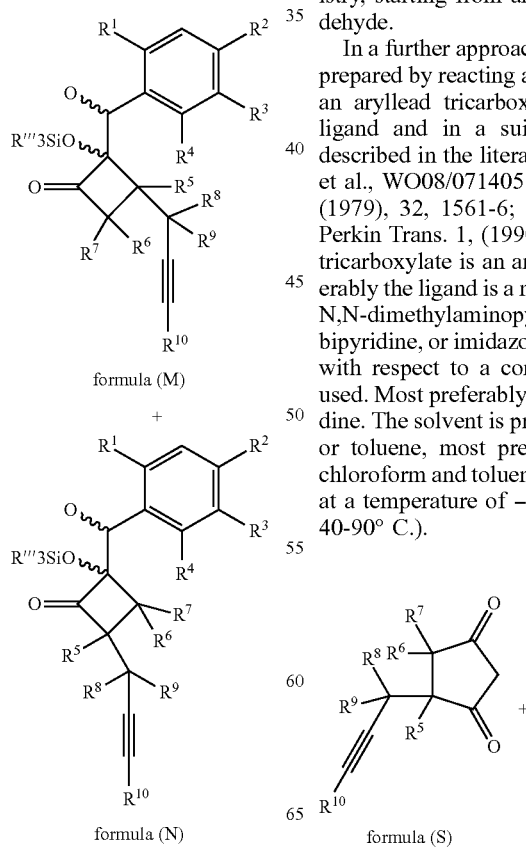

formula (M)

+ formula (N)

Compounds of formula (P), wherein R'''' is $C_1$-$C_4$ alkyl, preferably methyl, may be prepared from compounds of formula (Q), where in R'''' is an alkyl group, preferably methyl, in the presence of chloro tri-$C_1$-$C_4$alkyl silyl and a metal, preferably sodium, in a suitable solvent such as toluene or diethyl ether at a temperature between 20° C. and 150° C. (see, for example, Blanchard, A. N. and Burnell, D. J. Tetrahedron Lett. (2001), 42(29), 4779-4781 and Salaun, J. et al. Tetrahedron (1989), 45(10), 3151-62).

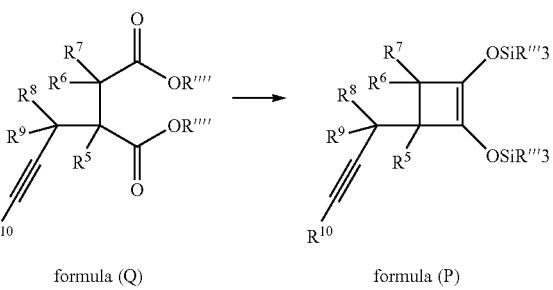

formula (Q)  formula (P)

Compounds of formula (Q) are either known compounds or can be prepared from known reagents using known methods.

A compound of formula (G) (wherein G is hydrogen) or a compound of formula (H) (wherein G is hydrogen) can be prepared by analogous Pinacol rearrangement chemistry, starting from an appropriately functionalised benzaldehyde. Similarly, a compound of formula (L) (wherein G is hydrogen) or a compound of formula (K) (wherein G is hydrogen) can be prepared by analogous Pinacol rearrangement chemistry, starting from an appropriately functionalised benzaldehyde.

In a further approach, a compound of formula (A) may be prepared by reacting a compound of formula (S) with a with an aryllead tricarboxylate, in the presence of a suitable ligand and in a suitable solvent. Similar reactions are described in the literature (see for example M. Muehlebach et al., WO08/071405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (R). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (S) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

formula (S)

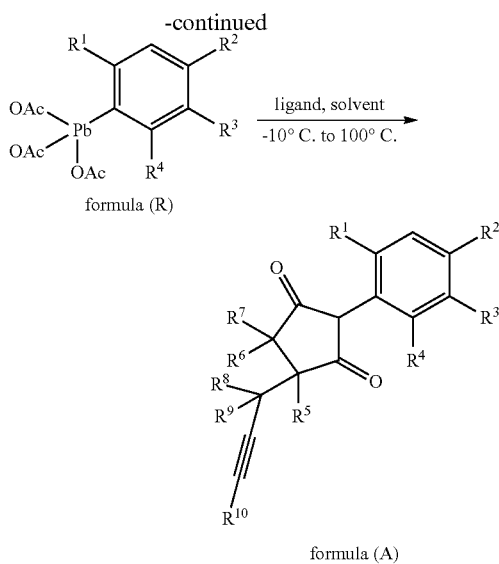

formula (R)

formula (A)

Compounds of formula (S) are known compounds or can be prepared from known reagents using known methods. See for example M. Gulias, J. R. Rodriguez, L. Castedo J. L. Mascarenas, Org. Lett., Vol. 5, No. 11, 2003.

A compound of formula (R) may be prepared from a compound of formula (T) by treatment with lead tetraacetate in a suitable solvent, for example chloroform, at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

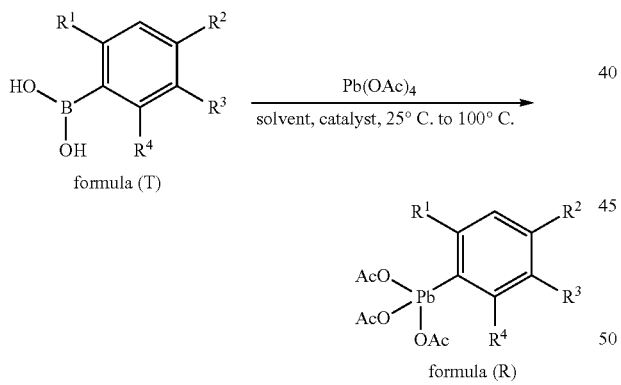

formula (T)

formula (R)

An aryl boronic acid of formula (T) may be prepared from an aryl halide of formula (V) by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (V) may be treated with an alkyl lithium or Grignard at low temperature, and the aryl magnesium or aryl lithium reagent obtained is allowed to react with a trialkyl borate, $B(OR'')_3$, preferably trimethylborate, to give an aryl dialkylboronate of formula (U) which may be hydrolysed to the desired boronic acid of formula (T) under acidic conditions. Alternatively the same overall transformation of compound (U) to compound (T) may be achieved through a stepwise palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester.

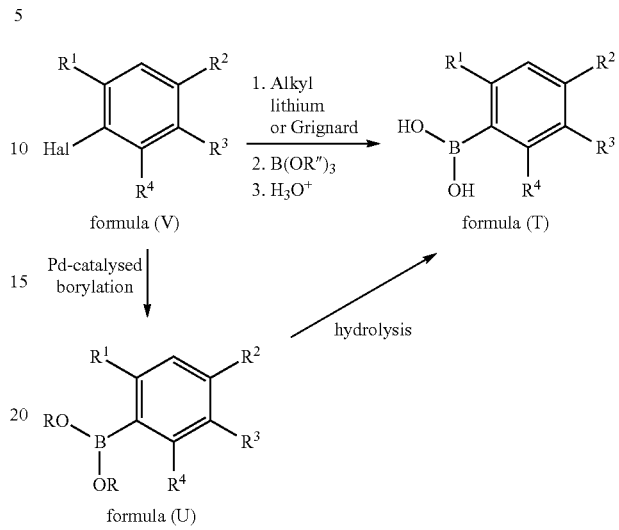

formula (V)

formula (T)

formula (U)

A compound of formula (G) (wherein G is hydrogen) or a compound of formula (H) (wherein G is hydrogen) can be prepared using analogous aryl lead chemistry, starting from an appropriately functionalised aryllead tricarboxylate. Similarly, a compound of formula (L) (wherein G is hydrogen) or a compound of formula (K) (wherein G is hydrogen) can be prepared using analogous aryl lead chemistry, starting from an appropriately functionalised aryllead tricarboxylate.

In an alternative approach, a compound of formula (A) may be prepared by the reaction of a compound of formula (W) with an arylboronic acid of formula (T) in the presence of a suitable palladium catalyst, a suitable base, optionally in the presence of a suitable ligand or additive, and in a suitable solvent.

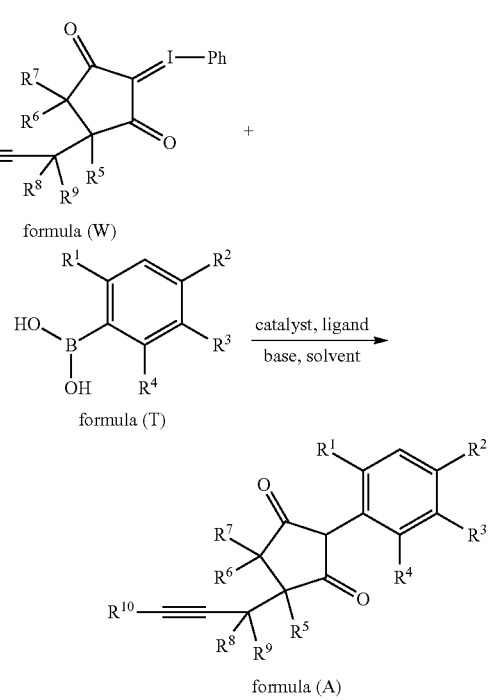

formula (W)

formula (T)

formula (A)

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclo-hexylphosphino-2',6'-dimethoxybiphenyl, 2-dicyclohexylphosphino-2',4',6'-triisopropyl-biphenyl, 1,1'-bis(diphenyl-phosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (W) may be prepared from a compound of formula (S) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

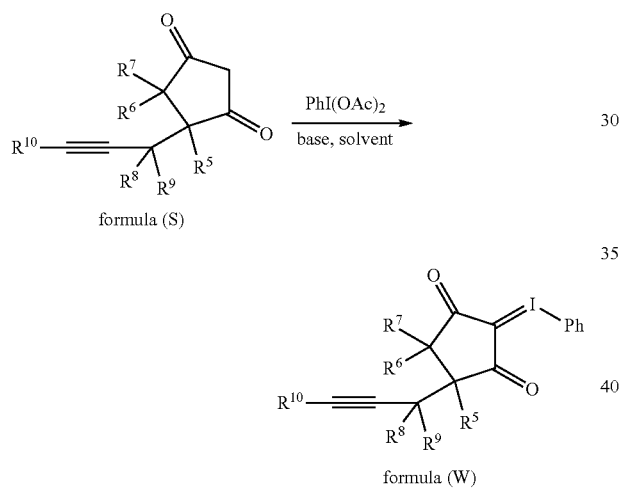

A compound of formula (G) (wherein G is hydrogen) or a compound of formula (H) (wherein G is hydrogen) can be prepared using analogous iodonium ylide chemistry, starting from an appropriately functionalised aryl boronic acid. Similarly, a compound of formula (L) (wherein G is hydrogen) or a compound of formula (K) (wherein G is hydrogen) can be prepared using analogous iodonium ylide chemistry, starting from an appropriately functionalised aryl boronic acid.

In a further approach, a compound of formula I (wherein wherein G is preferably $C_{1-4}$ alkyl) may be prepared by reacting a compound of formula (X) (wherein G is preferably methyl or ethyl, and Hal is a halogen, preferably bromine or iodine), with an arylboronic acid of formula (T) in the presence of a suitable palladium catalyst, for example 0.001-50% palladium(II) acetate with respect to compound (X), a base for example 1 to 10 equivalents potassium phosphate with respect to compound (X), preferably in the presence of a suitable ligand for example 0.001-50% (2-dicyclohexylphosphino)-2',6'-dimethoxybiphenyl with respect to compound (X), and in a suitable solvent for example toluene, preferably between 25° C. and 200° C. Similar couplings are known in the literature (see for example, Y. Song, B. Kim and J.-N. Heo, Tetrahedron Letters (2005), 46 (36), 5987-5990). A compound of formula I can be converted to a compound of formula (A) by hydrolysis under known conditions.

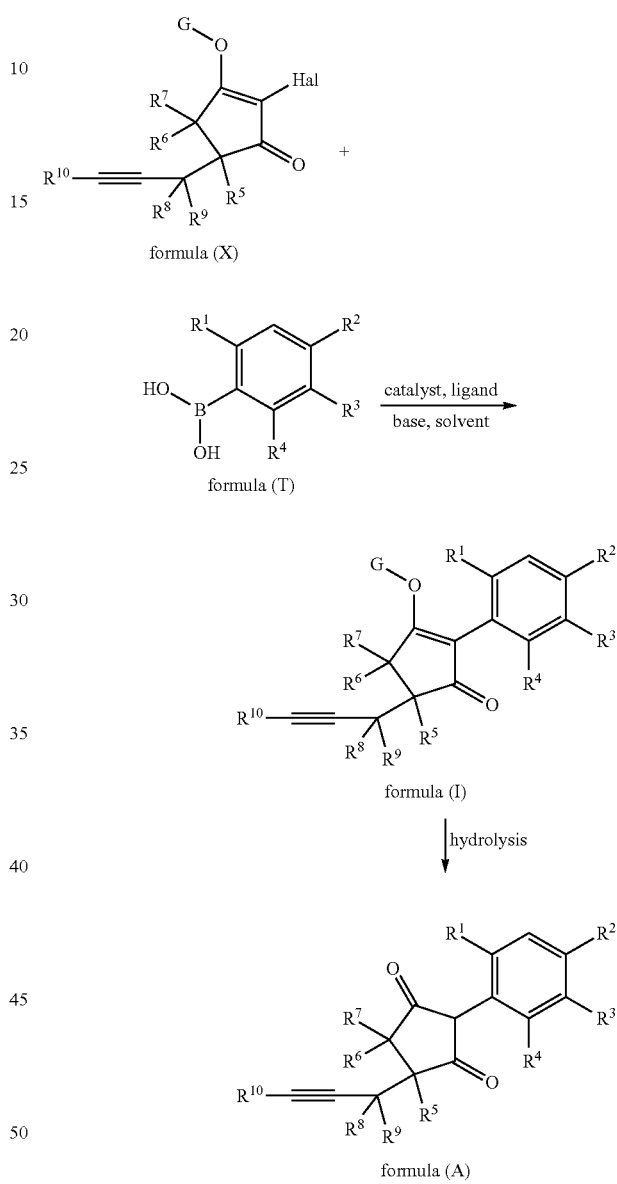

A compound of formula (X) may be prepared by halogenating a compound of formula (S), followed by reaction of the resulting halide of formula (Z) with a $C_1$-$C_4$alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (X) may be prepared by reacting a compound of formula (S) with a $C_1$-$C_4$alkyl halide or a tri-$C_1$-$C_4$-alkylorthoformate, and halogenating the resulting enol ether of formula (Y) under known conditions (see for example Y. Song, B. Kim and J.-N. Heo, Tetrahedron Letters (2005), 46(36), 5987-5990).

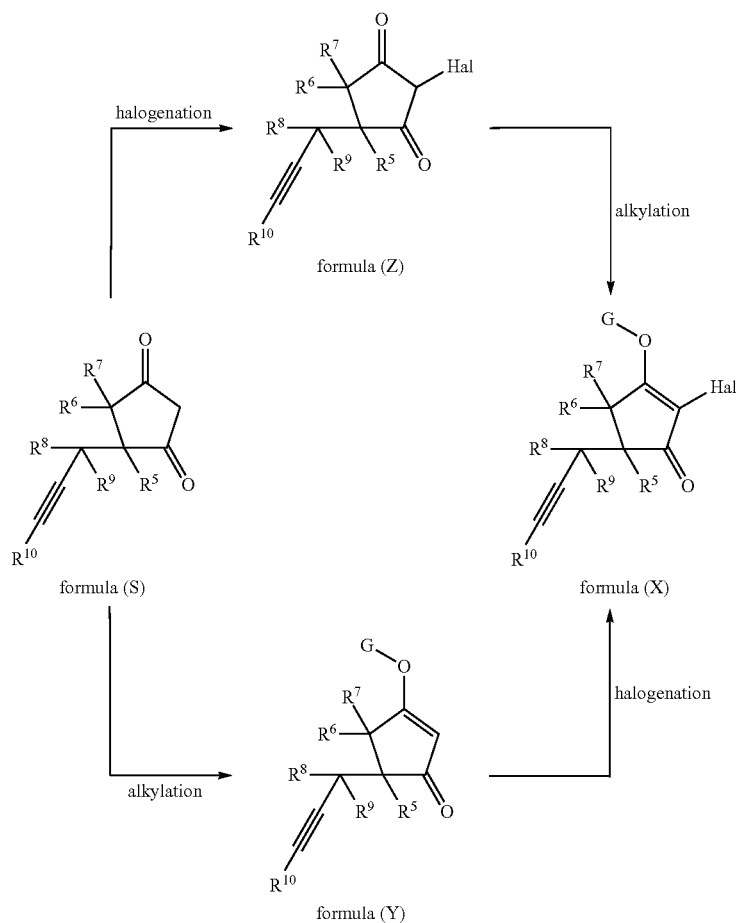

formula (Z)

formula (S)

formula (X)

formula (Y)

A compound of formula (G) (wherein G is hydrogen) or a compound of formula (H) (wherein G is hydrogen) can be prepared using analogous Suzuki-Miyaura chemistry, starting from an appropriately functionalised aryl boronic acid. Similarly, a compound of formula (L) (wherein G is hydrogen) or a compound of formula (K) (wherein G is hydrogen) can be prepared using analogous Suzuki-Miyaura chemistry, starting from an appropriately functionalised aryl boronic acid.

In a further approach, a compound of formula (A) may be prepared by reacting a compound of formula (S) with a compound of formula (V) in the presence of a suitable palladium catalyst, for example 0.001-50% palladium(II) acetate with respect to compound (S) and a base, for example 1 to 10 equivalents potassium phosphate with respect to compound (S), preferably in the presence of a suitable ligand, for example 0.001-50% (2-dicyclohexylphosphino)-2',4',6'-triisopropylbiphenyl with respect to compound (S), and in a suitable solvent for example dioxane), preferably between 25° C. and 200° C. and optionally under microwave heating. Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (S) with a compound of formula (V) in the presence of a suitable copper catalyst (for example 0.001-50% copper(I) iodide with respect to compound (S), a base for example 1 to 10 equivalents cesium carbonate with respect to compound (S), preferably in the presence of a suitable ligand, for example 0.001-50% L-proline with respect to compound (S), and in a suitable solvent for example dimethylsulfoxide, preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

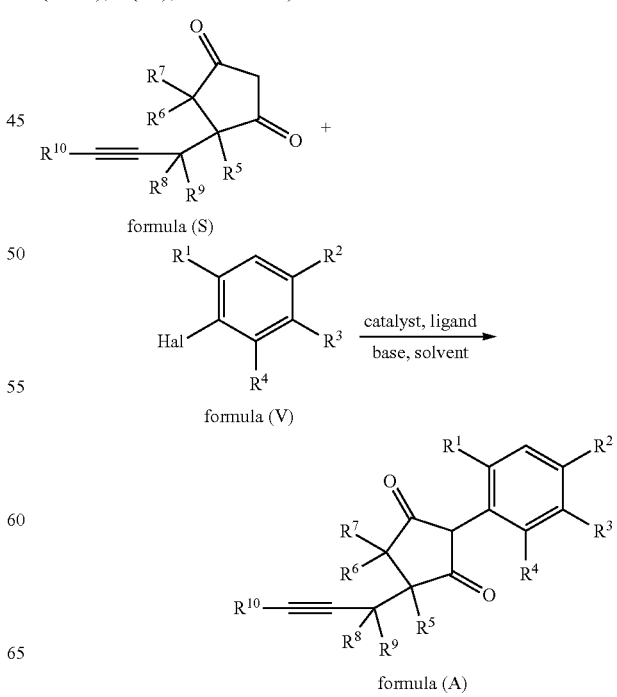

formula (S)

formula (V)

formula (A)

A compound of formula (G) (wherein G is hydrogen) or a compound of formula (H) (wherein G is hydrogen) can be prepared using analogous palladium-catalysed arylation chemistry, starting from an appropriately functionalised aryl halide (or pseudohalide such as triflate, mesylate or tolsylate). Similarly, a compound of formula (L) (wherein G is hydrogen) or a compound of formula (K) (wherein G is hydrogen) can be prepared using analogous palladium-catalysed arylation chemistry, starting from an appropriately functionalised aryl halide (or pseudohalide such as triflate, mesylate or tolsylate).

In a further approach compounds of formula I can be obtained by reacting a compound of formula (Z) with a compound of formula (1AA) wherein LG is a leaving group such as halogen (preferably iodide or bromide) or an activated alcohol, preferably triflate, mesylate or tosylate, under basic conditions. Suitable bases include lithium diisopropylamide, sodium hexamethyldisilazide and potassium tert-butoxide. The reaction is preferably conducted in a suitable solvent such as tetrahydrofuran at a temperature between −80° C. and 30° C. Similar reactions are described by Gulias, M. et al. Org. Lett. (2003), 5(11), 1975-1977. Compounds of formula (AA) are known compounds, or can be prepared from known compounds using known reagents.

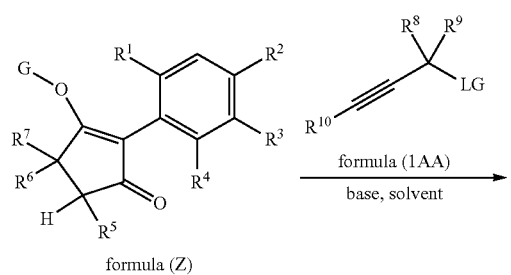

formula (Z)

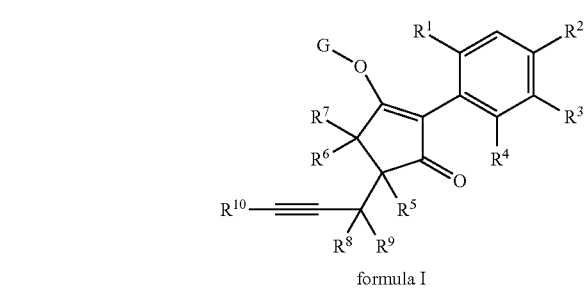

formula I wherein G is alkyl

A compound of formula (Z) may be prepared by analogous methods to those described previously. Alternatively a compound of formula (Z), wherein $R^6$ is hydrogen, may be prepared by reduction of a compound of formula (AA) under conditions which are compatible with the substrate, for example in the presence of sodium borohydride and cuprous chloride, as described by M. Narisada, I. Horibe, F. Watanabe and K. Takeda, Journal of Organic Chemistry (1989), 54(22), 5308-13.

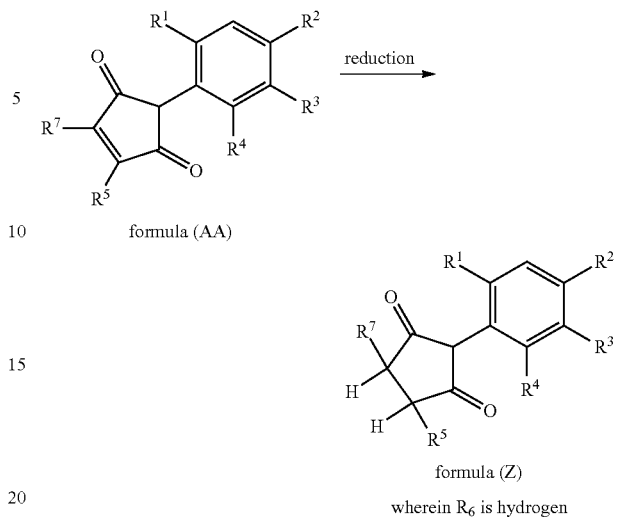

formula (AA)

formula (Z)

wherein $R_6$ is hydrogen

A compound of formula (AA) may be prepared by oxidising a compound of formula (AB) in a suitable solvent such as toluene, acetone, chloroform, dichloromethane or 1,4-dioxane. A wide range of oxidants can be used for effecting this transformation, including inorganic oxidants such as chromium trioxide, pyridinium dichromate, manganese dioxide and aluminium alkoxides such as aluminium isopropoxide, as well as organic oxidants such as 2,3-dichloro-5,6-dicyano-p-benzoquinone and hypervalent iodine oxidants such as 1,1,1,-tris(acetyloxy)-1,1-dihydro-1,2-benziodoxol-3-(1H)-one (Dess-Martin periodinane). Suitable procedures are described, for example, by K. Saito and H. Yamachika, U.S. Pat. No. 4,371,711 and by G. Piancatelli et al., Tetrahedron (1978), 34, 2775. The use of chromium trioxide in a mixture of sulfuric acid and acetone (Jones reagent) is preferred.

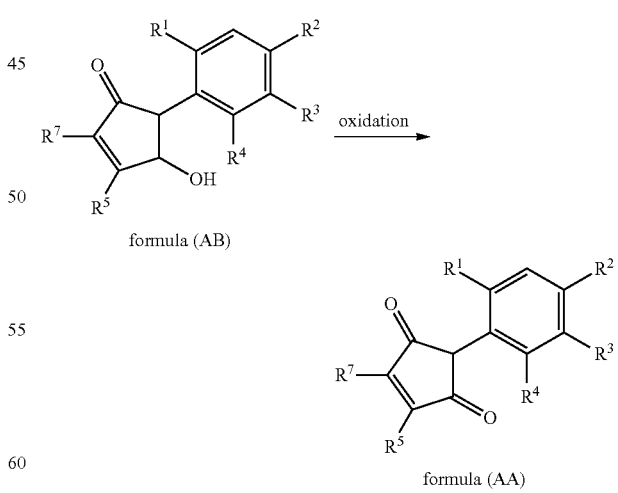

formula (AB)

formula (AA)

A compound of formula (AA) may be prepared from a compound of formula (AC) by treatment with a suitable acid catalyst in the presence of water and optionally in the presence of a suitable solvent.

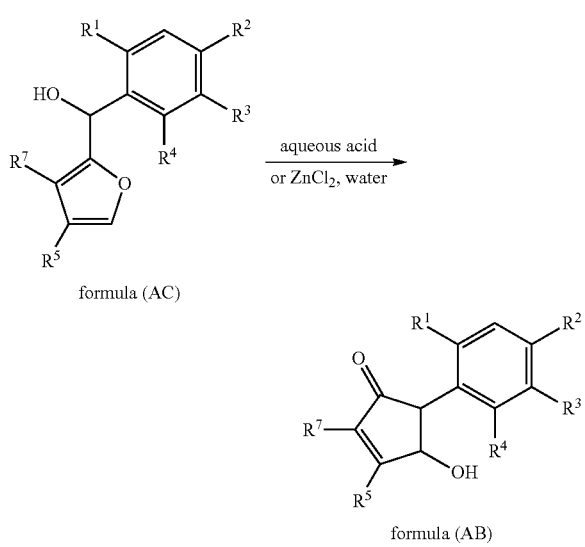

formula (AC)

formula (AB)

For example, a compound of formula (AC) may be converted to a compound of formula (AB) in the presence of an aqueous solution of an acid such as phosphoric acid or polyphosphoric acid under conditions described, for example by K. Saito and H. Yamachika, U.S. Pat. No. 4,371,711. Alternatively a compound of formula (AB) may be prepared from a compound of formula (AC) by rearrangement in the presence of a Lewis acid catalyst such as zinc chloride according to the procedure of G. Piancatelli et al., Tetrahedron, (1978), 34, 2775.

A compound of formula (AC) may be prepared by the addition of a suitable aryl organometallic reagent, such as an arylmagnesium halide of formula (AE) wherein Hal is a halide such as chloride, bromide or iodide, or an aryllithium reagent of formula (AD), or a diarylzinc reagent of formula (AF), to a furan-2-carboxaldehyde of formula (AJ) according to known procedures (see, for example, G. Panda et al., Tetrahedron Lett., (2005), 46, 3097). Alternatively a compound of formula (AC) may be prepared by the addition of a suitable 2-furyl organometallic reagent, such as 2-furylmagnesium halide of formula (AG) wherein Hal is a halide such as chloride, bromide or iodide, or a 2-furyllithium reagent of formula (AH) or a 2-furylzinc reagent of formula (AI), to a benzaldehyde of formula (O) according to known procedures. The organometallic reagents of formula (AE), formula (AD) and formula (AF) may be made by known methods from a compound of formula (V). Similarly, the organometallic reagents of formula (AG), formula (AH) and formula (AI) may be made by known methods from an appropriately functionalised furan.

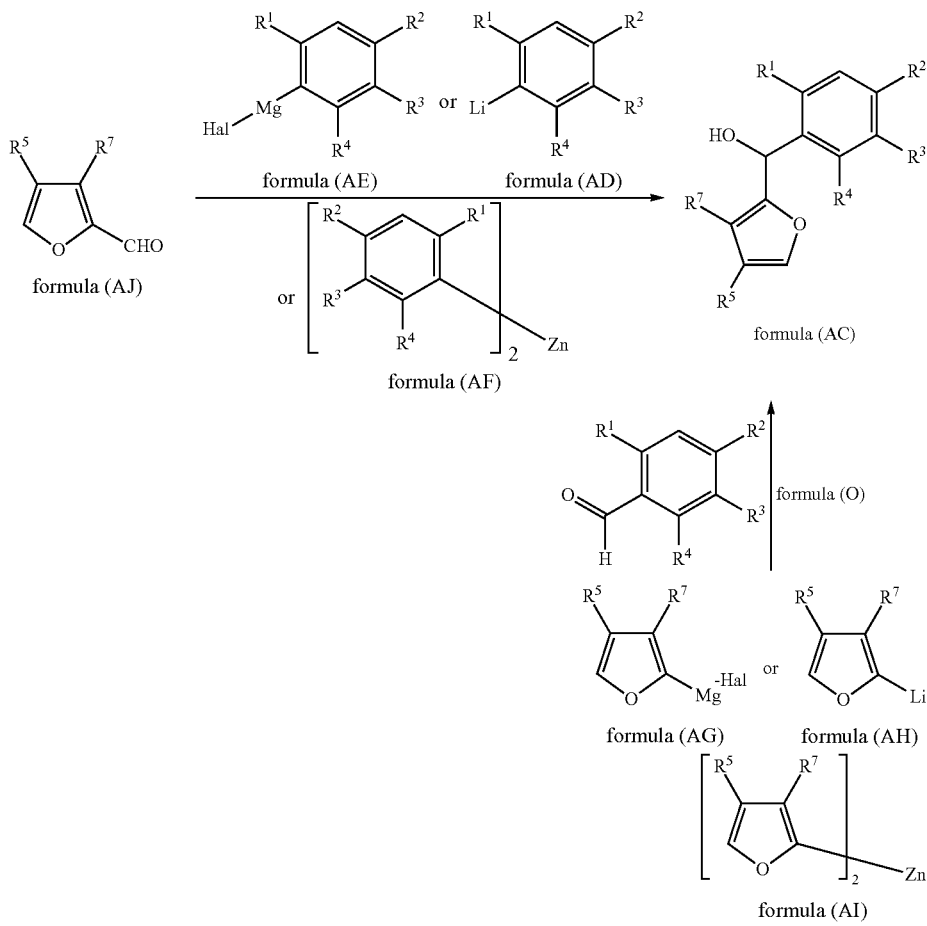

A compound of formula (G) (wherein G is hydrogen) or a compound of formula (H) (wherein G is hydrogen) can be prepared using analogous furfuryl alcohol rearrangement chemistry, starting from appropriately functionalised starting materials. Similarly, a compound of formula (L) (wherein G is hydrogen) or a compound of formula (K) (wherein G is hydrogen) can be prepared using analogous furfuryl alcohol rearrangement chemistry, starting from appropriately functionalised starting materials.

Herbicidal Compositions

In another aspect, the present invention provides a herbicidal composition, e.g. for use in a method of controlling weeds (preferably monocotyledonous such as grassy monocotyledonous weeds) in crops of useful plants, which composition comprises a compound of formula (I) as defined herein (e.g. a herbicidally effective amount thereof), and a substantially-inert agrochemically acceptable substance (e.g. an agrochemically acceptable carrier, diluent and/or solvent, an agrochemically acceptable adjuvant, an an agrochemically acceptable emulsifier/surfactant/surface-active substance, and/or another agrochemically acceptable additive).

In a further aspect, the present invention provides a herbicidal composition, e.g. for use in a method of controlling weeds (preferably monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one particular embodiment, the herbicidal composition also comprises one or more further herbicides, e.g. as mixture partner(s) for the compound of formula (I), and/or a safener. See the combinations and mixtures section herein for more details of examples of these.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agrochemically acceptable substances (e.g. an agrochemically acceptable carrier, diluent and/or solvent, an agrochemically acceptable adjuvant, an agrochemically acceptable emulsifier/surfactant/surface-active substance, and/or another agrochemically acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g.

known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate; an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2,4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol;

glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkyl-naphthalenesulfonates, such as sodium dibutylnaphthalene-sulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, anti-foams, complexing agents, neutralising or pH-modifying substances and/or buffers, corrosion-inhibitors, fragrances, wetting agents, absorption improvers, micronutrients, plasticisers, glidants, lubricants, dispersants, thickeners, anti-freezes, microbiocides, compatibility agents and/or solubilisers; and/or also liquid and/or solid fertilisers.

The herbicidal compositions (formulations) may also comprise additional active substances, for example further herbicides, herbicide safeners, plant growth regulators, fungicides or insecticides.

The herbicidal compositions according to the invention can additionally include an additive (commonly referred to as an adjuvant), comprising a mineral oil, an oil of vegetable or animal origin, alkyl (e.g. $C_1$-$C_6$alkyl) esters of such oils or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis).

Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable anionic, non-ionic, cationic or amphoteric surfactants, e.g. for this purpose, are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic surfactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBOCHARGE®, ADIGOR® (both (Syngenta Crop Protection AG), ACTIPRON® (BP Oil UK Limited), AGRI-DEXO (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, heavy aromatic hydrocarbon solvents such as SOLVESSO® or AROMATIC® solvents (Exxon Corporation). The concentration of such solvents can e.g. be from 10 to 80% by weight of the oil additive (oil adjuvant). Such oil additives (oil adjuvants), which may be in admixture with solvents, are described, for example, in U.S. Pat. No. 4,834,908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal compositions of the invention, is an emulsifiable concentrate which consists of:

(i) ethoxylated alcohols, which preferably includes ethoxylated $C_{12}$-$C_{22}$ fatty alcohols (preferably having a degree of ethoxylation of from 5 to 40); and (ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and (iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta. When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agrochemically acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agrochemically acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl)phosphate, tris-n-octyl phosphate and/or tris-[2-(n-butoxy)ethyl]phosphate, or most preferably is tris-(2-ethylhexyl)phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl(n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agrochemically acceptable substance, which preferably includes a formulation adjuvant and/or from 0 to 30% or from 0 to 25% (in particular from 0.5 to 30% or from 0.5 to 25%) by weight of a surface-active substance. Whereas herbicidal compositions (especially commercial products) will preferably be formulated as concentrates, the end user will normally employ dilute formulations (herbicidal compositions), e.g. formulations (herbicidal compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):
Emulsifiable Concentrates:
active ingredient: 0.3 to 95%, preferably 0.5 to 60% such as 1 to 40%
surface-active agents: 1 to 30%, preferably 3 to 20% such as 5 to 15%
solvents as liquid carrier: 1 to 80%, preferably 1 to 60% such as 1 to 40%
Dusts:
active ingredient: 0.1 to 10%, preferably 0.1 to 5%
solid carriers: 99.9 to 90%, preferably 99.9 to 99%
Suspension Concentrates:
active ingredient: 1 to 75%, preferably 3 to 50% or 10 to 50%
water: 98 to 24%, preferably 95 to 30% or 88 to 30%
surface-active agents: 1 to 40%, preferably 2 to 30%
Wettable Powders:
active ingredient: 0.5 to 90%, preferably 1 to 80%
surface-active agents: 0.5 to 20%, preferably 1 to 15%
solid carriers: 5 to 95%, preferably 15 to 90%
Granules:
active ingredient: 0.1 to 30%, preferably 0.1 to 15%
solid carriers: 99.5 to 70%, preferably 97 to 85%
Water-Dispersible Granules:
active ingredient: 1 to 90%, preferably 10 to 80%
surface-active agents: 0.5 to 80%, preferably 5 to 30%
solid carriers: 90 to 10%, preferably 70 to 30%

The following Examples further illustrate, but do not limit, the invention.

| F1. Emulsifiable concentrates | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture C$_9$-C$_{12}$ | 85% | 68% | 65% | 16% |

Emulsions of any desired concentration can be prepared from such concentrates by dilution with water.

| F2. Solutions | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture C$_9$-C$_{12}$ | 35% | 30% | — | — |

The solutions are suitable for application undiluted or after dilution with water.

| F3. Wettable powders | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

| F4. Coated granules | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. CaCO$_3$ or SiO$_2$ | 99.0% | 93% | 83% |

The active ingredient is dissolved in methylene chloride, the solution is sprayed onto the carrier and the solvent is subsequently evaporated off in vacuo.

| F5. Coated granules | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. CaCO$_3$ or SiO$_2$ | 98.0% | 92% | 80% |

The finely ground active ingredient is applied uniformly, in a mixer, to the carrier moistened with polyethylene glycol. Non-dusty coated granules are obtained in this manner.

| F6. Extruded granules | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

| F7. Water-dispersible granules | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

| F8. Dusts | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F9. Suspension concentrates | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (preferably monocotyledonous weeds, more preferably grassy monocotyledonous weeds) in crops of useful plants, which comprises applying a compound of the formula (I), or a herbicidal composition comprising such a compound, to the weeds and/or to the plants and/or to the locus thereof. (Preferably, in this further aspect, the herbicidal composition can be as described hereinabove or hereinbelow, e.g. as described in the "Herbicidal compositions", "Herbicidal uses", "Combinations and mixtures" and/or Claims sections hereinabove or hereinbelow.)

In a further aspect, the present invention provides a herbicidal composition, in particular for use in a method of controlling weeds (preferably monocotyledonous weeds, more preferably grassy monocotyledonous weeds) in crops of useful plants, comprising a compound of formula (I) as defined herein (e.g. a herbicidally effective amount thereof), and an agrochemically acceptable carrier, diluent and/or solvent.

In all aspects of the invention, the compound of the formula (I) is optionally present (e.g. where chemically possible) as an agrochemically acceptable salt (e.g. agrochemically acceptable metal, sulfonium or ammonium salt) thereof.

In one particular embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular, cereals (preferably non-oat cereals, in particular non-oat non-*sorghum* non-millet cereals, more particularly wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry); and/or turf and/or pastureland grass.

Preferably, in all aspects of the invention, the crops of useful plants, e.g. on or in which or at the locus of which the compounds or compositions according to the invention can be used, comprise (e.g. are): cereals (preferably non-oat cereals, more particularly non-oat non-*sorghum* non-millet cereals, even more particularly wheat, barley, rye and/or triticale), rice, sugarcane, leguminous crops (preferably soybean, peanut, and/or pulse crops, more preferably soybean), cotton, rape (in particular oilseed rape or canola), sunflower, linseed, sugarbeet, fodder beet, potato, and/or vegetables (preferably dicotyledonous vegetables).

More preferably, in all aspects of the invention, the crops of useful plants, e.g. on or in which or at the locus of which the compounds or compositions according to the invention can be used, comprise (e.g. are): wheat (e.g. winter wheat, spring wheat, or durum wheat), barley (e.g. winter or spring barley), rye, triticale, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

Most preferably, in all aspects of the invention, the crops of useful plants, e.g. on or in which or at the locus of which the compounds or compositions according to the invention can be used, comprise (e.g. are): leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, sugarbeet, fodder beet, potato and/or vegetables (preferably dicotyledonous vegetables).

The term "crops" is to be understood as also including crops that have been rendered tolerant to herbicides or classes of herbicides (for example ALS, GS, EPSPS, PPO and/or HPPD inhibitors, and/or 2,4-D or dicamba) as a result of conventional methods of breeding or genetic engineering. An example of a crop that has been rendered tolerant e.g. to imidazolinones (which are ALS inhibitors), such as imazamox, by conventional methods of breeding is Clearfield® summer rape (canola) and/or Clearfield® wheat and/or Clearfield® rice (all from BASF). Examples of crops that have been rendered tolerant to herbicides by genetic engineering methods include e.g. glyphosate- or glufosinate-resistant/tolerant maize or soybean varieties, in particular those commercially available under the trade name RoundupReady® or RoundupReady® 2 (both from Monsanto, both glyphosate-tolerant) or LibertyLink® (from Bayer, glufosinate-tolerant). Glufosinate-tolerant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy monocotyledonous) weeds, e.g. to be controlled and/or growth-inhibited, comprise (e.g. are) weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*; in particular: *Alopecurus myosuroides* (ALOMY, English name "blackgrass"), *Apera spica-venti, Avena fatua* (AVEFA, English name "wild oats"), *Avena ludoviciana, Avena sterilis, Avena sativa* (English name "oats" (volunteer)), *Brachiaria decumbens, Brachiaria plantaginea, Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria glauca, Setaria viridis* (SETVI, English name "green foxtail"), *Setaria faberi* (SETFA, English name "giant foxtail"), *Setaria lutescens* (English name "yellow foxtail"), *Sorghum bicolor* and/or *Sorghum halepense* (English name "Johnson grass"); and/or in particular: *Brachiaria platyphylla* (BRAPP), *Panicum dichotomiflorum* (PANDI), and/or *Sorghum vulgare*. Alternatively or additionally, the monocotyledonous (preferably grassy monocotyledonous) weeds, e.g. to be controlled and/or growth-inhibited, typically comprise (e.g. are) volunteer corn (volunteer maize) weeds.

In one preferred embodiment of all aspects of the invention, the monocotyledonous weeds, e.g. to be controlled and/or growth-inhibited, are grassy monocotyledonous weeds; in which case they typically comprise (e.g. are) weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*. Alternatively or additionally, the monocotyledonous (preferably grassy monocotyledonous) weeds, e.g. to be controlled and/or growth-inhibited, preferably comprise (e.g. are) volunteer corn (volunteer maize) weeds.

In one preferred embodiment of all aspects of the invention, the grassy monocotyledonous weeds, e.g. to be controlled and/or growth-inhibited, are "warm-season" (warm climate) grassy weeds; in which case they preferably comprise (e.g. are) weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*. Alternatively or additionally, the grassy monocotyledonous weeds, e.g. to be controlled and/or growth-inhibited, preferably comprise (e.g. are) volunteer corn (volunteer maize) weeds. More preferably, the grassy monocotyledonous weeds, e.g. to be controlled and/or growth-inhibited, are "warm-season" (warm climate) grassy weeds comprising (e.g. being) weeds from the genus *Brachiaria, Cenchrus, Digitaria, Echinochloa, Eleusine, Eriochloa, Panicum, Setaria* and/or *Sorghum*; and/or the grassy monocotyledonous weeds, e.g. to be controlled and/or growth-inhibited, comprise (e.g. are) volunteer corn (volunteer maize) weeds.

In another particular embodiment of all aspects of the invention, the grassy monocotyledonous weeds, e.g. to be controlled and/or growth-inhibited, are "cool-season" (cool climate) grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (e.g. *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition (2009) or 16th edition (2012), ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca,* and/or *Sorghum halapense*; or can more particularly comprise *Alopecurus myosuroides, Apera spica-venti, Avena fatua, Avena sterilis, Digitaria sanguinalis, Echinochloa colona, Echinochloa crus-galli, Lolium multiflorum, Lolium rigidum, Lolium perenne, Phalaris minor, Phalaris paradoxa, Setaria viridis, Setaria faberi* and/or *Sorghum halapense.*

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 322-324 therein in particular Table 2, incorporated herein by reference, for examples of such resistant weeds and/or amino acid substitutions); and/or (b) which are resistant to:

one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.*, 2010, 61, pp. 317-347, e.g. see Table 4 on page 328 therein, incorporated herein by reference, for examples of such resistant weeds).

In one embodiment, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola, Veronica* and/or *Xanthium.*

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agrochemically acceptable salt thereof) is generally from 1 to 2000 g of the compound of formula (I) per hectare (ha) (measured as the salt-free compound, i.e. excluding the weight of any associated salt counterion(s)), in particular from 5 to 1000 g/ha or from 5 to 500 g/ha or from 10 to 500 g/ha, preferably from 10 to 400 g/ha or from 20 to 300 g/ha, of the compound of formula (I) (measured as the salt-free compound, i.e. excluding the weight of any associated salt counterion(s)). In a preferred embodiment, the above rates of application are for post-emergence application of the compound of formula (I) (which optionally may be an agrochemically acceptable salt thereof).

In all aspects of the invention, the compound of formula (I) can be applied (typically to the weeds and/or to the crops of useful plants and/or to the locus thereof) pre- and/or post-emergence, but preferably is applied post-emergence. Other Possible Uses—e.g. Possible Insecticidal and/or Acaricidal Uses The main use and purpose of the compounds of formula (I) according to the invention is their herbicidal use. However, at least some of the compounds of formula (I) may have activity against one or more types of pest (in particular pests associated with agriculture and/or food storage). For example, at least some of the compounds of formula (I) may have at least some insecticidal, acaricidal, molluscicidal and/or nematicidal activity.

At least some of the compounds of formula (I) may have activity against (and/or may help to control and/or combat) insect pests, such as one or more of: Coleoptera, Dictyoptera, Diptera, Hemiptera (including Homoptera), Hymenoptera, Isoptera, Lepidoptera, Orthoptera, Siphonaptera and/or Thysanoptera.

At least some of the compounds of formula (I) may have activity against (and/or may help to control and/or combat) acarine pests and/or pests from the order Acarina, such as one or more of: *Acalitus* spp, *Aculus* spp, *Acaricalus* spp, *Aceria* spp, *Acarus* siro, *Amblyomma* spp., *Argas* spp., *Boophilus* spp., *Brevipalpus* spp., *Bryobia* spp, *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora, Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and/or *Tetranychus* spp.

At least some of the compounds of formula (I) may have activity against (and/or may help to control and/or combat) other (i.e. non-insect, non-acarine) invertebrate pests, for example, nematode and/or mollusc pests.

Insects, acarines, nematodes and/or molluscs are hereinafter collectively referred to as pests.

Examples of pest species, on and/or to which the compounds of formula (I) can be tried and/or applied, include one or more of: *Myzus* spp. such as *Myzus persicae* (aphid), *Aphis* spp. such as *Aphis gossypii* (aphid) or *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus* spp. such as *Tetranychus urticae* (two-spotted spider mite) or *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides fells* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), of the Kalotermitidae (for example *Neotermes* spp.), of the Rhinotermitidae (for example *Coptotermes formosanus, Reticulitermes flavipes, R. speratu, R. virginicus, R. hesperus,* or *R. santonensis*) or of the Termitidae (for example *Globitermes sulphureus*), *Solenopsis geminata* (fire ant), *Monomorium pharaonis* (pharaoh's ant), *Damalinia* spp. or *Linognathus* spp. (biting lice or sucking lice), *Meloidogyne* spp. (root knot nematodes), *Globodera* spp. or *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans*_(vinegar eelworm), *Trichostrongylus* spp. (gastro intestinal nematodes) and/or *Deroceras reticulatum* (slug).

Combinations and Mixtures

In a further aspect, the present invention provides a herbicidal composition, e.g. for use in a method of controlling weeds (in particular monocotyledonous such as grassy monocotyledonous weeds) in crops of useful plants, comprising a compound of formula (I) as defined herein (e.g. a herbicidally effective amount thereof), and an agrochemically acceptable carrier, diluent and/or solvent, and also comprising one or more further herbicides, and/or a safener.

In all aspects of the invention, the compound of the formula (I) is optionally present (e.g. where chemically possible) as an agrochemically acceptable salt (e.g. agrochemically acceptable metal, sulfonium or ammonium salt) thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of the specific compounds disclosed herein e.g. hereinbelow (in particular, any of compounds A1 to A29, or A30 to A41, or A42 or A45, or any of the compounds disclosed in any of Tables 1 to 60), present either as a free compound and/or as an agrochemically acceptable salt thereof.

In particular, the following mixtures of the compound of formula (I) with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chloroflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate (see e.g. US2012/0184434A1), compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl-]bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl[(1RS)-1-(2,4-dichlorophenoxyacetoxy)ethyl]phosphonate, also named lvxiancaolin or lüxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6).

The mixture partners for the compound of formula (I) are optionally in the form of an ester (in particular an agrochemically acceptable ester) or a salt (in particular an agrochemically acceptable salt) thereof (e.g. where chemically possible). The above-mentioned mixture partners for the compound of formula (I), are generally mentioned e.g. in The Pesticide Manual, 15th Edition (2009) or 16th edition (2012), ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl] methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula I+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (Dow, e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (Dow, e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference), compound of formula (I)+one of the specific herbicidal compounds disclosed in WO 2010/059671 (Dow, e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6);

wherein the mixture partners for the compound of formula (I) may optionally be in the form of an ester (in particular an agrochemically acceptable ester) or a salt (in particular an agrochemically acceptable salt) thereof (e.g. where chemically possible).

For applications in soybean, the following mixtures are preferred:

compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula (I)+a choline salt of 2,4-D+glyphosate (see e.g. Examples 2 and 3 of WO2010/123871A1) (especially for applications to 2,4-D-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (see e.g. US2012/0184434A1) (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate (especially for applications to glufosinate-tolerant soybean, e.g. genetically-modified), compound of formula (I)+glufosinate-ammonium (especially for applications to glufosinate-tolerant soybean, e.g. genetically-modified), compound of formula (I)+glyphosate (especially for applications to glyphosate-tolerant soybean, e.g. genetically-modified), compound of formula (I)+glyphosate-diammonium (especially for applications to glyphosate-tolerant soybean, e.g. genetically-modified), compound of formula (I)+glyphosate-isopropylammonium (especially for applications to glyphosate-tolerant soybean, e.g. genetically-modified), compound of formula (I)+glyphosate-potassium (especially for applications to glyphosate-tolerant soybean, e.g. genetically-modified), compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9 (Syngenta Limited), and which is also compound A-13 disclosed in pages 4, 5, 7 and 11 of WO 2011/073616 A2 (Syngenta Limited), these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9 (Syngenta Limited), and which is also compound A-12 disclosed in page 10 of WO 2011/073616 A2 (Syngenta Limited), these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1 (Syngenta Participations AG and Syngenta Limited), and which is also compound A-4 disclosed on page 7 of WO 2011/073615 A2 (Syngenta Limited), these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1 (Syngenta Participations AG and Syngenta Limited), and which is also the compound of Example P10 disclosed on pages 41 and 45 of WO 2010/136431 A9 (Syngenta Limited), and which is also compound A-7 disclosed on page 7 of WO 2011/073615 A2 (Syngenta Limited), these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1 (Syngenta Participations AG and Syngenta Limited), and which is also compound A-9 disclosed on page 8 of WO 2011/073615 A2 (Syngenta Limited), these parts of these publications being incorporated herein by reference);

wherein the mixture partners for the compound of formula (I) may optionally be in the form of an ester (in particular an agrochemically acceptable ester) or a salt (in particular an agrochemically acceptable salt) thereof (e.g. where chemically possible).

In the above-mentioned compositions or mixtures comprising a compound of formula (I) (in particular, one of the specific compounds disclosed herein, e.g. any of compounds A1 to A29, or A30 to A41, or A42 or A45, or any of the compounds disclosed in any of Tables 1 to 60, present either as a free compound and/or as an agrochemically acceptable salt thereof) and one or more further herbicides, the weight ratio of the compound of formula (I) to each further herbicide can vary over a large range and is, typically, from 300:1 to 1:500, especially from 150:1 to 1:200, more especially from 100:1 to 1:100, even more especially from 30:1 to 1:30. Typically, these weight ratios are measured as the free compound(s), i.e. excluding the weight of any associated salt counterion(s).

Alternatively or additionally, in herbicidal compositions, the compounds of formula I according to the invention can also be used in combination with a safener. Preferably, in these mixtures, the compound of the formula I is one of the specific compounds disclosed herein e.g. hereinbelow (in particular, any of compounds A1 to A29, or A30 to A41, or A42 or A45, or any of the compounds disclosed in any of Tables 1 to 60), present either as a free compound and/or as an agrochemically acceptable salt thereof. The following mixtures with safeners, especially, come into consideration:

compound of formula I+cloquintocet-mexyl, compound of formula I+cloquintocet acid or an agrochemically acceptable salt thereof, compound of formula I+fenchlorazole-ethyl, compound of formula I+fenchlorazole acid or an agrochemically acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

The above-mentioned safeners and herbicides are described, for example, in the Pesticide Manual, 14th Edition, British Crop Production Council, 2006; or The Pesticide Manual 15$^{th}$ edition (2009) or 16th edition (2012), ed. C. D. S. Tomlin, British Crop Production Council. R-29148 is described, for example by P. B. Goldsbrough et al., *Plant Physiology*, (2002), Vol. 130 pp. 1497-1505 and references therein. PPG-1292 is known from WO 2009/211761. N-(2-methoxybenzoyl)-4-[(methylaminocarbonyl)amino]benzenesulfonamide is known from e.g. EP365484.

Especially preferably, in a composition or mixture comprising a compound of formula (I) (in particular, one of the specific compounds disclosed herein, e.g. any of compounds A1 to A29, or A-30 to A-41, or A42 or A45, or any of the compounds disclosed in any of Tables 1 to 60, present either as a free compound and/or as an agrochemically acceptable salt thereof) and a safener, the safener comprises (e.g. is) benoxacor, cloquintocet-mexyl, cloquintocet acid or an agrochemically acceptable salt thereof, cyprosulfamide, mefenpyr-diethyl, isoxadifen-ethyl and/or N-(2-methoxybenzoyl)-4-[(methylaminocarbonyl)amino]-benzenesulfonamide. Even more preferably, the safener comprises (e.g. is) cloquintocet-mexyl, cloquintocet acid or an agrochemically acceptable salt thereof, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

In the above-mentioned compositions or mixtures comprising a compound of formula (I) (in particular, one of the specific compounds disclosed herein, e.g. any of compounds A1 to A29, or A-30 to A-41, or A42 or A45, or any of the compounds disclosed in any of Tables 1 to 60, present either as a free compound and/or as an agrochemically acceptable salt thereof) with a safener, the weight ratio of the compound of formula (I) to the safener can vary over a large range and is, typically, from 200:1 to 1:200, especially from 50:1 to 1:50, more especially from 20:1 to 1:20, even more especially from 20:1 to 1:10. Preferably, the safener comprises (e.g. is) cloquintocet-mexyl, cloquintocet acid or an agrochemically acceptable salt thereof, mefenpyr-diethyl and/or isoxadifen-ethyl, and the weight ratio of the compound of formula (I) to the safener is from 20:1 to 1:10, more preferably from 15:1 to 1:2 (this can be, for example, for use on non-oat cereals). Typically, these weight ratios are measured as the free compound(s), i.e. excluding the weight of any associated salt counterion(s).

Application rates of herbicide (e.g. compound of formula (I)) and/or safener: The rate of application of safener relative to the compound of formula (I) is largely dependent upon the mode of application. In the case of field and/or soil and/or plant treatment (e.g. in a field or glasshouse): for example from 0.5 to 1000 g of safener per ha, or preferably from 1 to 250 g or from 2 to 200 g of safener per ha, are applied; and/or generally from 1 to 2000 g of compound of formula (I) per ha, or preferably from 5 to 500 g or from 10 to 400 g of compound of formula (I) per ha, are applied. ha=hectare. Typically, these application rates are measured as the free compound, i.e. excluding the weight of any associated salt counterion(s). In field and/or plant treatment, the application of the compound of formula (I) is preferably post-emergence.

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. Ha=hectare. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

In one particular embodiment, the herbicidal composition or mixture comprising the compound of formula (I) and one or more further herbicides (e.g. as mentioned hereinabove) can be applied together with one of the safeners mentioned herein, e.g. hereinabove.

In a further aspect, the present invention provides a herbicidal composition, e.g. for use in a method of controlling weeds (in particular monocotyledonous such as grassy monocotyledonous weeds) in crops of useful plants, comprising a compound of formula (I) as defined herein (in particular, one of the specific compounds disclosed herein, e.g. any of compounds A1 to A29, or A30 to A41, or A42 or A45, or any of the compounds disclosed in any of Tables 1 to 60, present either as a free compound and/or as an agrochemically acceptable salt thereof) (e.g. a herbicidally effective amount thereof), and an agrochemically acceptable carrier, diluent and/or solvent, and also comprising a plant growth regulator, and optionally one or more further herbicides (e.g. as described herein, e.g. glyphosate and/or dicamba and/or 2,4-D) and optionally a safener (e.g. as described herein).

Preferably, the plant growth regulator is: abscisic acid, acibenzolar-S-methyl, a brassinosteroid plant growth regulator, 24-epi brassinolide, 28-homobrassinolide, chlormequat, a cytokinin plant growth regulator, ethephon, ethylene, flurprimidol, gibberellic acid, a gibberellin plant growth regulator (in particular gibberellin A3, gibberellin A4, or gibberellin A7, or gibberellin A4 and gibberellin A7), GR24, indole-3-acetic acid (IAA), indole-3-butyric acid (IBA), jasmonic acid, methyl jasmonate, a karrikin plant growth regulator, maleic hydrazide, mefluidide, mepiquat, methylcyclopropene such as 1-methylcyclopropene, 1-naphthaleneacetic acid (NAA), paclobutrazol, prohexadione, prohexadione-calcium, salicylic acid, a strigolactone plant growth regulator (such as strigol or orobanchol or a derivative of one of these, or the synthetic strigolactone GR-24) (see e.g. K. Yoneyma et al, "Strigolactones as a new plant growth regulator", http://www.niaes.affrc.go.jp/marco/marco2009/english/program/W3-04_Yoneyama-_Koichi.pdf), trinexapac-ethyl and/or uniconzole, or an agrochemically acceptable salt e.g. acid addition salt or metal or ammonium salt e.g. alkali metal salt of any of these. More preferably, the plant growth regulator is: gibberellic acid, or a gibberellin plant growth regulator (in particular gibberellin A3, gibberellin A4, or gibberellin A7, or gibberellin A4 and gibberellin A7), or an agrochemically acceptable salt e.g. metal or ammonium salt e.g. alkali metal salt of any of these. Most preferably, the plant growth regulator is gibberellic acid or an agrochemically acceptable salt e.g. metal or ammonium salt e.g. alkali metal salt thereof. Gibberellic acid is preferred because WO 2014/071110 A1 (Valent USA Corp.) discloses that gibberelic acid, when mixed with clethodim, increased clethodim's control and/or speed of control of Johnsongrass (Sorghum halepense) and volunteer corn; and increased the control of glyphosate-tolerant (Roundup-Ready™) volunteer corn at 21 days after the application of a mixture of clethodim+dicamba-glycolamine+glyphosate+gibberellic acid (compared to clethodim+dicamba-glycolamine+glyphosate+ammonium sulfate).

In the above-mentioned herbicidal compositions comprising a compound of formula (I), an agrochemically acceptable carrier, diluent and/or solvent, and a plant growth regulator (e.g. gibberellic acid or a salt thereof), and optionally one or more further herbicides and optionally a safener, the weight ratio of the compound of formula (I) to the plant growth regulator (e.g. gibberellic acid or an agrochemically acceptable salt e.g. metal salt e.g. alkali metal salt thereof) can vary over a large range and is, typically, from 500:1 to 1:500, especially from 200:1 to 1:200, more especially from 100:1 to 1:100, even more especially from 30:1 to 1:30. Typically, these weight ratios are measured as the free compound(s), i.e. excluding the weight of any associated salt counterion(s).

The following Examples illustrate the invention further but do not limit the invention.

PREPARATION EXAMPLES

Those skilled in the art will appreciate that certain compounds described below are β-ketoenols (beta-ketoenols), and as such may exist as a single tautomer or as a mixture of keto-enol and diketone tautomers, as described, for example by J. March, Advanced Organic Chemistry, third edition, John Wiley and Sons. The compounds shown below, and in Table T1 herein, are generally drawn as an arbitrary single enol tautomer, but it should be inferred that this description covers both the diketone form and any possible enols which could arise through tautomerism. Where more than one tautomer is observed in proton NMR NMR), the data shown are for the mixture of tautomers. Furthermore, some of the compounds shown below have the possibility of being present in at least two enantiomeric forms; unless drawn as single enantiomers, these compounds will usually be present as a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

Typical Abbreviations

DCM—dichloromethane
DMF—N,N-dimethylformamide
LDA—lithium diisopropylamide
THF—tetrahydrofuran
RT—room temperature (typically ca. 15-30° C. such as ca. 18-25° C.)
NMR—nuclear magnetic resonance Intermediate 1—Preparation of 3-methoxy-2-(2,4,6-trimethylphenyl)-cyclopent-2-en-1-one (Previously Described as Example 1 Step 1 on Pages 54-55 of WO 2010/000773 A1)

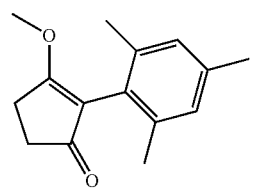

To a suspension of 2-bromo-3-methoxy-cyclopent-2-en-1-one (6.75 g, 35.3 mmol), 2,4,6-trimethylphenyl boronic acid (6.99 g, 42.6 mmol) and freshly ground potassium phosphate (15 g, 70.6 mmol) in degassed toluene (180 ml) under nitrogen are added Pd(OAc)$_2$ (159 mg, 0.71 mmol) and S-Phos (2-(dicyclohexylphosphino)-2',6'-dimethoxybiphenyl) (579 mg, 1.41 mmol), and the reaction heated to 90° C. with stirring under nitrogen for 4 hours. The reaction mixture is partitioned between ethyl acetate (150 ml) and water (150 ml), and the organic layer is removed, silica gel is added to the organic layer, the solvent is evaporated under reduced pressure and the residue is purified by flash chromatography on silica gel to give 3-methoxy-2-(2,4,6-trimethylphenyl)-cyclopent-2-en-1-one (6.2 g).

Intermediate 2: Preparation of 2-(4-Bromo-2,6-dimethyl-phenyl)-3-methoxy-cyclopent-2-en-1-one

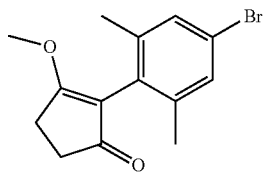 [SMILES: COC1=C(c2c(C)cc(Br)cc2C)C(=O)CC1]

Step 1: Preparation of ([4-bromo-2,6-dimethylphenyl]furan-2-yl)methanol (Previously Described in Example 1 Step 1 on Pages 51-52 of WO 2010/089210 A1)

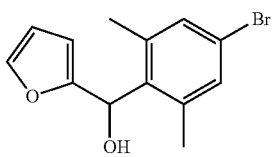 [SMILES: Cc1cc(Br)cc(C)c1C(O)c1ccco1]

4-Bromo-2,6-dimethyl-1-iodobenzene (5 g, 16 mmol) is dissolved in dry tetrahydrofuran (20 ml) and cooled to −78° C. under an atmosphere of dry nitrogen. Isopropylmagnesium chloride (2M solution in tetrahydrofuran, 10 ml, 20 mmol) is added dropwise with vigorous stirring over 30 minutes. When the addition is complete, the reaction is allowed to warm to room temperature and is stirred for 30 minutes at room temperature. The reaction mixture is cooled to −78° C. and a solution of 2-furaldehyde (2.4 g, 25 mmol) in dry tetrahydrofuran (10 ml) is added dropwise over 30 minutes. Once the addition is complete, the mixture is allowed to warm to room temperature and stirring continued for 2 hours. A solution of saturated aqueous ammonium chloride (30 ml) is added, and the mixture is extracted with dichloromethane (3×25 ml). The organic extracts are combined, washed with brine, dried over anhydrous magnesium sulfate, filtered and the filtrate is evaporated under reduced pressure. The residue is purified by column chromatography on silica gel to give ([4-bromo-2,6-dimethylphenyl]furan-2-yl)methanol (3.71 g).

Step 2: Preparation of 5-(4-bromo-2,6-dimethylphenyl)-4-hydroxycyclopent-2-enone (Previously Described in Example 1 Step 2 on Page 52 of WO 2010/089210 A1)

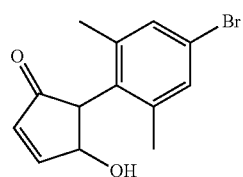 [SMILES: Cc1cc(Br)cc(C)c1C1C(=O)C=CC1O]

Polyphosphoric acid (500 mg) is added to a warm (55° C.) solution of ([4-bromo-2,6-dimethylphenyl]furan-2-yl)methanol (843 mg, 3 mmol) in acetone (8 ml) and water (2 ml) and the mixture is heated at 55° C. for 24 hours. The mixture is cooled to room temperature and the acetone is removed under reduced pressure. The remaining mixture is partitioned between diethyl ether (20 ml) and water (20 ml). The aqueous phase is extracted with ether (2×50 ml), and then the organic phases are combined, washed with saturated aqueous sodium bicarbonate solution (20 ml), and brine (20 ml), dried over anhydrous magnesium sulfate, filtered and the filtrate is evaporated under reduced pressure. The residue is purified by column chromatography on silica gel to give 5-(4-bromo-2,6-dimethylphenyl)-4-hydroxycyclopent-2-enone (596 mg).

Step 3: Preparation of 2-(4-bromo-2,6-dimethylphenyl)cyclopent-4-ene-1,3-dione (Previously Described in Example 1 Step 3 on Page 52 of WO 2010/089210 A1)

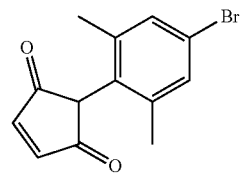 [SMILES: Cc1cc(Br)cc(C)c1C1C(=O)C=CC1=O]

To a solution of 5-(4-bromo-2,6-dimethylphenyl)-4-hydroxycyclopent-2-enone (18.33 g. 65 mmol) in acetone (200 ml) at 0° C. is added, dropwise, a solution of Jones reagent (1.67 M, 39 ml, 65 mmol) and the resulting yellow solution is stirred at 0° C. for 90 minutes. The reaction is quenched by the addition of propan-2-ol (1 ml) and stirred for a further 2 hours. Brine (300 ml) is added and the reaction is extracted with ethyl acetate (3×250 ml). The organic extracts are combined, washed with brine, dried over anhydrous magnesium sulfate, filtered and the filtrate is concentrated under reduced pressure. The residue is purified by column chromatography on silica gel to give 2-(4-bromo-2,6-dimethylphenyl)cyclopent-4-ene-1,3-dione (17.2 g).

Step 4: Preparation of 2-(4-Bromo-2,6-dimethyl-phenyl)cyclopentane-1,3-dione

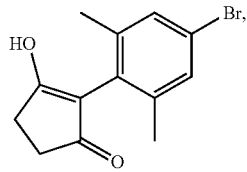 [SMILES: Cc1cc(Br)cc(C)c1C1=C(O)CCC1=O]

also present as

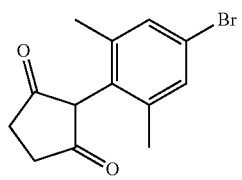 [SMILES: Cc1cc(Br)cc(C)c1C1C(=O)CCC1=O]

To a solution of 2-(4-bromo-2,6-dimethylphenyl)cyclopent-4-ene-1,3-dione (50 g, 0.18 mol) in acetic acid (2000 ml) at 25-30° C. is added zinc powder (82.3 g, 1.26 mol). The resulting suspension is heated to 90° C. for 2 hours, followed by cooling to room temperature then filtration through a bed of diatomaceous earth. The residue is washed with methanol (100 ml×2) and the solution is concentrated in vacuo. Distilled water is added and the crude product is extracted with ethyl acetate (500 ml×3). Organic fractions are combined then washed with distilled water, brine, then dried over sodium sulfate, filtered and the filtrate is concentrated in vacuo to afford 2-(4-bromo-2,6-dimethylphenyl)cyclopentane-1,3-dione. This material is used directly in the next step without further purification.

Step 5: Preparation of 2-(4-Bromo-2,6-dimethyl-phenyl)-3-methoxy-cyclopent-2-en-1-one

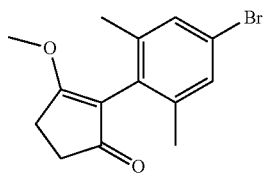 [SMILES: COC1=C(c2c(C)cc(Br)cc2C)C(=O)CC1]

To a solution of 2-(4-bromo-2,6-dimethylphenyl)cyclopentane-1,3-dione (40 g, 0.143 mol) in acetone (2000 ml) is added anhydrous potassium carbonate (98.5 g, 0.714 mol) and iodomethane (45 ml, 0.72 mol). The resulting mixture is stirred at 25-30° C. for 16 hours, then volatile solvents are removed in vacuo, and the residue is diluted with distilled water (200 ml) and extracted with ethyl acetate (3×500 ml). Organic fractions are combined, washed with distilled water, brine, then dried over sodium sulphate, filtered and the filtrate concentrated in vacuo. The crude product is purified by flash column chromatography to afford 2-(4-bromo-2,6-dimethyl-phenyl)-3-methoxy-cyclopent-2-en-1-one.

Intermediate 3: 2-(2,6-diethyl-4-methylphenyl)-3-methoxy-cyclopent-2-en-1-one (Previously Disclosed in Example 2, Pages 54-55 of WO2009/019005A2 (Syngenta Limited))

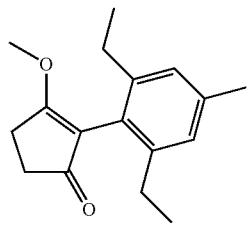

Step 1: Preparation of 2-bromo-3-methoxy-cyclopent-2-en-1-one

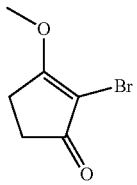

N-Bromosuccinimide (24.92 g, 0.140 mol) is added, portionwise, over 1 hour to a stirred solution of 3-methoxy-cyclopent-2-enone (14.95 g, 0.133 mol) in 1,2-dichloroethane (300 ml) at 0° C. in an amber flask. The reaction mixture is stirred at 0° C. for a further 90 minutes and then any remaining solid is removed by filtration. The filtrate is evaporated to dryness under reduced pressure, the resultant solid is dissolved in warm toluene (600 ml) and washed quickly with ice-cold water (2×100 ml). The organic phase is dried over anhydrous magnesium sulfate, filtered and the filtrate evaporated under reduced pressure until approximately 150 ml remains. The residue is cooled with an ice bath and left for 30 minutes. The resultant solid is removed by filtration, washed with hexane (50 ml) and air-dried to give 2-bromo-3-methoxy-cyclopent-2-en-1-one.

Step 2: Preparation of 2-(2,6-diethyl-4-methylphenyl)-3-methoxy-cyclopent-2-en-1-one

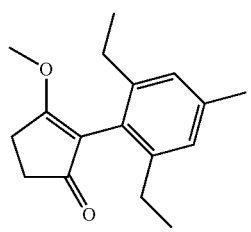

To a stirred suspension of 2-bromo-3-methoxy-cyclopent-2-en-1-one (17.5 g, 91.6 mmol), 2,6-diethyl-4-methylphenyl boronic acid (26.4 g, 137 mmol) and freshly powdered potassium phosphate (38.9 g, 183 mmol) in anhydrous, degassed toluene (450 ml) under a nitrogen atmosphere are added palladium (II) acetate (0.411 g, 1.83 mmol) and 2-dicyclohexylphosphino-2',6'-dimethoxybiphenyl (1.51 g, 3.67 mmol). The reaction mixture is heated at 90° C. for 6.5 hours and then allowed to cool to room temperature overnight. The reaction is diluted with water (400 ml) and extracted with ethyl acetate (3×150 ml). The combined organic extracts are washed with brine (50 ml), dried over anhydrous magnesium sulfate, filtered and the filtrate is evaporated to dryness under reduced pressure to give a brown oil. The crude product is purified by column chromatography on silica gel to give 2-(2,6-diethyl-4-methylphenyl)-3-methoxy-cyclopent-2-en-1-one.

Example 1: Preparation of 2-[4-(5-chloropyrimidin-2-yl)-2,6-dimethylphenyl]-4-prop-2-ynylcyclopentane-1,3-dione

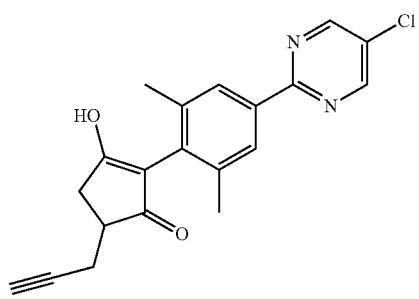 [SMILES: C#CCC1CC(O)=C(c2c(C)cc(-c3ncc(Cl)cn3)cc2C)C1=O]

Step 1: Preparation of 2-[2,6-dimethyl-4-(4,4,5,5-tetramethyl-1,3,2-dioxaborolan-2-yl)phenyl]-3-methoxycyclopent-2-en-1-one

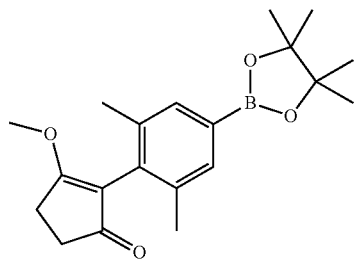

To a mixture of 2-(4-bromo-2,6-dimethylphenyl)-3-methoxycyclopent-2-en-1-one (described in WO 2011073060) (10.0 g, 33.9 mmol), 4,4,5,5-tetramethyl-2-(4,4,5,5-tetramethyl-1,3,2-dioxaborolan-2-yl)-1,3,2-dioxaborolane (13.0 g, 50.8 mmol), tris(dibenzylideneacetone)dipalladium(0) (1.24 g, 1.36 mmol), potassium acetate (4.99 g, 50.8 mmol) and 2-dicyclohexylphosphino-2',6'-dimethoxybiphenyl (2.29 g, 5.42 mmol) under nitrogen was added anhydrous 1,4-dioxane (150 ml). The resulting mixture was heated at 80° C. for 3 hour 15 minutes, then cooled to room temperature and poured into distilled water (150 ml). After dilution with ethyl acetate (150 ml) the phases were separated and the aqueous phase was extracted with further ethyl acetate (120 ml). The combined organic phases were washed with distilled water, brine, dried over anhydrous magnesium sulphate, filtered through diatomaceous earth and concentrated in vacuo. The crude product was triturated with isohexane to afford 2-[2,6-dimethyl-4-(4,4,5,5-tetramethyl-1,3,2-dioxaborolan-2-yl)phenyl]-3-methoxycyclopent-2-en-1-one.

Step 2: Preparation of 2-[2,6-dimethyl-4-(4,4,5,5-tetramethyl-1,3,2-dioxaborolan-2-yl)phenyl]-3-methoxy-5-prop-2-ynylcyclopent-2-en-1-one

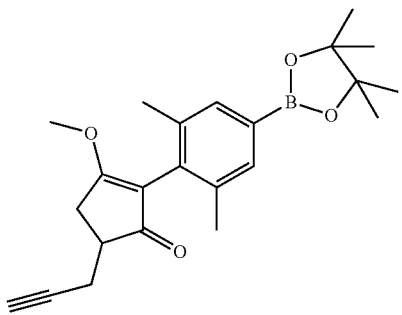 [SMILES: C#CCC1CC(OC)=C(c2c(C)cc(B3OC(C)(C)C(C)(C)O3)cc2C)C1=O]

To a solution of 2-[2,6-dimethyl-4-(4,4,5,5-tetramethyl-1,3,2-dioxaborolan-2-yl)phenyl]-3-methoxycyclopent-2-en-1-one (0.50 g, 1.46 mmol) in anhydrous tetrahydrofuran (10 ml) under nitrogen at −78° C. was added a solution of lithium diisopropylamide (1.30 ml, 2.34 mmol, 1.8M solution in a mixture of tetrahydrofuran, heptane and ethylbenzene) dropwise. The solution was stirred at −78° C. for 45 minutes, after which a second solution of 3-bromoprop-1-yne (0.195 ml, 1.75 mmol, 80 wt % in toluene) in tetrahydrofuran (1 ml) was added dropwise. The reaction was stirred at −78° C. for a further 1 hour then allowed to warm to room temperature overnight. The reaction mixture was quenched with aqueous ammonium chloride (10 ml) then further diluted with ethyl acetate (10 ml) and distilled water (2 ml). The phases were separated and the aqueous phase was additionally extracted with ethyl acetate (×2). The combined organic phases were washed with brine, dried over magnesium sulphate and filtered. The filtrate was concentrated in vacuo. The crude product was purified by flash column chromatography on silica to afford 2-[2,6-dimethyl-4-(4,4,5,5-tetramethyl-1,3,2-dioxaborolan-2-yl)phenyl]-3-methoxy-5-prop-2-ynylcyclopent-2-en-1-one as a pale yellow solid.

Step 3: Preparation of 2-[4-(5-chloropyrimidin-2-yl)-2,6-dimethylphenyl]-3-methoxy-5-prop-2-ynylcyclopent-2-en-1-one

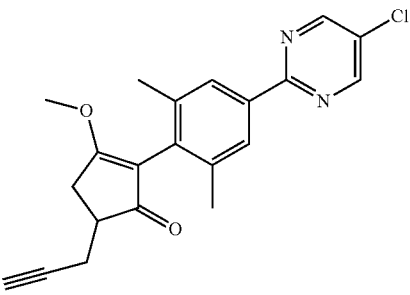 [SMILES: C#CCC1CC(OC)=C(c2c(C)cc(-c3ncc(Cl)cn3)cc2C)C1=O]

To a mixture of 2-[2,6-dimethyl-4-(4,4,5,5-tetramethyl-1,3,2-dioxaborolan-2-yl)phenyl]-3-methoxy-5-prop-2-ynylcyclopent-2-en-1-one (0.225 g, 0.59 mmol), 2-bromo-5-chloro-pyrimidine (0.17 g, 0.88 mmol) and tetrakis(triphenylphosphine)palladium(0) (0.014 g, 0.012 mmol) under nitrogen was added 1,2-dimethoxyethane (4 ml) followed by stirring at room temperature for 30 minutes. After this time an aqueous solution of potassium carbonate (0.165 g, 1.183 mmol) in water (1.0 ml) was added and the mixture was heated at 130° C. for 40 minutes under microwave irradiation. The reaction mixture was poured into distilled water and diluted with ethyl acetate. The phases were separated and the aqueous phase was extracted with ethyl acetate (×2). The combined organic phases were dried over magnesium sulfate, filtered and the filtrate concentrated in vacuo to afford crude 2-[4-(5-chloropyrimidin-2-yl)-2,6-dimethylphenyl]-3-methoxy-5-prop-2-ynylcyclopent-2-en-1-one.

Step 4: Preparation of 2-[4-(5-chloropyrimidin-2-yl)-2,6-dimethylphenyl]-4-prop-2-ynylcyclopentane-1,3-dione

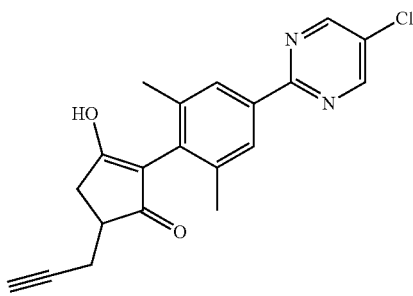 [SMILES: C#CCC1CC(O)=C(c2c(C)cc(-c3ncc(Cl)cn3)cc2C)C1=O]

To a solution of 2-[4-(5-chloropyrimidin-2-yl)-2,6-dimethylphenyl]-3-methoxy-5-prop-2-ynylcyclopent-2-en-1-one (414 mg, 1.13 mmol) in acetone (3 ml) was added 2M aqueous hydrochloric acid (2 ml). The mixture was heated at 80° C. for 30 minutes under microwave irradiation then left to stand at room temperature overnight. The reaction mixture was diluted in dichloromethane and distilled water, then filtered through diatomaceous earth followed by further washing with dichloromethane. The phases were separated and the organic phase was concentrated in vacuo to afford a crude product which was purified by preparative reverse phase HPLC to afford 2-[4-(5-chloropyrimidin-2-yl)-2,6-dimethylphenyl]-4-prop-2-ynylcyclopentane-1,3-dione.

Example 2: Preparation of 2-[2-chloro-4-(4-chlorophenyl)-6-methoxyphenyl]-4-prop-2-ynylcyclopentane-1,3-dione

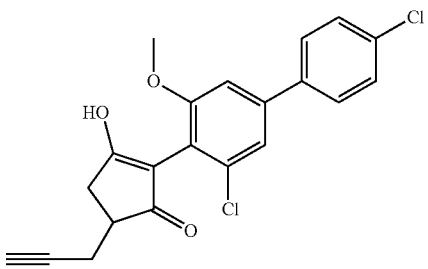 [SMILES: C#CCC1CC(O)=C(c2c(Cl)cc(-c3ccc(Cl)cc3)cc2OC)C1=O]

Step 1: Preparation of 2-[2-chloro-6-methoxy-4-(4,4,5,5-tetramethyl-1,3,2-dioxaborolan-2-yl)phenyl]-3-methoxycyclopent-2-en-1-one

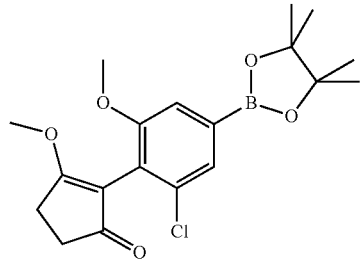

To a mixture of 2-(2-chloro-6-methoxyphenyl)-3-methoxycyclopent-2-en-1-one (2.87 g, 11.4 mmol), 4,4,5,5-tetramethyl-2-(4,4,5,5-tetramethyl-1,3,2-dioxaborolan-2-yl)-1,3,2-dioxaborolane (3.46 g, 13.6 mmol), (1,5-cyclooctadiene)(methoxy)iridium(I) dimer (0.339 g, 0.511 mmol) and 4,4'-di-tert-butyl bipyridine (0.280 g, 1.02 mmol) under nitrogen was added tert-butyl methyl ether (12 ml). The resulting solution was heated to 80° C. for 5 hours, then allowed to stand at room temperature overnight. The reaction mixture was concentrated in vacuo then purified by flash column chromatography on silica to afford 2-[2-chloro-6-methoxy-4-(4,4,5,5-tetramethyl-1,3,2-dioxaborolan-2-yl)phenyl]-3-methoxycyclopent-2-en-1-one.

Step 2: Preparation of 2-[2-chloro-4-(4-chlorophenyl)-6-methoxyphenyl]-3-methoxy-cyclopent-2-en-1-one

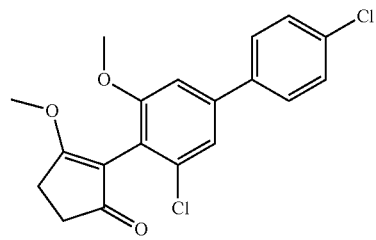 [SMILES: COC1=C(c2c(Cl)cc(-c3ccc(Cl)cc3)cc2OC)C(=O)CC1]

To a mixture of 2-[2-chloro-6-methoxy-4-(4,4,5,5-tetramethyl-1,3,2-dioxaborolan-2-yl)phenyl]-3-methoxycyclopent-2-en-1-one (0.25 g, 0.66 mmol), 1-bromo-4-chlorobenzene (0.19 g, 0.99 mmol) and 1,1'-bis(diphenylphosphino)ferrocene palladium(II)dichloride dichloromethane (0.055 g, 0.066 mmol) under nitrogen was added degassed dimethoxyethane (2.5 ml) followed by a solution of tripotassium phosphate (1.40 ml, 2.64 mmol, 40% solution in distilled water). The reaction mixture was heated at 85° C. for 3 hours then left to stand at room temperature overnight. The reaction mixture was poured into distilled water, diluted with ethyl acetate and acidified with 2M aqueous hydrochloric acid. The reaction mixture was filtered through diatomaceous earth (washing with more ethyl acetate), the phases were separated and the organic phase was concentrated in vacuo. The crude product was purified by flash column chromatography on silica to afford 2-[2-chloro-4-(4-chlorophenyl)-6-methoxyphenyl]-3-methoxycyclopent-2-en-1-one.

Step 3: Preparation of 2-[2-chloro-4-(4-chlorophenyl)-6-methoxyphenyl]-3-methoxy-5-prop-2-ynylcyclopent-2-en-1-one

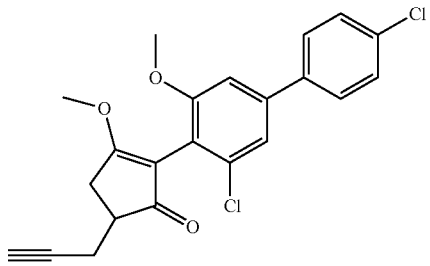 [SMILES: C#CCC1CC(OC)=C(c2c(Cl)cc(-c3ccc(Cl)cc3)cc2OC)C1=O]

To a solution of 2-[2-chloro-4-(4-chlorophenyl)-6-methoxyphenyl]-3-methoxy-cyclopent-2-en-1-one (0.117 g, 0.322 mmol) in anhydrous tetrahydrofuran (3 ml) under nitrogen at −78° C. was added potassium bis(trimethylsilyl)amide (0.38 ml, 0.38 mmol, 1M solution in tetrahydrofuran) dropwise, and the reaction was allowed to stir at this temperature for 65 minutes. A solution of 3-bromoprop-1-yne (0.043, 0.39 mmol, 80 wt % in toluene) in anhydrous tetrahydrofuran (1 ml) was then added dropwise to the reaction mixture, followed by stirring at −78° C. for 30 minutes then at room temperature for 18 hours. The reaction mixture was quenched with saturated aqueous ammonium chloride solution (10 ml) and diluted with ethyl acetate (10 ml). Distilled water (5 ml) was added and the phases were separated. The aqueous phase was extracted with further ethyl acetate and the combined organic phases were washed with brine, dried over magnesium sulfate, filtered and the filtrate concentrated in vacuo to afford 2-[2-chloro-4-(4-chlorophenyl)-6-methoxyphenyl]-3-methoxy-5-prop-2-ynylcyclopent-2-en-1-one. This material was used directly in the next step.

Step 4: Preparation of 2-[2-chloro-4-(4-chlorophenyl)-6-methoxyphenyl]-4-prop-2-ynylcyclopentane-1,3-dione

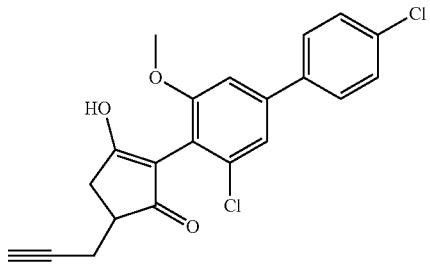 [SMILES: C#CCC1CC(O)=C(c2c(Cl)cc(-c3ccc(Cl)cc3)cc2OC)C1=O]

A solution of 2-[2-chloro-4-(4-chlorophenyl)-6-methoxyphenyl]-3-methoxy-5-prop-2-ynylcyclopent-2-en-1-one (0.115 g, 0.29 mmol) in acetone (2.0 ml) and 2M aqueous hydrochloric acid (1.0 ml) was heated at 100° C. for 30 minutes under microwave irradiation. The reaction mixture was poured into a mixture of dichloromethane and distilled water and the phases were separated. The organic phase was concentrated in vacuo and purified by preparative reverse phase HPLC to afford 2-[2-chloro-4-(4-chlorophenyl)-6-methoxyphenyl]-4-prop-2-ynylcyclopentane-1,3-dione as a white solid.

Example 3: Preparation of 2-[2-fluoro-4-(4-fluorophenyl)-6-methoxyphenyl]-4-prop-2-ynylcyclopentane-1,3-dione

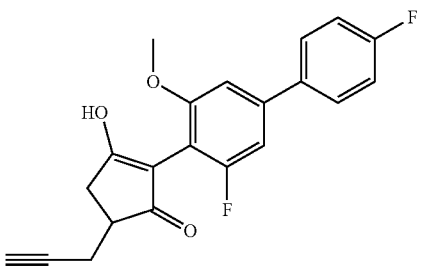 [SMILES: C#CCC1CC(O)=C(c2c(F)cc(-c3ccc(F)cc3)cc2OC)C1=O]

Step 1: Preparation of 2-[4-(4-fluorophenyl)-2-fluoro-6-methoxyphenyl]-3-methoxycyclopent-2-en-1-one

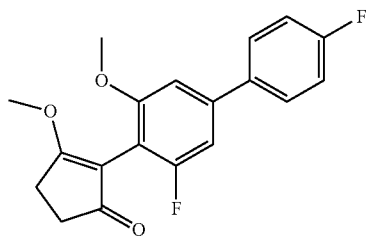 [SMILES: COC1=C(c2c(F)cc(-c3ccc(F)cc3)cc2OC)C(=O)CC1]

To a mixture of 2-(4-bromo-2-fluoro-6-methoxyphenyl)-3-methoxycyclopent-2-en-1-one (0.38 g, 1.22 mmol), 4-fluorophenylboronic acid (0.254 g, 1.82 mmol) and 1,1'-bis(diphenylphosphino)ferrocene palladium(II)dichloride dichloromethane (0.10 g, 0.12 mmol) under nitrogen was added degassed dimethoxyethane (4.2 ml) followed by a solution of tripotassium phosphate (1.03 ml, 4.85 mmol, 40% solution in distilled water). The reaction mixture was heated to 85° C. for 3 hours then left to stand at room temperature overnight. The reaction mixture was diluted with dichloromethane and distilled water and filtered through diatomaceous earth. The phases were separated and the organic phase was concentrated in vacuo and purified by flash column chromatography on silica to afford 2-[4-(4-fluorophenyl)-2-fluoro-6-methoxyphenyl]-3-methoxycyclopent-2-en-1-one.

Step 2: Preparation of 2-[2-fluoro-4-(4-fluorophenyl)-6-methoxyphenyl]-3-methoxy-5-prop-2-ynylcyclopent-2-en-1-one

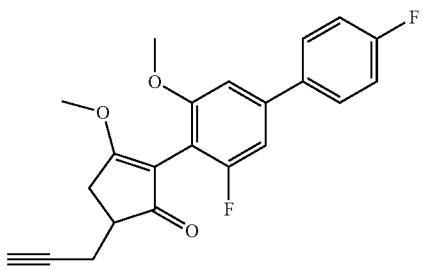 [SMILES: C#CCC1CC(OC)=C(c2c(F)cc(-c3ccc(F)cc3)cc2OC)C1=O]

To a solution of 2-[2-fluoro-4-(4-fluorophenyl)-6-methoxyphenyl]-3-methoxycyclopent-2-en-1-one (0.30 g, 0.91 mmol) in anhydrous tetrahydrofuran (8 ml) under nitrogen at −78° C. was added potassium bis(trimethylsilyl)amide (1.09 mL, 1.09 mmol, 1M solution in tetrahydrofuran) dropwise, and the reaction was stirred at this temperature for 2 hours. A solution of 3-bromoprop-1-yne (0.121 ml, 1.09 mmol, 80 wt % in toluene) in anhydrous tetrahydrofuran (1 ml) was added dropwise to the reaction mixture, followed by stirring at −78° C. for 15 minutes and at room temperature for 18 hours. The reaction mixture was quenched with saturated aqueous ammonium chloride solution (10 ml), diluted with ethyl acetate (10 ml) and the phases were separated. The aqueous phase was extracted with further ethyl acetate (×2), and the combined organic phases were washed with brine, dried over magnesium sulfate, filtered and the filtrate concentrated in vacuo. The crude product was purified by flash column chromatography on silica to afford 2-[2-fluoro-4-(4-fluorophenyl)-6-methoxyphenyl]-3-methoxy-5-prop-2-ynylcyclopent-2-en-1-one.

Step 3: Preparation of 2-[2-fluoro-4-(4-fluorophenyl)-6-methoxyphenyl]-4-prop-2-ynylcyclopentane-1,3-dione

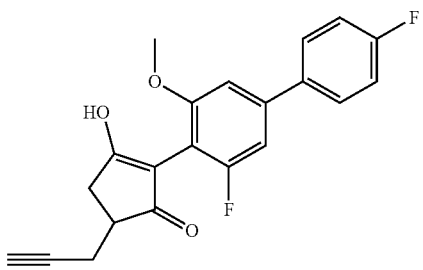 [SMILES: C#CCC1CC(O)=C(c2c(F)cc(-c3ccc(F)cc3)cc2OC)C1=O]

A solution of 2-[2-fluoro-4-(4-fluorophenyl)-6-methoxyphenyl]-3-methoxy-5-prop-2-ynylcyclopent-2-en-1-one (0.230 g, 0.62 mmol) in acetone (2.0 ml) and 2M aqueous hydrochloric acid (1.0 ml) was heated at 100° C. for 30 minutes under microwave irradiation, then left to stand at room temperature overnight. The reaction mixture was poured into a mixture of dichloromethane and distilled water and the phases were separated. The crude product was extracted into 0.5M aqueous potassium carbonate (20 ml) and the aqueous phase was washed with dichloromethane (×3). The aqueous phase was acidified to pH1 with concentrated hydrochloric acid, and the resulting white solid was filtered, washed with additional distilled water and air dried. The product was further dried under vacuum at 55° C. for 18 hours to afford 2-[2-fluoro-4-(4-fluorophenyl)-6-methoxyphenyl]-4-prop-2-ynylcyclopentane-1,3-dione.

Example 4: Preparation of 2-[2-chloro-4-(4-chlorophenyl)-6-fluorophenyl]-4-prop-2-ynylcyclopentane-1,3-dione

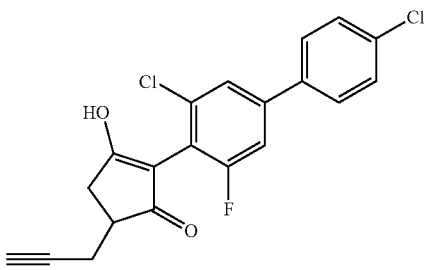 [SMILES: C#CCC1CC(O)=C(c2c(F)cc(-c3ccc(Cl)cc3)cc2Cl)C1=O]

Step 1: Preparation of 2-[2-chloro-6-fluoro-4-(4,4,5,5-tetramethyl-1,3,2-dioxaborolan-2-yl)phenyl]-3-methoxycyclopent-2-en-1-one

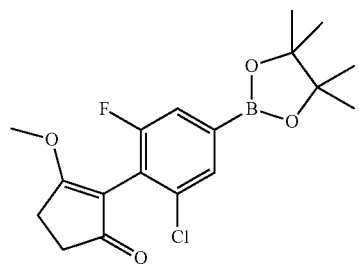

To a mixture of 2-(2-chloro-6-fluorophenyl)-3-methoxycyclopent-2-en-1-one (5.0 g, 20.8 mmol), 4,4,5,5-tetramethyl-2-(4,4,5,5-tetramethyl-1,3,2-dioxaborolan-2-yl)-1,3,2-dioxaborolane (6.33 g, 24.9 mmol), (1,5-cyclooctadiene)(methoxy)iridium(I) dimer (0.62 g, 0.93 mmol) and 4-tert-butyl-2-(4-tert-butyl-2-pyridyl)pyridine (0.50 g, 1.87 mmol) under nitrogen was added tert-butyl methyl ether (21 ml). The resulting solution was heated at 80° C. for 5 hours, cooled to room temperature and concentrated in vacuo. The crude product was purified by flash column chromatography on silica to afford 2-[2-chloro-6-fluoro-4-(4,4,5,5-tetramethyl-1,3,2-dioxaborolan-2-yl)phenyl]-3-methoxycyclopent-2-en-1-one as a yellow solid.

Step 2: Preparation of 2-[2-chloro-4-(4-chlorophenyl)-6-fluorophenyl]-3-methoxycyclopent-2-en-1-one

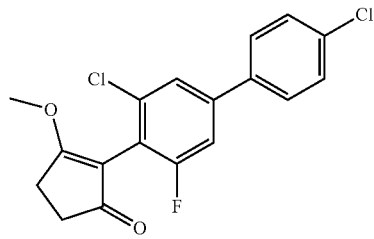 [SMILES: COC1=C(c2c(F)cc(-c3ccc(Cl)cc3)cc2Cl)C(=O)CC1]

To a mixture of 2-[2-chloro-6-fluoro-4-(4,4,5,5-tetramethyl-1,3,2-dioxaborolan-2-yl)phenyl]-3-methoxycyclopent-2-en-1-one (0.50 g, 1.06 mmol), 1,1'-bis(diphenylphosphino)ferrocene palladium(II)dichloride dichloromethane (0.09 g, 0.11 mmol) and 1-bromo-4-chlorobenzene (0.31 g, 1.60 mmol) was added 1,2-dimethoxyethane (8 ml) followed by tripotassium phosphate (0.36 g, 1.70 mmol) in distilled water (0.54 ml). The reaction mixture was heated at 160° C. for 30 minutes under microwave irradiation, followed by cooling to room temperature and subsequent dilution with dichloromethane and distilled water. After filtering through diatomaceous earth the phases were separated and the aqueous phase was further washed with dichloromethane. The organic phases were combined and concentrated in vacuo. The crude product was purified by flash column chromatography on silica to afford 2-[2-chloro-4-(4-chlorophenyl)-6-fluorophenyl]-3-methoxycyclopent-2-en-1-one as a brown gum.

Step 3: Preparation of 2-[2-chloro-4-(4-chlorophenyl)-6-fluorophenyl]-3-methoxy-5-prop-2-ynylcyclopent-2-en-1-one

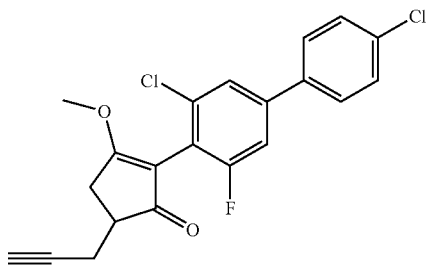 [SMILES: C#CCC1CC(OC)=C(c2c(F)cc(-c3ccc(Cl)cc3)cc2Cl)C1=O]

To a solution of 2-[2-chloro-4-(4-chlorophenyl)-6-fluorophenyl]-3-methoxycyclopent-2-en-1-one (0.28 g, 0.69 mmol) in anhydrous tetrahydrofuran (4 ml) under nitrogen at −78° C. was added potassium bis(trimethylsilyl)amide (0.83 ml, 0.83 mmol, 1M solution in tetrahydrofuran) dropwise, and the reaction mixture was stirred at this temperature for 45 minutes. To this solution was added a second solution of 3-bromoprop-1-yne (0.093 ml, 0.83 mmol, 80 wt % in toluene) in anhydrous tetrahydrofuran (1 ml), followed by stirring at −78° C. for 40 minutes then at room temperature for 18 hours. The reaction mixture was quenched with aqueous ammonium chloride (10 ml) and further diluted with ethyl acetate (10 ml). Distilled water (1 ml) was added, the phases separated, and the aqueous phase extracted again with ethyl acetate (×2). The organic phases were combined, washed with brine, dried over magnesium sulfate, filtered and the filtrate concentrated in vacuo. Purification by flash column chromatography on silica afforded 2-[2-chloro-4-(4-chlorophenyl)-6-fluorophenyl]-3-methoxy-5-prop-2-ynylcyclopent-2-en-1-one.

Step 4: Preparation of 2-[2-chloro-4-(4-chlorophenyl)-6-fluorophenyl]-4-prop-2-ynylcyclopentane-1,3-dione

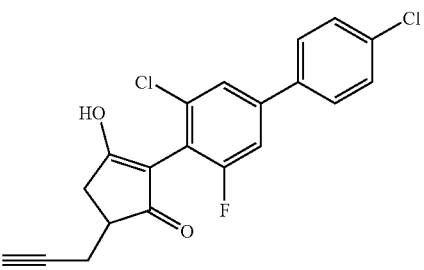 [SMILES: C#CCC1CC(O)=C(c2c(F)cc(-c3ccc(Cl)cc3)cc2Cl)C1=O]

To a solution of 2-[2-chloro-4-(4-chlorophenyl)-6-fluorophenyl]-3-methoxy-5-prop-2-ynylcyclopent-2-en-1-one (0.19 g, 0.48 mmol) in acetone (2.5 ml) was added 2M aqueous hydrochloric acid (0.5 ml) and the resulting solution was heated at 100° C. for 30 minutes under microwave irradiation. The reaction mixture was diluted with dichloromethane and distilled water and the phases were separated. The aqueous phase was washed with further dichloromethane, and the combined organic phases were concentrated in vacuo to afford 2-[2-chloro-4-(4-chlorophenyl)-6-fluorophenyl]-4-prop-2-ynylcyclopentane-1,3-dione as a beige solid.

Example 5: Preparation of 2-[5-(4-chlorophenyl)-2-methylphenyl]-4-prop-2-ynylcyclopentane-1,3-dione

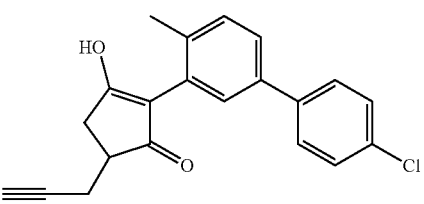 [SMILES: C#CCC1CC(O)=C(c2cc(-c3ccc(Cl)cc3)ccc2C)C1=O]

Step 1: Preparation of (5-bromo-2-methylphenyl)-(2-furyl)methanol

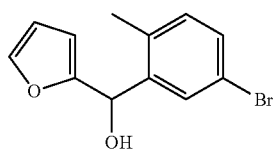

To a solution of 4-bromo-1-iodo-2-methylbenzene (2.0 g, 6.74 mmol) in anhydrous tetrahydrofuran (10 ml) under nitrogen at −30° C. was added isopropylmagnesium chloride lithium chloride complex (5.44 ml, 7.07 mmol, 1.3M solution in tetrahydrofuran) dropwise, maintaining a temperature below −20° C. Once the addition was complete the reaction was allowed to warm to room temperature and stir for 1.5 hours. Additional isopropylmagnesium chloride lithium chloride complex (2.5 ml, 3.25 mmol, 1.3M solution in tetrahydrofuran) was added and the reaction mixture was stirred at −10° C. for 90 mins. A solution of furan-2-carbaldehyde (0.71 g, 7.40 mmol) in tetrahydrofuran (2 ml) was added dropwise, maintaining a reaction temperature below −15° C. The solution was stirred for an additional 60 minutes at −15° C., then at room temperature for 1.5 hours. The reaction mixture was quenched with aqueous ammonium chloride and the crude product extracted with ethyl acetate. The organic phases were combined, dried over magnesium sulfate, filtered and the filtrate concentrated in vacuo. Purification by flash column chromatography on silica afforded (5-bromo-2-methylphenyl)-(2-furyl)methanol as a yellow gum.

Step 2: Preparation of 2-(5-bromo-2-methylphenyl)-3-methoxycyclopent-2-en-1-one

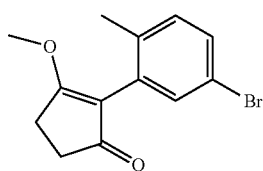 [SMILES: COC1=C(c2cc(Br)ccc2C)C(=O)CC1]

To a solution of (5-bromo-2-methylphenyl)-(2-furyl)methanol (0.97 g, 3.64 mmol) in N,N-dimethylacetamide (9.7 ml) was added 4-methylbenzenesulfonic acid (0.32 g, 1.82 mmol), and the reaction mixture was heated at 170° C. for 2.5 hours. After cooling to room temperature iodomethane (0.77 g, 5.46 mmol) was added followed by potassium carbonate (1.01 g, 7.28 mmol). The reaction mixture was stirred at room temperature for 3 hours then quenched with 2M aqueous hydrochloric acid. The crude product was extracted with ethyl acetate, and the organic phase was further washed with 2M aqueous hydrochloric acid. The organic phases were combined, dried over magnesium sulfate, filtered and the filtrate concentrated in vacuo. The crude product was purified by flash column chromatography on silica to afford 2-(5-bromo-2-methylphenyl)-3-methoxycyclopent-2-en-1-one as a brown oil.

Step 3: Preparation of 2-[5-(4-chlorophenyl)-2-methylphenyl]-3-methoxycyclopent-2-en-1-one

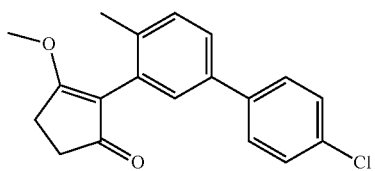 [SMILES: COC1=C(c2cc(-c3ccc(Cl)cc3)ccc2C)C(=O)CC1]

To a solution of 2-(5-bromo-2-methylphenyl)-3-methoxycyclopent-2-en-1-one (0.53 g, 1.88 mmol) in 1,2-dimethoxyethane (10 ml) was added 4-chlorophenylboronic acid (0.35 g, 2.25 mmol) and a solution of tripotassium phosphate (1.59 g, 7.51 mmol) in distilled water (2.90 ml). After degassing with nitrogen for 5 minutes [1,1′-bis(diphenylphosphino)ferrocene]dichloropalladium(II) dichloromethane adduct (0.31 g, 0.37 mmol) was added in one portion and the mixture was heated at 120° C. for 45 minutes under microwave irradiation. The reaction mixture was diluted with distilled water and ethyl acetate. The phases were separated and the aqueous phase was further extracted with ethyl acetate. The combined organic phases were dried over magnesium sulfate, filtered and the filtrate was concentrated in vacuo. The crude product was purified by flash column chromatography on silica to afford 2-[5-(4-chlorophenyl)-2-methylphenyl]-3-methoxycyclopent-2-en-1-one as an orange gum.

Step 4: Preparation of 2-[5-(4-chlorophenyl)-2-methylphenyl]-3-methoxy-5-prop-2-ynylcyclopent-2-en-1-one

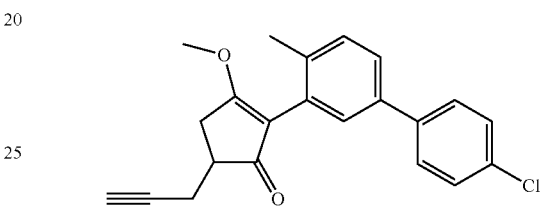

To a solution of 2-[5-(4-chlorophenyl)-2-methylphenyl]-3-methoxycyclopent-2-en-1-one (0.20 g, 0.64 mmol) in anhydrous tetrahydrofuran (4 ml) at −70° C. under nitrogen was added potassium bis(trimethylsilyl)amide (0.88 ml, 0.803 mmol, 0.91M in tetrahydrofuran) dropwise, maintaining a temperature below −60° C. Once addition was complete the reaction mixture was stirred at −70° C. for 60 minutes, followed by addition of propargyl bromide (0.090 ml, 0.803 mmol, 80% solution in toluene). The reaction mixture was stirred at −70° C. for 90 minutes, then additional potassium bis(trimethylsilyl)amide (0.88 ml, 0.803 mmol, 0.91M in tetrahydrofuran) was added dropwise. After stirring at −70° C. for 1 hour the solution was warmed to −40° C. and stirred for an additional 1 hour. The reaction mixture was warmed to −10° C. at which stage it was quenched with 2M aqueous hydrochloric acid. The organic phases were combined, concentrated in vacuo and purified by flash column chromatography on silica to afford 2-[5-(4-chlorophenyl)-2-methylphenyl]-3-methoxy-5-prop-2-ynylcyclopent-2-en-1-one. This material was used directly in the next step.

Step 5: Preparation of 2-[5-(4-chlorophenyl)-2-methylphenyl]-4-prop-2-ynylcyclopentane-1,3-dione

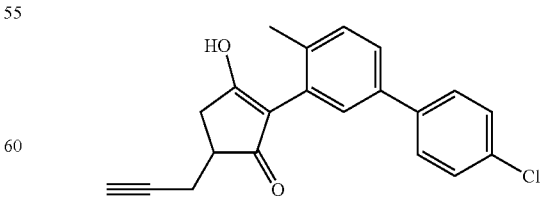

A solution of 2-[5-(4-chlorophenyl)-2-methylphenyl]-3-methoxy-5-prop-2-ynylcyclopent-2-en-1-one (0.06 g, 0.17 mmol) in a mixture of 2M aqueous hydrochloric acid (1 ml) and acetone (1 ml) was heated at 60° C. for 4 hours. After standing at room temperature for 2 days the reaction mixture was diluted with 2M aqueous hydrochloric acid and extracted with ethyl acetate. The combined organic phases were dried over magnesium sulfate, filtered and the filtrate concentrated in vacuo. Purification by flash column chromatography on silica afforded 2-[5-(4-chlorophenyl)-2-methylphenyl]-4-prop-2-ynylcyclopentane-1,3-dione.

Example 6: Synthesis of 2-(2,6-diethyl-4-methyl-phenyl)-4-(prop-2-ynyl)-cyclopentane-1,3-dione (Compound A-25)

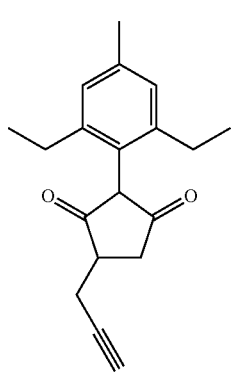 [SMILES: C#CCC1CC(=O)C(c2c(CC)cc(C)cc2CC)C1=O]

Step One: Alkylation of Enol Ether to Prepare 2-(2,6-diethyl-4-methyl-phenyl)-3-methoxy-5-(prop-2-ynyl)-cyclopent-2-en-1-one

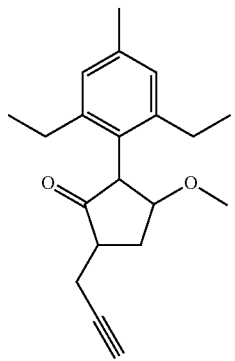 [SMILES: C#CCC1CC(OC)C(c2c(CC)cc(C)cc2CC)C1=O]

To a solution of 2-(2,6-diethyl-4-methyl-phenyl)-3-methoxy-cyclopent-2-en-1-one (499 mg, 1.93 mmol, which can e.g. be prepared as described in Intermediate 3) in anhydrous tetrahydrofuran (10 ml) at −78° C. under a nitrogen atmosphere was added dropwise lithium diisopropylamide (LDA) (1.2 ml of a 1.8M solution in tetrahydrofuran, 2.2 mmol). The reaction was stirred for 30 minutes at −78° C. and then a solution of propargyl bromide (373 mg of an 80% w/w solution in toluene, 2.2 mmol) in 2 ml of tetrahydrofuran was added in a single portion. The reaction was stirred at −78° C. for a further 30 minutes and then allowed to warm to room temperature and stirred for a further hour. The reaction was quenched with saturated aqueous NH$_4$Cl solution (20 ml) and extracted with EtOAc (2×25 ml). The combined organic extracts were evaporated to dryness under reduced pressure and the crude product purified by flash chromatography over SiO$_2$ using an EtOAc/hexane gradient as eluent to give the desired product (500 mg, 87%). $^1$H NMR (400 MHz, CDCl$_3$) 6.90 (2H, s), 3.78 (3H, s), 3.00 (1H, dd), 2.80-2.65 (4H, m), 2.45-2.35 (4H, m), 2.30 (3H, s), 1.95 (1H, s), 1.15-1.00 (6H, m).

Step 2: Enol Ether Cleavage to Prepare 2-(2,6-diethyl-4-methyl-phenyl)-4-(prop-2-ynyl)-cyclopentane-1,3-dione

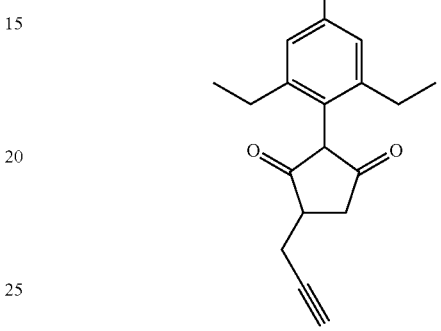

To a solution of 2-(2,6-diethyl-4-methyl-phenyl)-3-methoxy-5-(prop-2-ynyl)-cyclopent-2-en-1-one (250 mg, 0.84 mmol) in acetone (10 ml) was added 2M aqueous hydrochloric acid (10 ml). The reaction was heated at reflux for 3 hours and then allowed to cool to room temperature. The pH of the reaction mixture was adjusted to about 1 by addition of further 2M aqueous hydrochloric acid, and then the reaction mixture was extracted with EtOAc (2×50 ml). The combined organic extracts were evaporated to dryness under reduced pressure and purified by flash chromatography over SiO$_2$ using an EtOAc/hexane gradient as eluent to give the desired product (210 mg, 89%). $^1$H NMR (400 MHz, CDCl$_3$) 6.90 (2H, s), 2.82-2.78 (1H, m), 2.65 (1H, dd), 2.60-2.50 (3H, m), 2.40-2.25 (7H, m), 1.95 (1H, s), 1.10-1.00 (6H, m).

Example 7: Chiral HPLC Separation of Enantiomers of Compound XXX

In one optional embodiment of the invention, any specific compound of the invention (named compound XXX) (racemic) is separated into the two corresponding enantiomerically pure (or substantially enantiomerically pure) compounds using a chiral HPLC column. In one optional example, the chiral HPLC uses the following method and the following conditions.

Chiral HPLC column: a (s,S) WhelkO1-5 micron-21 mm×250 mm HPLC column, manufactured by Regis Technologies, Inc. In this column, the chiral stationary phase is (S,S) 1-(3-5-dinitrobenzamido)-1,2,3,4-tetrahydrophenanthrene.

The solvent system to be used as an eluent for the column varies depending on the racemic compound to be separated into enantiomers, but one example of a solvent system is: a 30:70 (by volume) mixture of Solvent A and Solvent B, in which: Solvent A is isohexane containing 0.1% v/v of trifluoroacetic acid (TFA), and Solvent B is ethanol.

Other conditions (these are sample conditions only and may vary widely):

Flow rate through column: about 21 ml/minute. Run time: about 20 minutes.

Loading (compound loaded onto column): about 50 mg/ml of compound in ethanol.

Volume of sample (compound) injected per run=about 1800 microliters.

Number of injections of compound=about 5.

Amount of racemic compound XXX used: (for example) about 300-400 mg

Abbreviation: HPLC=high performance (or high pressure) liquid chromatography.

General Note on Chiral HPLC Separation of Enantiomers:

In one optional embodiment, the above procedure using chiral HPLC is used to separate the enantiomers of other compounds of formula (I) of the present the invention. Chiral columns which might be useful to achieve this are as follows:

(s,$) WhelkO1-5 micron-21 mm×250 mm HPLC column, manufactured by Regis Technologies, Inc [in this column, the chiral stationary phase is (S,S) 1-(3-5-dinitrobenzamido)-1,2,3,4-tetrahydrophenanthrene];

Kromasil® AmyCoat™ [whose chiral stationary phase is tris-(3,5-dimethylphenyl)carbamoyl amylose];

Kromasil® CelluCoat™ [whose chiral stationary phase is tris-(3,5-dimethylphenyl)carbamoyl cellulose];

Chiralpak® IA [whose chiral stationary phase is a (3,5-dimethylphenyl)carbamate derivative of amylose];

Chiralpak® IB [whose chiral stationary phase is tris-(3, 5-dimethylphenyl)carbamate derivative of cellulose];

Chiralpak® IC [whose chiral stationary phase is cellulose tris(3,5-dichlorophenyl)carbamate];

Lux® Amylose-2 [whose chiral stationary phase is amylose tris(5-chloro-2-methylphenylcarbamate)]; or Lux® Cellulose-2 [whose chiral stationary phase is Cellulose tris(3-chloro-4-methylphenylcarbamate)].

Example 8 Preparation of [2-[4-(4-fluorophenyl)-2, 6-dimethyl-phenyl]-3-oxo-4-prop-2-ynyl-cyclopentyl]acetate

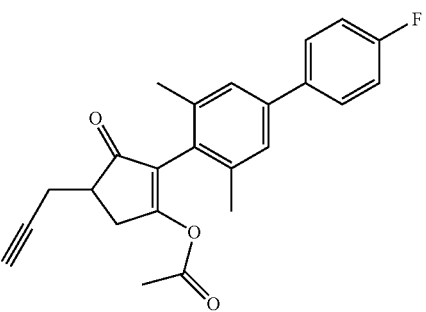 [SMILES: C#CCC1CC(OC(C)=O)=C(c2c(C)cc(-c3ccc(F)cc3)cc2C)C1=O]

To a cooled (0° C.) suspension of 2-[4-(4-fluorophenyl)-2,6-dimethyl-phenyl]-4-prop-2-ynylcyclopentane-1,3-dione (0.203 g) in dichloromethane (15 mL) was added triethylamine (0.127 mL) followed by acetyl chloride (0.06475 mL). The solution was stirred cold for 15 minutes then allowed to warm to room temperature and the reaction mixture was stirred at room temperature for 75 min.

The reaction was partitioned between water and dichloromethane and the organic layer was concentrated and purified by chromatography on silica eluting with ethyl acetate in isohexane to give [2-[4-(4-fluorophenyl)-2,6-dimethyl-phenyl]-3-oxo-4-prop-2-ynyl-cyclopentyl]acetate (105 mg) as a yellow gum.

$^1$H NMR (500 MHz, CDCl$_3$) δ=7.56-7.52 (m, 2H), 7.24 (s, 2H), 7.13-7.09 (m, 2H), 3.36-3.29 (m, 1H), 3.10 (dd, 1H), 2.94-2.92 (m, 1H), 2.73-2.71 (m, 2H), 2.18-2.17 (m, 9H), 2.00 (t, 1H)

(Note: The other isomer, in which the acetyloxy group is attached to the ring carbon adjacent to the prop-2-ynyl group, might be formed, as well or instead.)

Additional compounds in Table T1 below illustrate the present invention, and are particular embodiments of the compounds of formula (I) according to the present invention. For the most part, these compounds can generally be prepared by methods similar to those shown in the Examples and/or in the process section hereinabove using appropriate starting materials.

TABLE T1

It should be noted that certain compounds of the invention may exist as a mixture of isomers, including sometimes atropisomers, e.g. as noted above, under the conditions used to obtain the $^1$H NMR data. Where this has occurred, the characterising data are reported for all isomers present at ambient temperature in the specified solvent. Unless otherwise stated, proton ($^1$H) NMR spectra disclosed herein were recorded at ambient temperature.

| Compound Number | Structure | $^1$H NMR (CDCl$_3$ unless stated, usually 400 MHz) data |
|---|---|---|
| A1 | 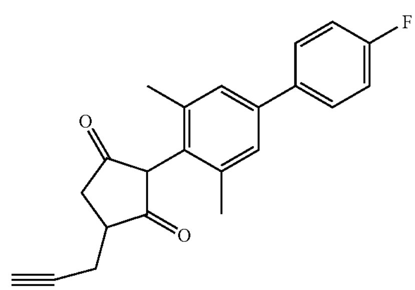 [SMILES: C#CCC1CC(=O)C(c2c(C)cc(-c3ccc(F)cc3)cc2C)C1=O] | δ 7.54-7.50 (m, 2H), 7.26 (s, 2H), 7.13-7.09 (2H, m), 3.03-2.95 (br. m, 1H), 2.90-2.84 (m, 1H), 2.71-2.67 (m, 3H), 2.20 (s, 3H), 2.19 (s, 3H), 1.99 (t, 1H). 1H missing. |

TABLE T1-continued
| | | |
|---|---|---|
| A2 | 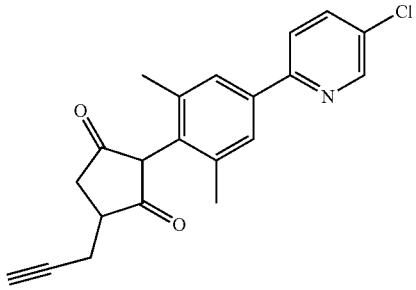 [SMILES: C#CCC1CC(=O)C(c2c(C)cc(-c3ccc(Cl)cn3)cc2C)C1=O] | δ 8.45 (d, 1H), 7.68 (dd, 1H), 7.47 (d, 1H), 7.27 (s, 2H), 6.32 (br.s, 1H), 2.90-2.85 (m, 1H), 2.79-2.73 (m, 1H), 2.63-2.55 (m, 3H), 2.03 (s, 3H), 2.00 (s, 3H), 1.97 (t, 1H). |
| A3 | 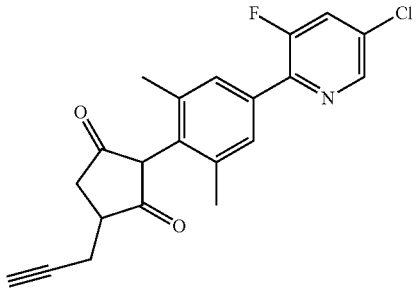 [SMILES: C#CCC1CC(=O)C(c2c(C)cc(-c3ncc(Cl)cc3F)cc2C)C1=O] | δ 8.47 (s, 1H), 7.64 (s, 2H), 7.54 (dd, 1H), 2.93-2.87 (m, 1H), 2.73-2.70 (br.m, 3H), 2.63 (s, 1H), 2.24 (s, 3H), 2.21 (s, 3H), 2.01 (t, 1H). 1H missing. |
| A4 | 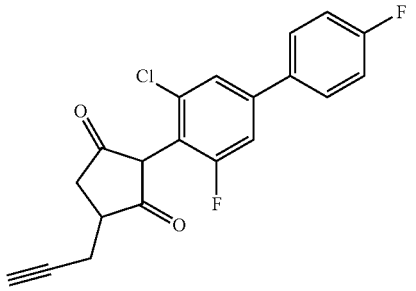 [SMILES: C#CCC1CC(=O)C(c2c(F)cc(-c3ccc(F)cc3)cc2Cl)C1=O] | d-chloroform + 1 drop d4-methanol δ 7.53-7.46 (m, 2H), 7.43-7.37 (m, 1H), 7.23-7.08 (m, 3H), 2.97-2.85 (m, 2H), 2.75-2.64 (m, 2H), 2.62-2.51 (m, 1H), 2.70 (app.q, 1H). 1H missing. |
| A5 | 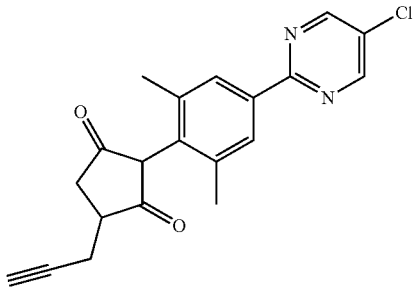 [SMILES: C#CCC1CC(=O)C(c2c(C)cc(-c3ncc(Cl)cn3)cc2C)C1=O] | d4-methanol δ 8.81 (s, 2H), 8.10 (s, 2H), 2.99-2.88 (m, 2H), 2.74-2.62 (m, 3H), 2.33 (t, 3H), 2.24 (s, 3H), 2.20 (s, 3H). 1H missing. |
| A6 | 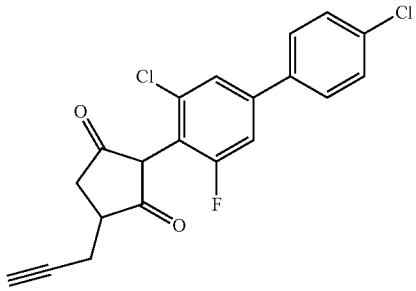 [SMILES: C#CCC1CC(=O)C(c2c(F)cc(-c3ccc(Cl)cc3)cc2Cl)C1=O] | d-chloroform + 1 drop d4-methanol δ 7.46-7.39 (m, 5H), 7.18 (dd, 1H), 2.94-2.86 (m, 2H), 2.75-2.61 (m, 2H), 2.58-2.49 (m, 1H), 2.00-1.98 (m, 1H). 1H missing. |

TABLE T1-continued
| A7 | 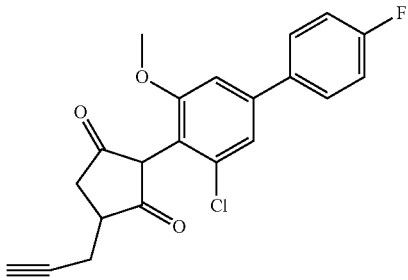 [SMILES: C#CCC1CC(=O)C(c2c(Cl)cc(-c3ccc(F)cc3)cc2OC)C1=O] | δ 7.68-7.65 (m, 2H), 7.27 (d, 1H), 7.21-7.17 (m, 2H), 7.11-7.10 (m, 1H), 3.83 and 3.82 (2 × s, 3H), 2.93-2.84 (m, 2H), 2.72-2.48 (m, 3H), 2.32 and 2.29 (2 × t, 1H). 1H missing. |
|---|---|---|
| A8 | 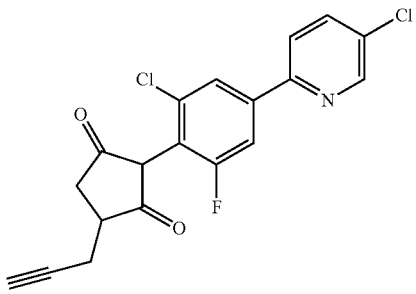 [SMILES: C#CCC1CC(=O)C(c2c(F)cc(-c3ccc(Cl)cn3)cc2Cl)C1=O] | d4-methanol δ 8.65 (dd, 1H), 8.00 (app.s, 1H), 7.96-7.91 (m, 2H), 7.78 (dd, 1H), 2.99-2.91 (m, 2H), 2.75-2.56 (m, 3H), 2.31 (app.q, 1H). 1H missing. |
| A9 | 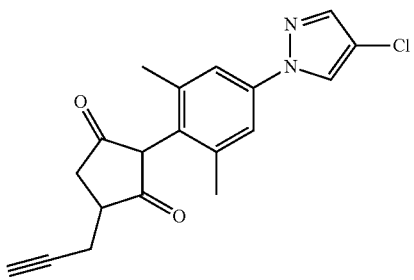 [SMILES: C#CCC1CC(=O)C(c2c(C)cc(-n3cc(Cl)cn3)cc2C)C1=O] | d-chloroform + 1 drop d4-methanol δ 7.87 (s, 1H), 7.62 (s, 1H), 7.30 (s, 2H), 2.96 (br.s, 1H), 2.89-2.83 (m, 1H), 2.70-2.65 (m, 3H), 2.21 (s, 3H), 2.18 (s, 3H), 1.99 (t, 1H). 1H missing. |
| A10 | 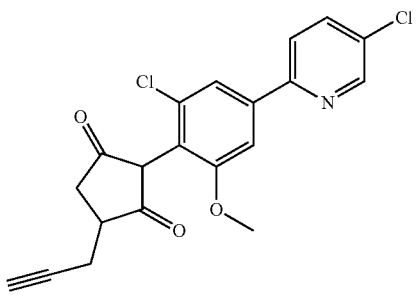 [SMILES: C#CCC1CC(=O)C(c2c(Cl)cc(-c3ccc(Cl)cn3)cc2OC)C1=O] | δ 8.57-8.56 (m, 1H), 7.71 (dd, 1H), 7.52 (d, 1H), 7.24-7.23 (m, 1H), 7.17-7.18 (m, 1H), 3.72 (app. d, 3H), 3.04-2.96 (br.m, 1H), 2.92-2.84 (m, 1H), 2.74-2.52 (m, 3H), 2.02-1.99 (m, 1H). 1H missing. |
| A11 | 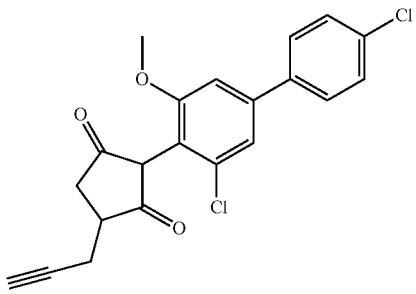 [SMILES: C#CCC1CC(=O)C(c2c(Cl)cc(-c3ccc(Cl)cc3)cc2OC)C1=O] | d4-methanol δ 7.67-7.63 (m, 2H), 7.47-7.45 (m, 2H), 7.29 (d, 1H), 7.13 (s, 1H), 3.84-3.82 (m, 3H), 2.94-2.84 (m, 2H), 2.71-2.50 (m, 3H), 2.33-2.28 (m, 1H). 1H missing. |

TABLE T1-continued
| | | |
|---|---|---|
| A12 | 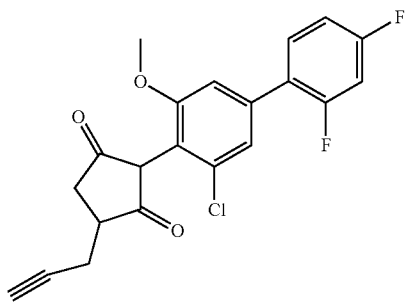 [SMILES: C#CCC1CC(=O)C(c2c(Cl)cc(-c3ccc(F)cc3F)cc2OC)C1=O] | d4-methanol δ 7.59-7.53 (m, 1H), 7.19 (t, 1H), 7.10-7.04 (m, 3H), 3.80-3.79 (m, 3H), 2.95-2.84 (m, 2H), 2.72-2.48 (m, 3H), 2.32 and 2.29 (2 × t, 1H). 1H missing. |
| A13 | 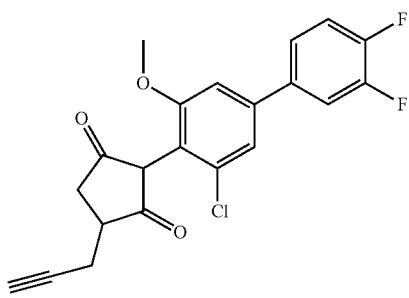 [SMILES: C#CCC1CC(=O)C(c2c(Cl)cc(-c3ccc(F)c(F)c3)cc2OC)C1=O] | d4-methanol δ 7.59 (ddd, 1H), 7.49-7.44 (m, 1H), 7.38-7.31 (m, 1H), 7.28 (d, 1H), 7.11 (s, 1H), 3.84-3.83 (m, 3H), 2.95-2.84 (m, 2H), 2.72-2.48 (m, 3H), 2.32 and 2.28 (2 × t, 1H). 1H missing. |
| A14 | 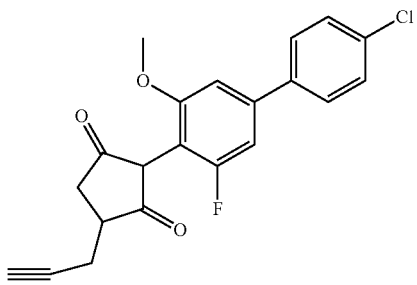 [SMILES: C#CCC1CC(=O)C(c2c(F)cc(-c3ccc(Cl)cc3)cc2OC)C1=O] | d4-methanol δ 7.66-7.64 (m, 2H), 7.46-7.44 (m, 2H), 7.02 (br.s, 1H), 6.99 (dd, 1H), 3.85-3.84 (m, 3H), 2.94-2.84 (m, 2H), 2.72-2.47 (m, 3H), 2.29 (dt, 1H). 1H missing. |
| A15 | 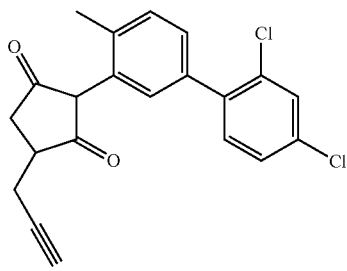 [SMILES: C#CCC1CC(=O)C(c2cc(-c3ccc(Cl)cc3Cl)ccc2C)C1=O] | δ 7.48 (d, 1 H), 7.30-7.39 (m, 4 H), 7.15 (d, 1 H), 2.51-3.03 (m, 5 H), 2.26 (d, 3 H), 1.97 (br.s., 1 H). 1H missing. |
| A16 | 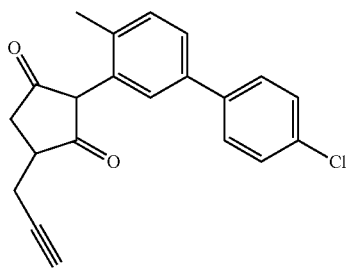 [SMILES: C#CCC1CC(=O)C(c2cc(-c3ccc(Cl)cc3)ccc2C)C1=O] | δ 7.48 (d, 2 H), 7.30-7.39 (m, 3 H), 7.15 (d, 2 H), 2.51-3.03 (m, 5 H), 2.26 (d, 3 H), 1.97 (br.s., 1 H). 1H missing. |

TABLE T1-continued
A17 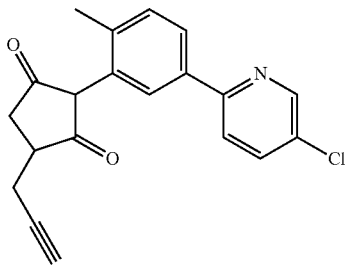 [SMILES: C#CCC1CC(=O)C(c2cc(-c3ccc(Cl)cn3)ccc2C)C1=O] d4-methanol δ 8.62 (d, 1 H), 7.94-(m, 1 H), 7.82-7.92 (m, 2 H), 7.70 (d, 1 H), 7.40 (d, 1 H), 2.63-2.71 (m, 3 H), 2.88-2.99 (m, 2 H), 2.36 (t, 1 H), 2.25-2.29 (m, 3 H). 1H missing.
A18 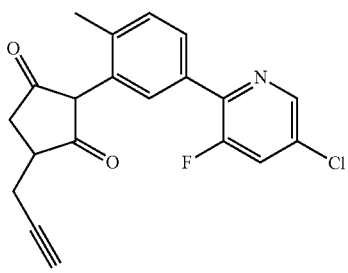 [SMILES: C#CCC1CC(=O)C(c2cc(-c3ncc(Cl)cc3F)ccc2C)C1=O] d4-methanol δ 8.39 (dd, 1 H), 7.75 (d, 1 H), 7.68-7.74 (m, 1 H), 7.57 (s, 1 H), 7.28 (d, 1 H), 2.76-2.88 (m, 2 H) 2.51-2.61 (m, 3 H), 2.17 (s, 3 H) 2.24 (t, 1 H). 1H missing.
A19 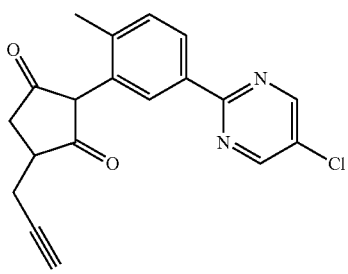 [SMILES: C#CCC1CC(=O)C(c2cc(-c3ncc(Cl)cn3)ccc2C)C1=O] d4-methanol δ 8.82 (s, 2 H), 8.26 (dd, 1 H), 8.16 (d, 1 H), 7.38 (d, 1 H), 2.92 (d, 2 H), 2.35 (t, 1 H), 2.60-2.72 (m, 3 H), 2.27 (s, 3 H). 1H missing.
A20 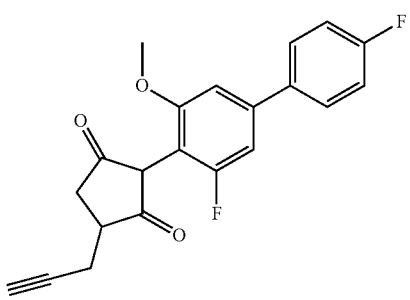 [SMILES: C#CCC1CC(=O)C(c2c(F)cc(-c3ccc(F)cc3)cc2OC)C1=O] d-chloroform. δ 7.69-7.66 (m, 2H), 7.21-7.16 (m, 2H), 7.01 (br.s, 1H), 6.97 (dd, 1H), 3.85-3.84 (m, 3H), 2.95-2.84 (m, 2H), 2.71-2.65 (m, 1H), 2.61 (d, 1H), 2.57-2.48 (m, 1H), 2.30 (dt, 1H). 1H missing.
A21 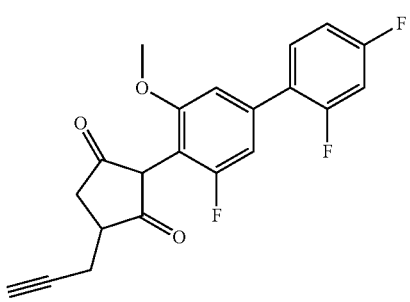 [SMILES: C#CCC1CC(=O)C(c2c(F)cc(-c3ccc(F)cc3F)cc2OC)C1=O] d4-methanol δ 7.60-7.54 (m, 1H), 7.10-7.05 (m, 2H), 6.94 (s, 1H), 6.90 (d, 1H), 3.82-3.81 (m, 3H), 2.95-2.84 (m, 2H), 2.72-2.47 (m, 3H), 2.30 (dt, 1H). 1H missing TABLE T1-continued
| | | |
|---|---|---|
| A22 | 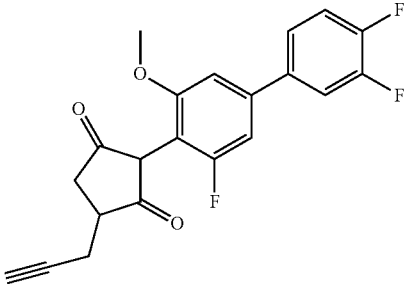 [SMILES: C#CCC1CC(=O)C(c2c(F)cc(-c3ccc(F)c(F)c3)cc2OC)C1=O] | d4-methanol δ 7.60 (ddd, 1H), 7.50-7.46 (m, 1H), 7.35 (dt, 1H), 7.02-6.98 (m, 2H), 3.86-3.85 (m, 3H), 2.95-2.85 (m, 2H), 2.71-2.48 (m, 3H), 2.30 (dt, 1H). 1H missing |
| A23 | 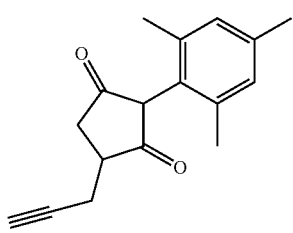 [SMILES: C#CCC1CC(=O)C(c2c(C)cc(C)cc2C)C1=O] | $^1$H NMR (400 MHz, CDCl$_3$) δ (delta) 6.91 (2H, s), 2.89-2.81 (2H, m), 2.69-2.62 (3H, m), 2.28 (3H, s), 2.12 (3H, s), 2.09 (3H, s), 1.98 (1H, s) |
| A24 | 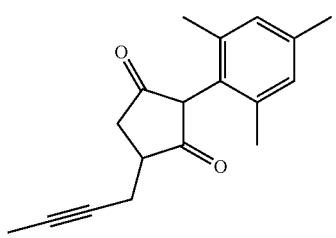 [SMILES: CC#CCC1CC(=O)C(c2c(C)cc(C)cc2C)C1=O] | $^1$H NMR (400 MHz, CDCl$_3$) δ (delta) 6.91 (2H, s), 2.89-2.52 (5H, m), 2.28 (3H, s), 2.19-2.11 (3H, s, br), 2.10 (3H, s), 1.73 (3H, s) |
| A25 | 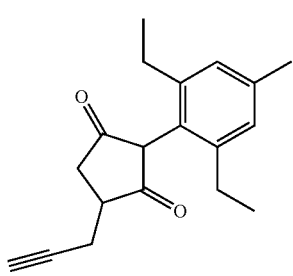 [SMILES: C#CCC1CC(=O)C(c2c(CC)cc(C)cc2CC)C1=O] | $^1$H NMR (400 MHz, CDCl$_3$) δ (delta) 6.90 (2H, s), 2.82-2.78 (1H, m), 2.65 (1H, dd), 2.60-2.50 (3H, m), 2.40-2.25 (7H, m), 1.95 (1H, s), 1.10-1.00 (6H, m) |
| A26 | 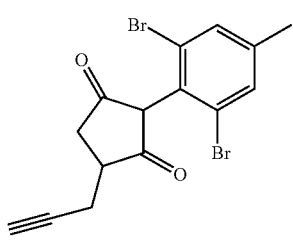 [SMILES: C#CCC1CC(=O)C(c2c(Br)cc(C)cc2Br)C1=O] | $_1$H NMR (400 MHz, CDCl$_3$) δ (delta) 7.40 (2H, s), 2.85-3.00 (2H, m), 2.62-2.72 (2H, m), 2.53 (1H, dd), 2.28 (3H, s), 2.01 (1H, t) |
| A27 | 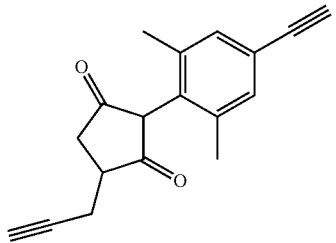 [SMILES: C#CCC1CC(=O)C(c2c(C)cc(C#C)cc2C)C1=O] | $^1$H NMR (400 MHz, d4-MeOH) δ (delta) 7.15 (2H, s), 3.29 (1H, s), 2.98-2.82 (2H, m), 2.72-2.57 (3H, m), 2.31 (1H, s), 2.11 (3H, s), 2.02 (3H, s) |

TABLE T1-continued
A28 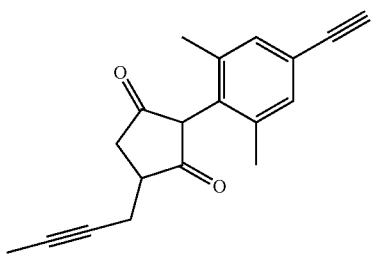 [SMILES: C#Cc1cc(C)c(C2C(=O)CC(CC#CC)C2=O)c(C)c1]
¹H NMR (400 MHz, d4-MeOH) δ (delta) 7.16 (2H, s), 3.29 (1H, s), 2.91-2.78 (2H, m), 2.70-2.49 (3H, m), 2.13 (3H, s), 2.08 (3H, s), 1.71 (3H, s)
A29 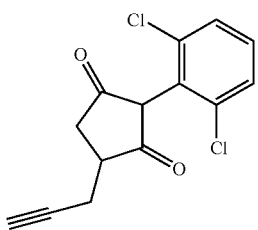 [SMILES: C#CCC1CC(=O)C(c2c(Cl)cccc2Cl)C1=O]
¹H NMR (400 MHz, CDCl₃) δ (delta) 7.25 (2H, d), 7.06 (1H, dd), 2.88-2.78 (2H, m), 2.65-2.44 (3H, m), 1.96 (1H, s)
A30 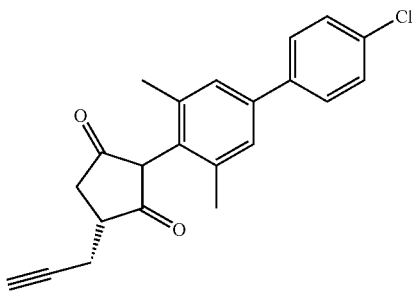
A31 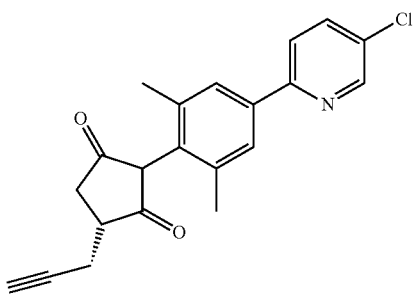
A32 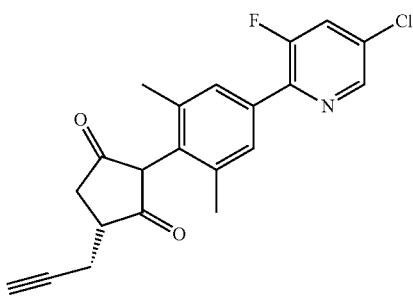

TABLE T1-continued
A33 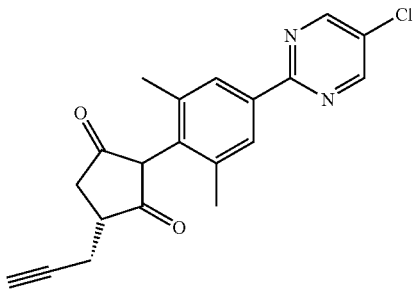
A34 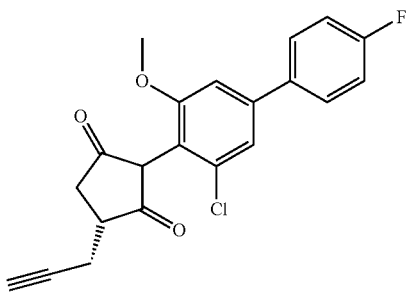
A35 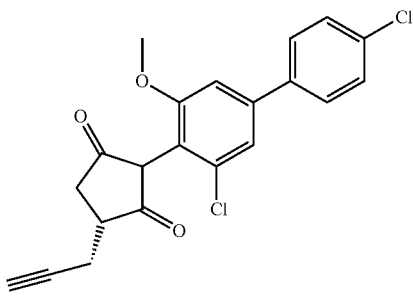
A36 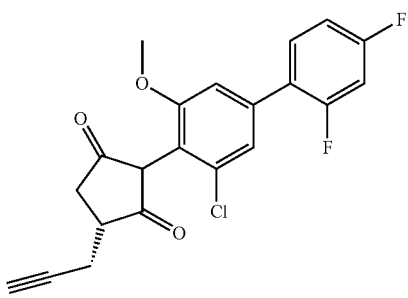
A37 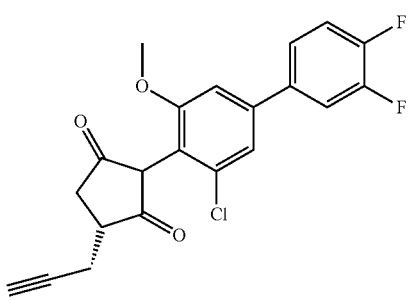

TABLE T1-continued
A38 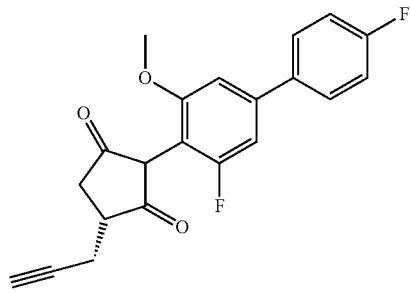
A39 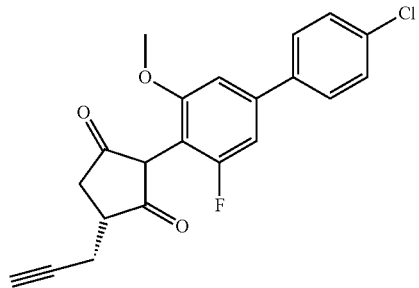
A40 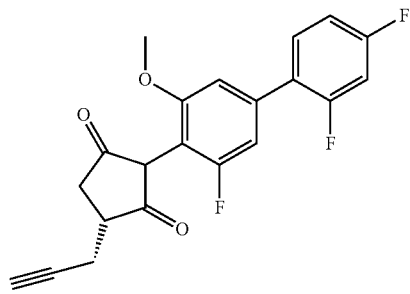
A41 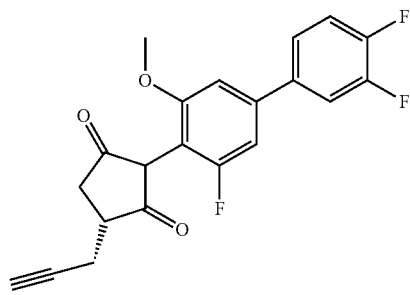
| Compound Number | Structure | $^1$H NMR 400 MHz δ (delta) data (CDCl$_3$, unless stated) |
|---|---|---|
| A42 | 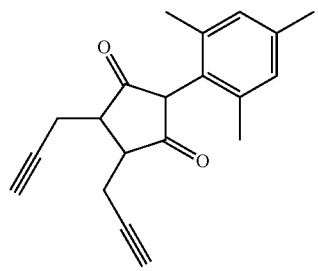 [SMILES: C#CCC1C(=O)C(c2c(C)cc(C)cc2C)C(=O)C1CC#C] | 6.92 (s, 2H), 3.01 (br.s., 2H) 2.73 (br.s., 4H), 2.28 (s, 3H), 2.11 (s, 6H), 1.99 (br.s., 2H). 1H is missing, because of cyclic dione proton exchange. |

TABLE T1-continued

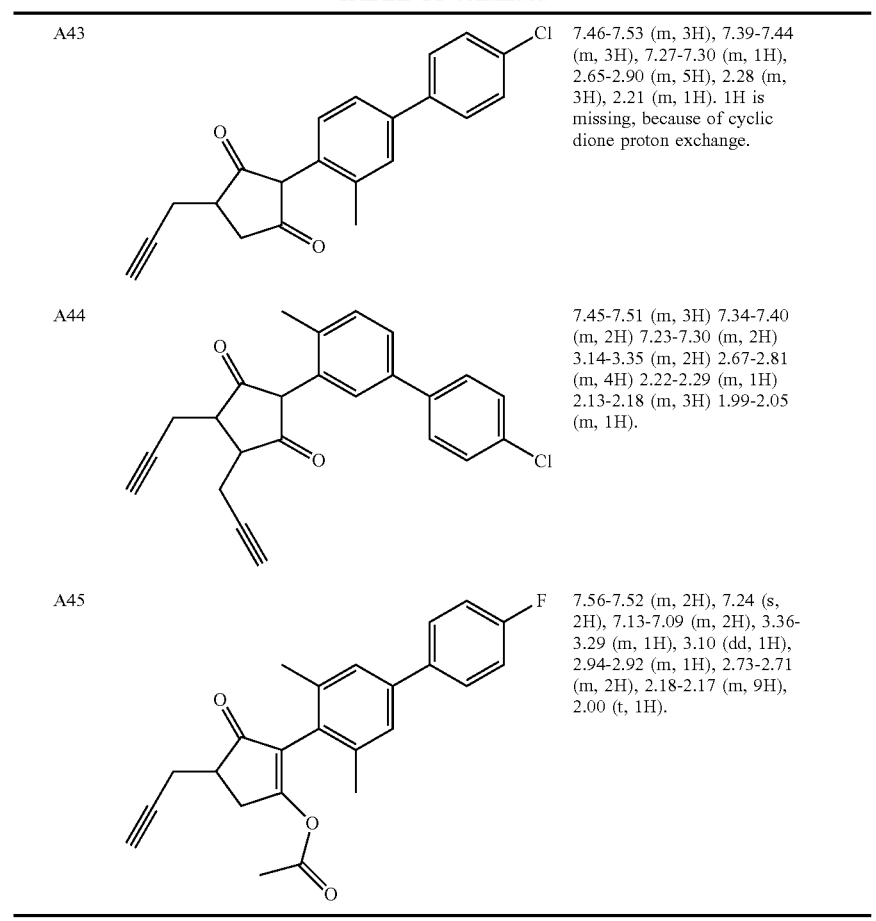

| | | |
|---|---|---|
| A43 | | 7.46-7.53 (m, 3H), 7.39-7.44 (m, 3H), 7.27-7.30 (m, 1H), 2.65-2.90 (m, 5H), 2.28 (m, 3H), 2.21 (m, 1H). 1H is missing, because of cyclic dione proton exchange. |
| A44 | | 7.45-7.51 (m, 3H) 7.34-7.40 (m, 2H) 7.23-7.30 (m, 2H) 3.14-3.35 (m, 2H) 2.67-2.81 (m, 4H) 2.22-2.29 (m, 1H) 2.13-2.18 (m, 3H) 1.99-2.05 (m, 1H). |
| A45 | | 7.56-7.52 (m, 2H), 7.24 (s, 2H), 7.13-7.09 (m, 2H), 3.36-3.29 (m, 1H), 3.10 (dd, 1H), 2.94-2.92 (m, 1H), 2.73-2.71 (m, 2H), 2.18-2.17 (m, 9H), 2.00 (t, 1H). |

The compounds of the following Tables 1 to 60 can be obtained in an analogous manner.

Table 1 covers compounds of the following type

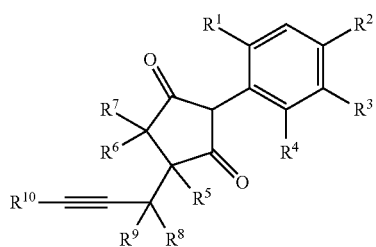

wherein $R^1$ is methyl, $R^4$ is methyl, $R^{10}$ is hydrogen and all of $R^3$, $R^5$, $R^6$, $R^7$, $R^8$, and $R^9$ are hydrogen. $R^2$ is as defined in Table 1.

TABLE 1

| Compound Number | $R^2$ |
|---|---|
| 1.001 | phenyl |
| 1.002 | 3-fluorophenyl |
| 1.003 | 4-fluorophenyl |
| 1.004 | 3-chlorophenyl |
| 1.005 | 4-chlorophenyl |
| 1.006 | 3-bromophenyl |
| 1.007 | 4-bromophenyl |

TABLE 1-continued

| Compound Number | $R^2$ |
|---|---|
| 1.008 | 4-iodophenyl |
| 1.009 | 4-methylphenyl |
| 1.010 | 4-cyanophenyl |
| 1.011 | 4-methoxyphenyl |
| 1.012 | 3-difluoromethoxyphenyl |
| 1.013 | 4-difluoromethoxyphenyl |
| 1.014 | 3-difluoromethylphenyl |
| 1.015 | 4-difluoromethylphenyl |
| 1.016 | 3-trifluoromethylphenyl |
| 1.017 | 4-trifluoromethylphenyl |
| 1.018 | 3-trifluoromethoxyphenyl |
| 1.019 | 4-trifluoromethoxyphenyl |
| 1.020 | 4-methylthiophenyl |
| 1.021 | 4-methylsulfinylphenyl |
| 1.022 | 4-methylsulfonylphenyl |
| 1.023 | 2,4-difluorophenyl |
| 1.024 | 3,4-difluorophenyl |
| 1.025 | 3,5-difluorophenyl |
| 1.026 | 2,4-dichlorophenyl |
| 1.027 | 3,4-dichlorophenyl |
| 1.028 | 4-chloro-2-fluorophenyl |
| 1.029 | 4-chloro-3-fluorophenyl |
| 1.030 | 4-chloro-2-methoxyphenyl |
| 1.031 | 4-chloro-3-methoxyphenyl |
| 1.032 | 4-chloro-2-methylphenyl |
| 1.033 | 4-chloro-3-methylphenyl |
| 1.034 | 2-fluoro-4-cyanophenyl |
| 1.035 | 2-chloropyridin-5-yl |
| 1.036 | 5-chloropyridin-2-yl |
| 1.037 | 3-fluoro-5-chloropyridin-2-yl |
| 1.038 | 5-trifluoromethylpyridin-2-yl |

TABLE 1-continued

| Compound Number | $R^2$ |
| --- | --- |
| 1.039 | 3-chloro-5-trifluoromethylpyridin-2-yl |
| 1.040 | 5-fluoropyridin-2-yl |
| 1.041 | 5-bromopyridin-2-yl |
| 1.042 | 6-chloropyridazin-3-yl |
| 1.043 | 5-bromopyrimidin-2-yl |
| 1.044 | 5-chloropyrimidin-2-yl |
| 1.045 | 5-fluoropyrimidin-2-yl |
| 1.046 | 4-chlorothien-2-yl |
| 1.047 | 5-chlorothien-2-yl |
| 1.048 | 3-chloropyrazol-1-yl |
| 1.049 | 4-chloropyrazol-1-yl |

Table 2 covers compounds of the following type

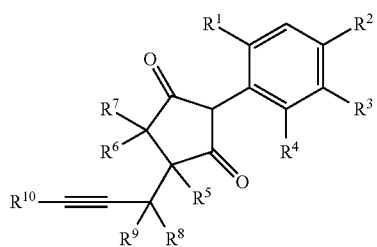

wherein $R^1$ is methyl, $R^4$ is hydrogen, $R^{10}$ is hydrogen and all of $R^3$, $R^5$, $R^6$, $R^7$, $R^8$, and $R^9$ are hydrogen. $R^2$ is as defined in Table 1.

Table 3 covers compounds of the following type

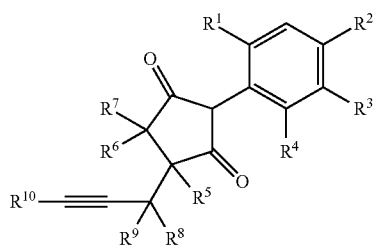

wherein $R^1$ is methyl, $R^4$ is ethyl, $R^{10}$ is hydrogen and all of $R^3$, $R^5$, $R^6$, $R^7$, $R^8$, and $R^9$ are hydrogen. $R^2$ is as defined in Table 1.

Table 4 covers compounds of the following type

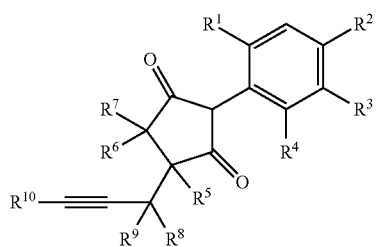

wherein $R^1$ is ethyl, $R^4$ is hydrogen, $R^{10}$ is hydrogen and all of $R^3$, $R^5$, $R^6$, $R^7$, $R^8$, and $R^9$ are hydrogen. $R^2$ is as defined in Table 1.

Table 5 covers compounds of the following type

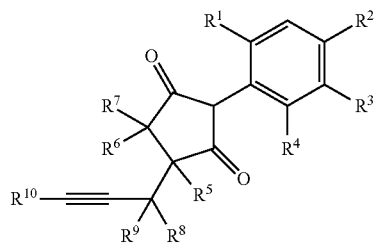

wherein $R^1$ is methyl, $R^4$ is methoxy, $R^{10}$ is hydrogen and all of $R^3$, $R^5$, $R^6$, $R^7$, $R^8$, and $R^9$ are hydrogen. $R^2$ is as defined in Table 1.

Table 6 covers compounds of the following type

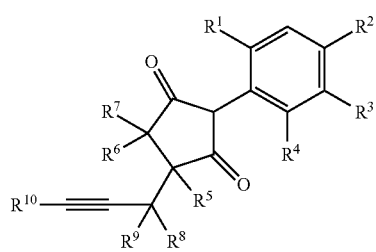

wherein $R^1$ is methyl, $R^4$ is ethoxy, $R^{10}$ is hydrogen and all of $R^3$, $R^5$, $R^6$, $R^7$, $R^8$, and $R^9$ are hydrogen. $R^2$ is as defined in Table 1.

Table 7 covers compounds of the following type

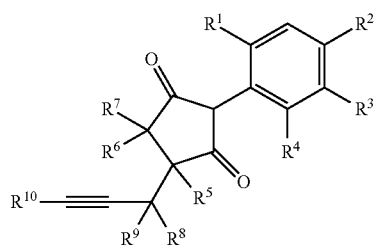

wherein $R^1$ is methyl, $R^4$ is 2-methoxyethoxy, $R^{10}$ is hydrogen and all of $R^3$, $R^5$, $R^6$, $R^7$, $R^8$, and $R^9$ are hydrogen. $R^2$ is as defined in Table 1.

Table 8 covers compounds of the following type

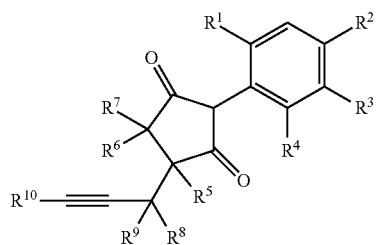

wherein $R^1$ is methyl, $R^4$ is 2,2,2-trifluoroethoxy, $R^{10}$ is hydrogen and all of $R^3$, $R^5$, $R^6$, $R^7$, $R^8$, and $R^9$ are hydrogen. $R^2$ is as defined in Table 1.

Table 9 covers compounds of the following type

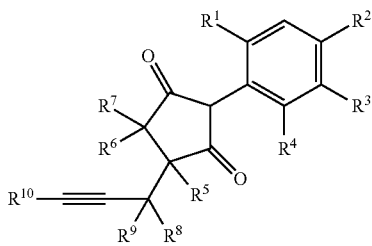

wherein $R^1$ is chloro, $R^4$ is methoxy, $R^{10}$ is hydrogen and all of $R^3$, $R^5$, $R^6$, $R^7$, $R^8$, and $R^9$ are hydrogen. $R^2$ is as defined in Table 1.

Table 10 covers compounds of the following type

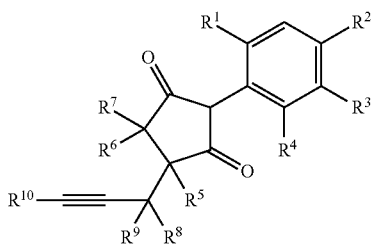

wherein $R^1$ is chloro, $R^4$ is ethoxy, $R^{10}$ is hydrogen and all of $R^3$, $R^5$, $R^6$, $R^7$, $R^8$, and $R^9$ are hydrogen. $R^2$ is as defined in Table 1.

Table 11 covers compounds of the following type

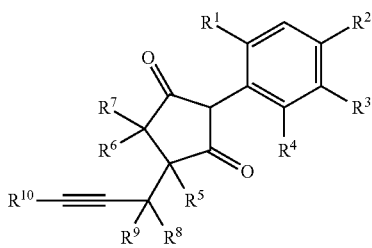

wherein $R^1$ is chloro, $R^4$ is 2-methoxyethoxy, $R^{10}$ is hydrogen and all of $R^3$, $R^5$, $R^6$, $R^7$, $R^8$, and $R^9$ are hydrogen. $R^2$ is as defined in Table 1.

Table 12 covers compounds of the following type

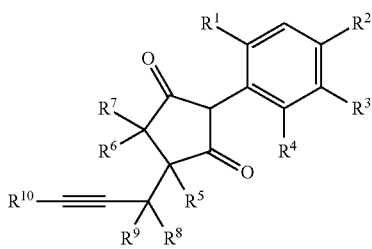

wherein $R^1$ is chloro, $R^4$ is 2,2,2-trifluoroethoxy, $R^{10}$ is hydrogen and all of $R^3$, $R^5$, $R^6$, $R^7$, $R^8$, and $R^9$ are hydrogen. $R^2$ is as defined in Table 1.

Table 13 covers compounds of the following type

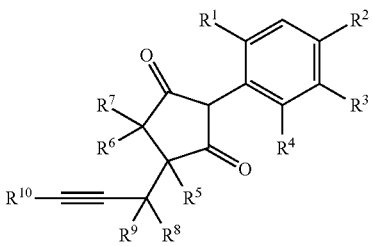

wherein $R^1$ is fluoro, $R^4$ is methoxy, $R^{10}$ is hydrogen and all of $R^3$, $R^5$, $R^6$, $R^7$, $R^8$, and $R^9$ are hydrogen. $R^2$ is as defined in Table 1.

Table 14 covers compounds of the following type

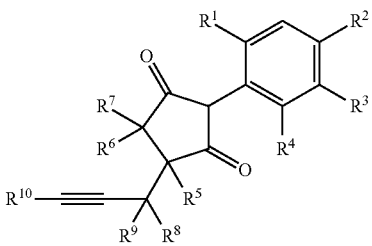

wherein $R^1$ is fluoro, $R^4$ is ethoxy, $R^{10}$ is hydrogen and all of $R^3$, $R^5$, $R^6$, $R^7$, $R^8$, and $R^9$ are hydrogen. $R^2$ is as defined in Table 1.

Table 15 covers compounds of the following type

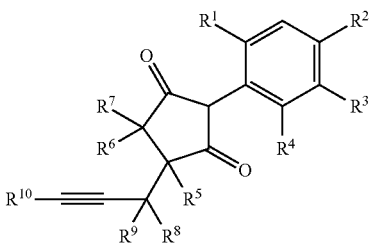

wherein $R^1$ is fluoro, $R^4$ is 2-methoxyethoxy, $R^{10}$ is hydrogen and all of $R^3$, $R^5$, $R^6$, $R^7$, $R^8$, and $R^9$ are hydrogen. $R^2$ is as defined in Table 1.

Table 16 covers compounds of the following type

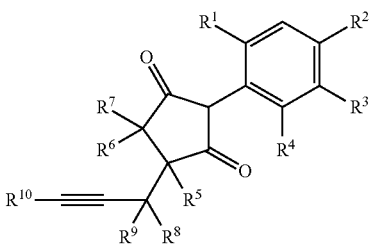

wherein $R^1$ is fluoro, $R^4$ is 2,2,2-trifluoroethoxy, $R^{10}$ is hydrogen and all of $R^3$, $R^5$, $R^6$, $R^7$, $R^8$, and $R^9$ are hydrogen. $R^2$ is as defined in Table 1.

Table 17 covers compounds of the following type

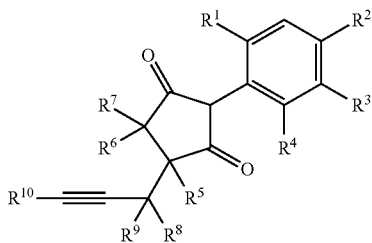

wherein $R^1$ is bromo, $R^4$ is methoxy, $R^{10}$ is hydrogen and all of $R^3$, $R^5$, $R^6$, $R^7$, $R^8$, and $R^9$ are hydrogen. $R^2$ is as defined in Table 1.

Table 18 covers compounds of the following type

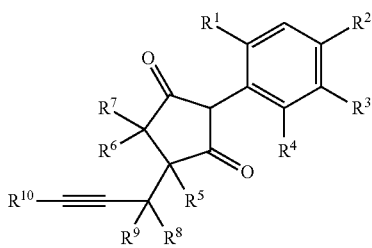

wherein $R^1$ is bromo, $R^4$ is ethoxy, $R^{10}$ is hydrogen and all of $R^3$, $R^5$, $R^6$, $R^7$, $R^8$, and $R^9$ are hydrogen. $R^2$ is as defined in Table 1.

Table 19 covers compounds of the following type

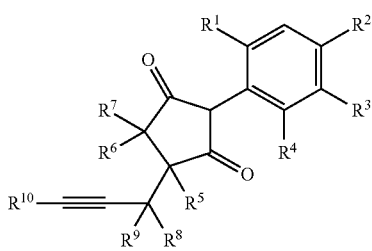

wherein $R^1$ is bromo, $R^4$ is 2-methoxyethoxy, $R^{10}$ is hydrogen and all of $R^3$, $R^5$, $R^6$, $R^7$, $R^8$, and $R^9$ are hydrogen. $R^2$ is as defined in Table 1.

Table 20 covers compounds of the following type

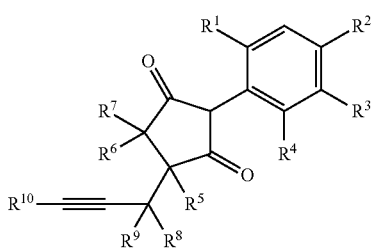

wherein $R^1$ is bromo, $R^4$ is 2,2,2-trifluoroethoxy, $R^{10}$ is hydrogen and all of $R^3$, $R^5$, $R^6$, $R^7$, $R^8$, and $R^9$ are hydrogen. $R^2$ is as defined in Table 1.

Table 21 covers compounds of the following type

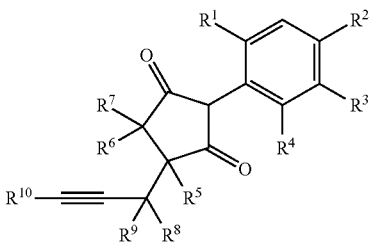

wherein $R^1$ is chloro, $R^4$ is hydrogen, $R^{10}$ is hydrogen and all of $R^3$, $R^5$, $R^6$, $R^7$, $R^8$, and $R^9$ are hydrogen. $R^2$ is as defined in Table 1.

Table 22 covers compounds of the following type

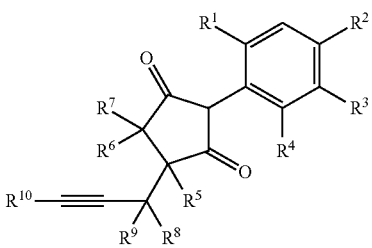

wherein $R^1$ is chloro, $R^4$ is chloro, $R^{10}$ is hydrogen and all of $R^3$, $R^5$, $R^6$, $R^7$, $R^8$, and $R^9$ are hydrogen. $R^2$ is as defined in Table 1.

Table 23 covers compounds of the following type

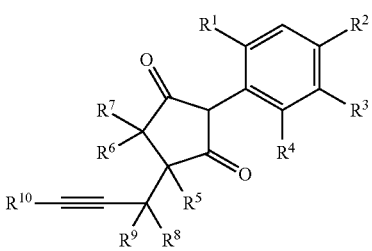

wherein $R^1$ is fluoro, $R^4$ is hydrogen, $R^{10}$ is hydrogen and all of $R^3$, $R^5$, $R^6$, $R^7$, $R^8$, and $R^9$ are hydrogen. $R^2$ is as defined in Table 1.

Table 24 covers compounds of the following type

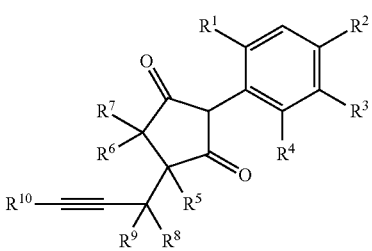

wherein $R^1$ is bromo, $R^4$ is hydrogen, $R^{10}$ is hydrogen and all of $R^3$, $R^5$, $R^6$, $R^7$, $R^8$, and $R^9$ are hydrogen. $R^2$ is as defined in Table 1.

Table 25 covers compounds of the following type

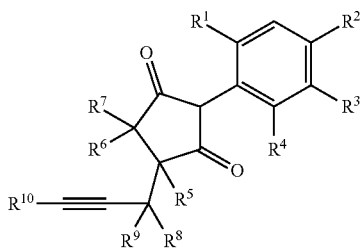

wherein $R^1$ is fluoro, $R^4$ is fluoro, $R^{10}$ is hydrogen and all of $R^3$, $R^5$, $R^6$, $R^7$, $R^8$, and $R^9$ are hydrogen. $R^2$ is as defined in Table 1.

Table 26 covers compounds of the following type

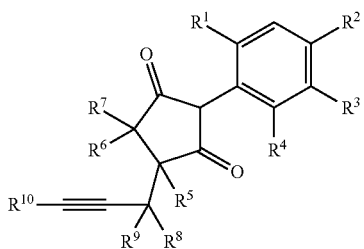

wherein $R^1$ is fluoro, $R^4$ is chloro, $R^{10}$ is hydrogen and all of $R^3$, $R^5$, $R^6$, $R^7$, $R^8$, and $R^9$ are hydrogen. $R^2$ is as defined in Table 1.

Table 27 covers compounds of the following type

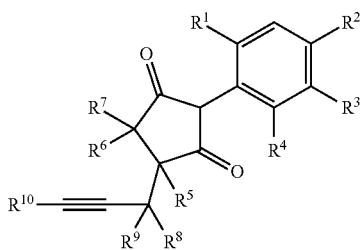

wherein $R^1$ is methyl, $R^4$ is methyl, $R^{10}$ is methyl and all of $R^3$, $R^5$, $R^6$, $R^7$, $R^8$, and $R^9$ are hydrogen. $R^2$ is as defined in Table 1.

Table 28 covers compounds of the following type

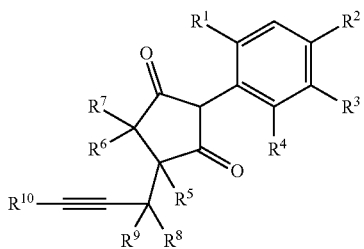

wherein $R^1$ is methyl, $R^4$ is hydrogen, $R^{10}$ is methyl and all of $R^3$, $R^5$, $R^6$, $R^7$, $R^8$, and $R^9$ are hydrogen. $R^2$ is as defined in Table 1.

Table 29 covers compounds of the following type

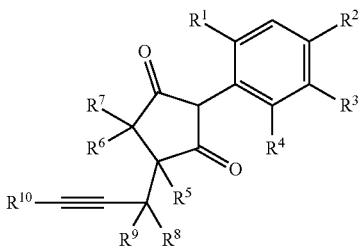

wherein $R^1$ is methyl, $R^4$ is ethyl, $R^{10}$ is methyl and all of $R^3$, $R^5$, $R^6$, $R^7$, $R^8$, and $R^9$ are hydrogen. $R^2$ is as defined in Table 1.

Table 30 covers compounds of the following type

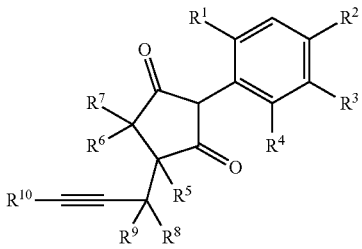

wherein $R^1$ is ethyl, $R^4$ is hydrogen, $R^{10}$ is methyl and all of $R^3$, $R^5$, $R^6$, $R^7$, $R^8$, and $R^9$ are hydrogen. $R^2$ is as defined in Table 1.

Table 31 covers compounds of the following type

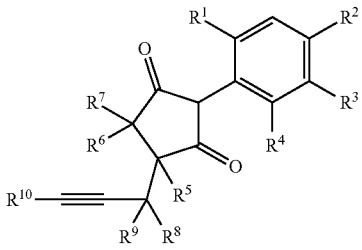

wherein $R^1$ is methyl, $R^4$ is methoxy, $R^{10}$ is methyl and all of $R^3$, $R^5$, $R^6$, $R^7$, $R^8$, and $R^9$ are hydrogen. $R^2$ is as defined in Table 1.

Table 32 covers compounds of the following type

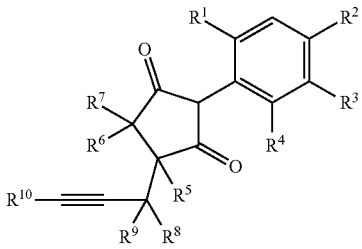

wherein $R^1$ is methyl, $R^4$ is ethoxy, $R^{10}$ is methyl and all of $R^3$, $R^5$, $R^6$, $R^7$, $R^8$, and $R^9$ are hydrogen. $R^2$ is as defined in Table 1.

Table 33 covers compounds of the following type

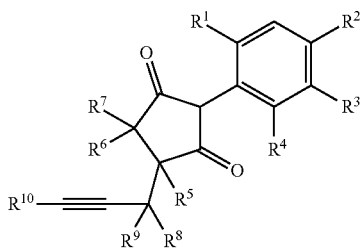

wherein $R^1$ is methyl, $R^4$ is 2-methoxyethoxy, $R^{10}$ is methyl and all of $R^3$, $R^5$, $R^6$, $R^7$, $R^8$, and $R^9$ are hydrogen. $R^2$ is as defined in Table 1.

Table 34 covers compounds of the following type

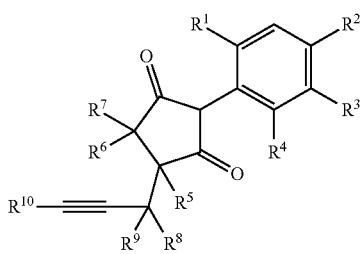

wherein $R^1$ is methyl, $R^4$ is 2,2,2-trifluoroethoxy, $R^{10}$ is methyl and all of $R^3$, $R^5$, $R^6$, $R^7$, $R^8$, and $R^9$ are hydrogen. $R^2$ is as defined in Table 1.

Table 35 covers compounds of the following type

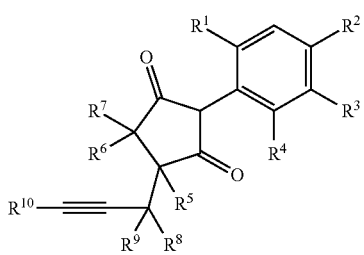

wherein $R^1$ is chloro, $R^4$ is methoxy, $R^{10}$ is methyl and all of $R^3$, $R^5$, $R^6$, $R^7$, $R^8$, and $R^9$ are hydrogen. $R^2$ is as defined in Table 1.

Table 36 covers compounds of the following type

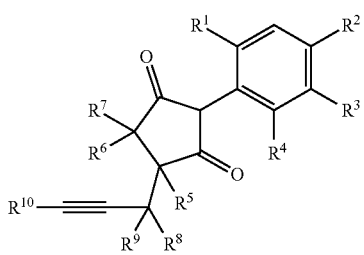

wherein $R^1$ is chloro, $R^4$ is ethoxy, $R^{10}$ is methyl and all of $R^3$, $R^5$, $R^6$, $R^7$, $R^8$, and $R^9$ are hydrogen. $R^2$ is as defined in Table 1.

Table 37 covers compounds of the following type

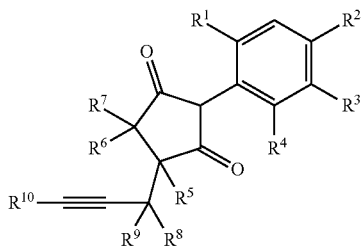

wherein $R^1$ is chloro, $R^4$ is 2-methoxyethoxy, $R^{10}$ is methyl and all of $R^3$, $R^5$, $R^6$, $R^7$, $R^8$, and $R^9$ are hydrogen. $R^2$ is as defined in Table 1.

Table 38 covers compounds of the following type

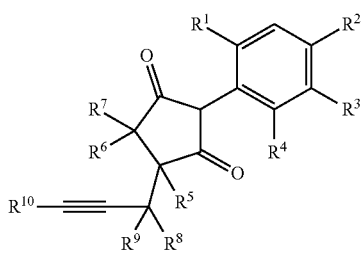

wherein $R^1$ is chloro, $R^4$ is 2,2,2-trifluoroethoxy, $R^{10}$ is methyl and all of $R^3$, $R^5$, $R^6$, $R^7$, $R^8$, and $R^9$ are hydrogen. $R^2$ is as defined in Table 1.

Table 39 covers compounds of the following type

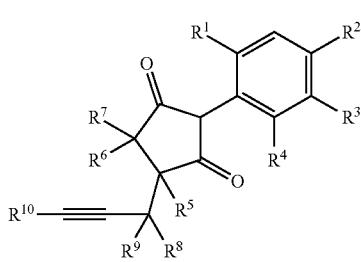

wherein $R^1$ is fluoro, $R^4$ is methoxy, $R^{10}$ is methyl and all of $R^3$, $R^5$, $R^6$, $R^7$, $R^8$, and $R^9$ are hydrogen. $R^2$ is as defined in Table 1.

Table 40 covers compounds of the following type

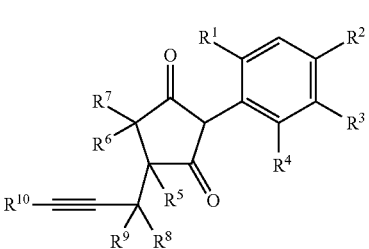

wherein $R^1$ is fluoro, $R^4$ is ethoxy, $R^{10}$ is methyl and all of $R^3$, $R^5$, $R^6$, $R^7$, $R^8$, and $R^9$ are hydrogen. $R^2$ is as defined in Table 1.

Table 41 covers compounds of the following type

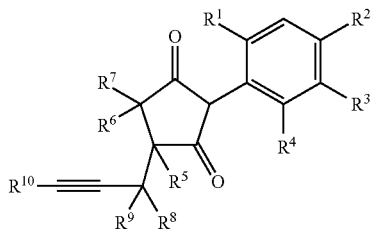

wherein $R^1$ is fluoro, $R^4$ is 2-methoxyethoxy, $R^{10}$ is methyl and all of $R^3$, $R^5$, $R^6$, $R^7$, $R^8$, and $R^9$ are hydrogen. $R^2$ is as defined in Table 1.

Table 42 covers compounds of the following type

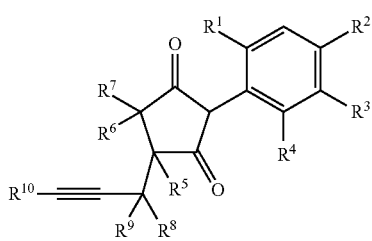

wherein $R^1$ is fluoro, $R^4$ is 2,2,2-trifluoroethoxy, $R^{10}$ is methyl and all of $R^3$, $R^5$, $R^6$, $R^7$, $R^8$, and $R^9$ are hydrogen. $R^2$ is as defined in Table 1.

Table 43 covers compounds of the following type

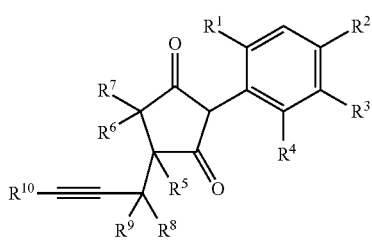

wherein $R^1$ is bromo, $R^4$ is methoxy, $R^{10}$ is methyl and all of $R^3$, $R^5$, $R^6$, $R^7$, $R^8$, and $R^9$ are hydrogen. $R^2$ is as defined in Table 1.

Table 44 covers compounds of the following type

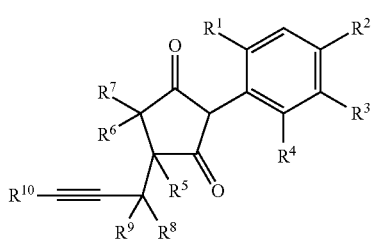

wherein $R^1$ is bromo, $R^4$ is ethoxy, $R^{10}$ is methyl and all of $R^3$, $R^5$, $R^6$, $R^7$, $R^8$, and $R^9$ are hydrogen. $R^2$ is as defined in Table 1.

Table 45 covers compounds of the following type

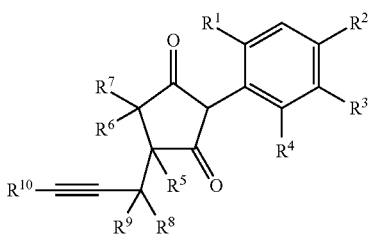

wherein $R^1$ is bromo, $R^4$ is 2-methoxyethoxy, $R^{10}$ is methyl and all of $R^3$, $R^5$, $R^6$, $R^7$, $R^8$, and $R^9$ are hydrogen. $R^2$ is as defined in Table 1.

Table 46 covers compounds of the following type

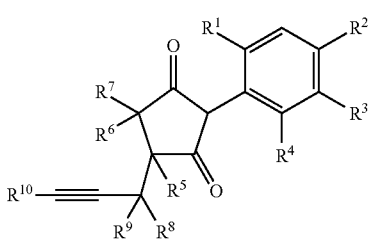

wherein $R^1$ is bromo, $R^4$ is 2,2,2-trifluoroethoxy, $R^{10}$ is methyl and all of $R^3$, $R^5$, $R^6$, $R^7$, $R^8$, and $R^9$ are hydrogen. $R^2$ is as defined in Table 1.

Table 47 covers compounds of the following type

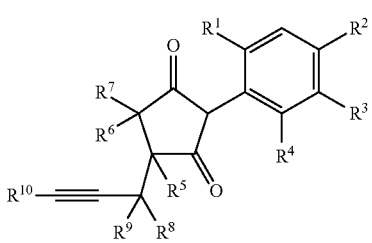

wherein $R^1$ is chloro, $R^4$ is hydrogen, $R^{10}$ is methyl and all of $R^3$, $R^5$, $R^6$, $R^7$, $R^8$, and $R^9$ are hydrogen. $R^2$ is as defined in Table 1.

Table 48 covers compounds of the following type

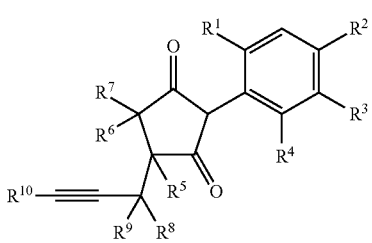

wherein $R^1$ is chloro, $R^4$ is chloro, $R^{10}$ is methyl and all of $R^3$, $R^5$, $R^6$, $R^7$, $R^8$, and $R^9$ are hydrogen. $R^2$ is as defined in Table 1.

Table 49 covers compounds of the following type

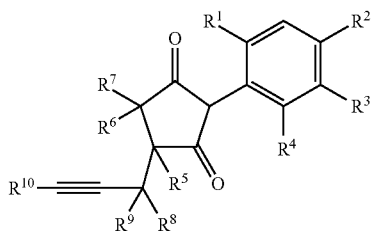

wherein $R^1$ is fluoro, $R^4$ is hydrogen, $R^{10}$ is methyl and all of $R^3$, $R^5$, $R^6$, $R^7$, $R^8$, and $R^9$ are hydrogen. $R^2$ is as defined in Table 1.

Table 50 covers compounds of the following type

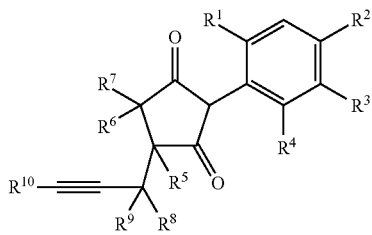

wherein $R^1$ is bromo, $R^4$ is hydrogen, $R^{10}$ is methyl and all of $R^3$, $R^5$, $R^6$, $R^7$, $R^8$, and $R^9$ are hydrogen. $R^2$ is as defined in Table 1.

Table 51 covers compounds of the following type

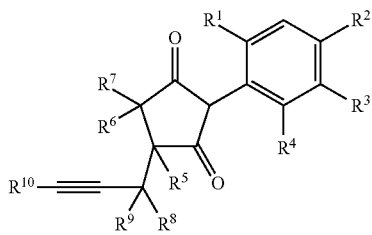

wherein $R^1$ is fluoro, $R^4$ is fluoro, $R^{10}$ is methyl and all of $R^3$, $R^5$, $R^6$, $R^7$, $R^8$, and $R^9$ are hydrogen. $R^2$ is as defined in Table 1.

Table 52 covers compounds of the following type

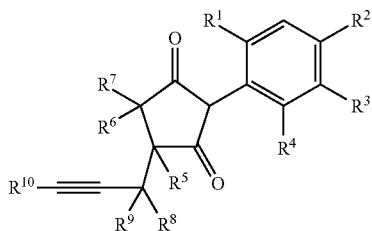

wherein $R^1$ is fluoro, $R^4$ is chloro, $R^{10}$ is methyl and all of $R^3$, $R^5$, $R^6$, $R^7$, $R^8$, and $R^9$ are hydrogen. $R^2$ is as defined in Table 1.

Table 53 covers compounds of the following type

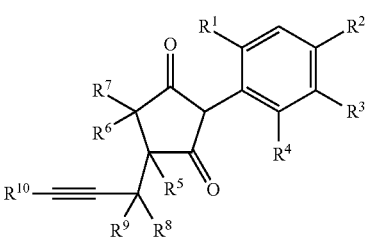

wherein $R^1$ is methyl, $R^4$ is hydrogen, $R^{10}$ is hydrogen and all of $R^2$, $R^5$, $R^6$, $R^7$, $R^8$, and $R^9$ are hydrogen. $R^3$ is as defined in Table 53 below.

TABLE 53

| Compound Number | $R^3$ |
|---|---|
| 53.001 | phenyl |
| 53.002 | 3-fluorophenyl |
| 53.003 | 4-fluorophenyl |
| 53.004 | 3-chlorophenyl |
| 53.005 | 4-chlorophenyl |
| 53.006 | 3-bromophenyl |
| 53.007 | 4-bromophenyl |
| 53.008 | 4-iodophenyl |
| 53.009 | 4-methylphenyl |
| 53.010 | 4-cyanophenyl |
| 53.011 | 4-methoxyphenyl |
| 53.012 | 3-difluoromethoxyphenyl |
| 53.013 | 4-difluoromethoxyphenyl |
| 53.014 | 3-difluoromethylphenyl |
| 53.015 | 4-difluoromethylphenyl |
| 53.016 | 3-trifluoromethylphenyl |
| 53.017 | 4-trifluoromethylphenyl |
| 53.018 | 3-trifluoromethoxyphenyl |
| 53.019 | 4-trifluoromethoxyphenyl |
| 53.020 | 4-methylthiophenyl |
| 53.021 | 4-methylsulfinylphenyl |
| 53.022 | 4-methylsulfonylphenyl |
| 53.023 | 2,4-difluorophenyl |
| 53.024 | 3,4-difluorophenyl |
| 53.025 | 3,5-difluorophenyl |
| 53.026 | 2,4-dichlorophenyl |
| 53.027 | 3,4-dichlorophenyl |
| 53.028 | 4-chloro-2-fluorophenyl |
| 53.029 | 4-chloro-3-fluorophenyl |
| 53.030 | 4-chloro-2-methoxyphenyl |
| 53.031 | 4-chloro-3-methoxyphenyl |
| 53.032 | 4-chloro-2-methylphenyl |
| 53.033 | 4-chloro-3-methylphenyl |
| 53.034 | 2-fluoro-4-cyanophenyl |
| 53.035 | 2-chloropyridin-5-yl |
| 53.036 | 5-chloropyridin-2-yl |
| 53.037 | 3-fluoro-5-chloropyridin-2-yl |
| 53.038 | 5-trifluoromethylpyridin-2-yl |
| 53.039 | 3-chloro-5-trifluoromethylpyridin-2-yl |
| 53.040 | 5-fluoropyridin-2-yl |
| 53.041 | 5-bromopyridin-2-yl |
| 53.042 | 6-chloropyridazin-3-yl |
| 53.043 | 5-bromopyrimidin-2-yl |
| 53.044 | 5-chloropyrimidin-2-yl |
| 53.045 | 5-fluoropyrimidin-2-yl |
| 53.046 | 4-chlorothien-2-yl |
| 53.047 | 5-chlorothien-2-yl |
| 53.048 | 3-chloropyrazol-1-yl |
| 53.049 | 4-chloropyrazol-1-yl |

Table 54 covers compounds of the following type

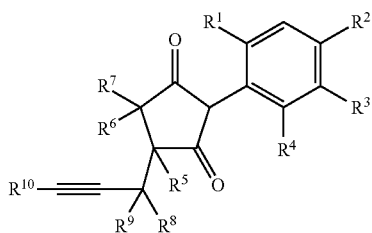

wherein $R^1$ is ethyl, $R^4$ is hydrogen, $R^{10}$ is hydrogen and all of $R^2$, $R^5$, $R^6$, $R^7$, $R^8$, and $R^9$ are hydrogen. $R^3$ is as defined in Table 53.

Table 55 covers compounds of the following type

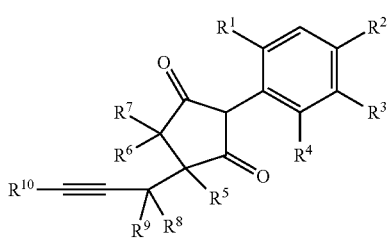

wherein $R^1$ is chloro, $R^4$ is hydrogen, $R^{10}$ is hydrogen and all of $R^2$, $R^5$, $R^6$, $R^7$, $R^8$, and $R^9$ are hydrogen. $R^3$ is as defined in Table 53.

Table 56 covers compounds of the following type

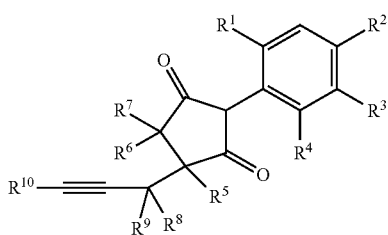

wherein $R^1$ is fluoro, $R^4$ is hydrogen, $R^{10}$ is hydrogen and all of $R^2$, $R^5$, $R^6$, $R^7$, $R^8$, and $R^9$ are hydrogen. $R^3$ is as defined in Table 53.

Table 57 covers compounds of the following type

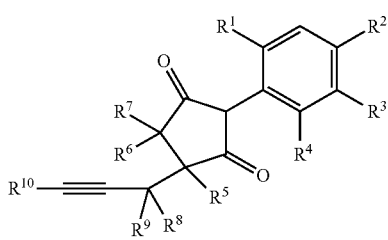

wherein $R^1$ is methyl, $R^4$ is hydrogen, $R^{10}$ is methyl and all of $R^2$, $R^5$, $R^6$, $R^7$, $R^8$, and $R^9$ are hydrogen. $R^3$ is as defined in Table 53.

Table 58 covers compounds of the following type

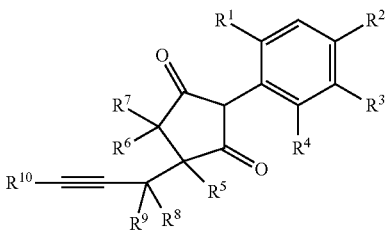

wherein $R^1$ is ethyl, $R^4$ is hydrogen, $R^{10}$ is methyl and all of $R^2$, $R^5$, $R^6$, $R^7$, $R^8$, and $R^9$ are hydrogen. $R^3$ is as defined in Table 53.

Table 59 covers compounds of the following type

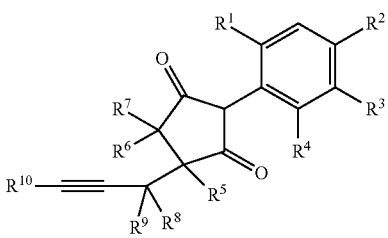

wherein $R^1$ is chloro, $R^4$ is hydrogen, $R^{10}$ is methyl and all of $R^2$, $R^5$, $R^6$, $R^7$, $R^8$, and $R^9$ are hydrogen. $R^3$ is as defined in Table 53.

Table 60 covers compounds of the following type

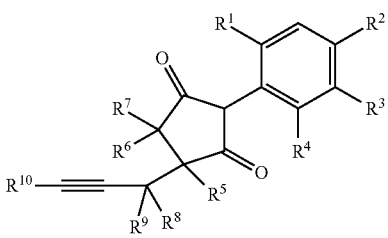

wherein $R^1$ is fluoro, $R^4$ is hydrogen, $R^{10}$ is methyl and all of $R^2$, $R^5$, $R^6$, $R^7$, $R^8$, and $R^9$ are hydrogen. $R^3$ is as defined in Table 53.

BIOLOGICAL EXAMPLES

Biological Example 1 (Biological Examples 1A and 1B)

Test 1—Glasshouse Assay for Herbicidal Activity

Seeds of a variety of test species are sown in standard soil in pots. After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the "technical" (i.e. unformulated) active ingredient in acetone/water (50:50) solution containing 0.5% Tween 20 (polyoxyethylene sorbitan monolaurate, CAS Registry Number 9005-64-5). The test plants are then grown on under controlled conditions in a glasshouse (at 24/16° C., day/night; 14 hours light; 65% humidity) and watered twice daily. After 13 days for pre- or post-emergence, the test is evaluated visually, and an assessed percentage phytotoxicity score is given for each herbicidal application on each plant species (where 100%=total damage to plant; 0%=no damage to plant).

Biological Example 1A—Pre-Emergence Herbicidal Activity

Test plants include the following: *Abutilon theophrasti* (ABUTH), *Amaranthus retroflexus* (AMARE): these are dicotyledonous (broadleaved) weeds. *Setaria faberi* (SETFA), *Alopecurus myosuroides* (ALOMY), *Echinochloa crus-galli* (ECHCG): these are grassy monocotyledonous weeds. Also: *Zea mays* (ZEAMX, corn/maize), which can be a grassy weed ("volunteer" corn) in some circumstances.

Biological Example 1A—Table of Pre-Emergence Herbicidal Activity (Percentage Phytotoxicity)

| Compound Number | Application Rate (g/ha) | ABUTH | AMARE | SETFA | ALOMY | ECHCG | ZEAMX |
|---|---|---|---|---|---|---|---|
| A1  | 250 | -  | 80  | 90  | 100 | 100 | -   |
| A2  | 250 | 50 | 90  | 100 | 90  | 100 | 100 |
| A3  | 250 | 20 | 60  | 100 | 100 | 100 | 100 |
| A4  | 250 | 0  | 80  | 100 | 90  | 100 | 100 |
| A5  | 250 | 70 | 100 | 100 | 100 | 100 | 100 |
| A6  | 250 | 40 | 90  | 100 | 90  | 100 | 90  |
| A7  | 250 | 0  | 70  | 100 | 90  | 100 | 100 |
| A8  | 250 | 0  | 90  | 100 | 90  | 100 | 90  |
| A9  | 250 | 40 | 70  | 100 | 70  | 100 | 80  |
| A10 | 250 | 60 | 100 | 100 | 100 | 100 | 100 |
| A11 | 250 | 40 | 80  | 100 | 100 | 100 | 100 |
| A12 | 250 | 80 | 100 | 100 | 90  | 100 | 100 |
| A13 | 250 | 80 | 100 | 100 | 90  | 100 | 100 |
| A14 | 250 | 20 | 90  | 100 | 100 | 100 | 100 |
| A16 | 250 | 40 | 40  | 90  | 90  | 90  | 80  |
| A17 | 250 | 10 | 10  | 70  | 70  | 70  | 60  |
| A18 | 250 | 20 | 40  | 70  | 60  | 60  | 30  |
| A19 | 250 | 40 | 40  | 60  | 60  | 50  | 0   |
| A20 | 250 | 70 | 70  | 100 | 90  | 100 | 100 |
| A21 | 250 | 10 | 0   | 90  | 80  | 90  | 100 |
| A22 | 250 | 0  | 30  | 90  | 80  | 100 | 100 |
| A23 | 250 | -  | -   | -   | 100 | 100 | -   |
| A24 | 250 | -  | -   | -   | 100 | 100 | -   |
| A25 | 250 | -  | -   | -   | 100 | 100 | -   |
| A26 | 250 | -  | -   | -   | 30  | 80  | -   |
| A27 | 250 | -  | -   | -   | 100 | 100 | -   |
| A28 | 250 | -  | -   | -   | 90  | 100 | -   |
| A29 | 250 | -  | -   | -   | 70  | 90  | -   |
| A42 | 250 | -  | -   | -   | 100 | 80  | -   |
| A45 | 250 | -  | 90  | 60  | 100 | 100 | -   |

Note:
a hyphen (-) in the table above indicates that no measurement was made.

Biological Example 1B—Post-Emergence Herbicidal Activity

Biological Example 1B—Table 1 of Post-Emergence Herbicidal Activity (Percentage Phytotoxicity)

Test plants include the following: *Abutilon theophrasti* (ABUTH) and *Amaranthus retroflexus* (AMARE); these are all dicotyledonous (broadleaved) weeds. *Setaria faberi* (SETFA), *Alopecurus myosuroides* (ALOMY), and *Echinochloa crus-galli* (ECHCG); these are all grassy monocotyledonous weeds. Also: *Zea mays* (ZEAMX, corn/maize), which can be a grassy weed ("volunteer" corn) in some circumstances.

| Compound Number | Application Rate (g/ha) | ABUTH | AMARE | SETFA | ALOMY | ECHCG | ZEAMX |
|---|---|---|---|---|---|---|---|
| A1 | 250  | - | 70 | 100 | 100 | 100 | - |
| A1 | 62.5 | - | 30 | 90  | 90  | 100 | - |

-continued

| Compound Number | Application Rate (g/ha) | ABUTH | AMARE | SETFA | ALOMY | ECHCG | ZEAMX |
|---|---|---|---|---|---|---|---|
| A2 | 250 | 80 | 70 | 100 | 90 | 100 | 100 |
| A2 | 62.5 | 70 | 70 | 100 | 90 | 100 | 100 |
| A3 | 250 | 90 | 90 | 100 | 100 | 100 | 100 |
| A3 | 62.5 | 80 | 60 | 100 | 100 | 100 | 100 |
| A4 | 250 | 80 | 80 | 100 | 100 | 100 | 100 |
| A4 | 30 | 40 | 60 | 100 | 70 | 90 | 100 |
| A5 | 250 | 90 | 90 | 100 | 100 | 100 | 100 |
| A5 | 31.25 | 30 | 30 | 100 | 80 | 100 | 100 |
| A6 | 250 | 70 | 70 | 100 | 100 | 100 | 100 |
| A6 | 30 | 40 | 60 | 100 | 80 | 100 | 100 |
| A7 | 250 | 80 | 80 | 100 | 100 | 100 | 100 |
| A7 | 30 | 30 | 20 | 100 | 70 | 100 | 100 |
| A8 | 250 | 80 | 90 | 100 | 100 | 100 | 100 |
| A8 | 30 | 70 | 80 | 100 | 100 | 100 | 100 |
| A9 | 250 | 80 | 80 | 100 | 100 | 100 | 100 |
| A10 | 250 | 80 | 80 | 100 | 100 | 100 | 100 |
| A10 | 30 | 80 | 80 | 100 | 90 | 100 | 100 |
| A11 | 250 | 80 | 80 | 100 | 100 | 100 | 100 |
| A11 | 30 | 30 | 50 | 100 | 70 | 100 | 100 |
| A12 | 250 | 80 | 80 | 100 | 100 | 100 | 100 |
| A12 | 30 | 50 | 30 | 100 | 80 | 100 | 100 |
| A13 | 250 | 80 | 90 | 100 | 100 | 100 | 100 |
| A13 | 30 | 70 | 60 | 100 | 90 | 100 | 100 |
| A14 | 250 | 0 | 60 | 100 | 90 | 100 | 100 |
| A14 | 62.5 | 0 | 50 | 90 | 70 | 100 | 100 |
| A15 | 250 | 60 | 40 | 70 | 10 | 70 | 80 |
| A16 | 250 | 40 | 60 | 90 | 90 | 100 | 60 |
| A16 | 30 | 40 | 0 | 80 | 70 | 40 | 80 |
| A17 | 250 | 10 | 50 | 80 | 70 | 80 | 60 |
| A18 | 250 | 60 | 60 | 80 | 70 | 80 | 80 |
| A18 | 30 | 0 | 0 | 60 | 10 | 60 | 60 |
| A19 | 250 | 30 | 20 | 90 | 60 | 90 | 30 |
| A19 | 30 | 0 | 0 | 70 | 10 | 70 | 40 |
| A20 | 250 | 60 | 70 | 100 | 100 | 100 | 100 |
| A20 | 30 | 0 | 0 | 80 | 50 | 80 | 90 |
| A21 | 250 | 40 | 30 | 100 | 70 | 100 | 100 |
| A21 | 30 | 0 | 10 | 80 | 40 | 90 | 100 |
| A22 | 250 | 40 | 80 | 100 | 100 | 100 | 100 |
| A22 | 30 | 0 | 10 | 90 | 70 | 90 | 100 |
| A43 | 250 | - | 0 | 70 | 20 | 20 | - |
| A44 | 250 | 10 | 0 | 0 | 0 | 0 | 20 |
| A44 | 8 | 0 | 0 | 0 | 0 | 0 | 30 |
| A45 | 250 | - | 80 | 100 | 100 | 100 | - |
| A45 | 62.5 | - | 20 | 90 | 90 | 100 | - |

Note:
a hyphen (-) in the table above indicates that no measurement was made.

Biological Example 1B—Table 2 of Post-Emergence Herbicidal Activity (Percentage Phytotoxicity)

Test plants include the following:
*Lolium perenne* (LOLPE), *Alopecurus myosuroides* (ALOMY), *Echinochloa crus-galli* (ECHCG), and *Avena fatua* (AVEFA); these are all grassy monocotyledonous weeds. Cool climate crop plant: *Triticum aestivum* (TRZAW, winter wheat).

| Compound Number | Application Rate (g/ha) | LOLPE | TRZAW | ALOMY | ECHCG | AVEFA |
|---|---|---|---|---|---|---|
| A2 | 250 | 100 | 90 | 100 | 100 | 100 |
| A2 | 62.5 | 70 | 70 | 70 | 90 | 80 |
| A3 | 250 | 100 | 90 | 100 | 100 | 100 |
| A3 | 62.5 | 100 | 90 | 100 | 100 | 90 |
| A5 | 250 | 100 | 90 | 100 | 100 | 100 |
| A5 | 62.5 | 90 | 80 | 90 | 100 | 100 |
| A6 | 250 | 80 | 80 | 100 | 100 | 90 |
| A8 | 250 | 100 | 80 | 100 | 100 | 100 |
| A8 | 62.5 | 70 | 80 | 80 | 100 | 90 |

-continued

| Compound Number | Application Rate (g/ha) | LOLPE | TRZAW | ALOMY | ECHCG | AVEFA |
|---|---|---|---|---|---|---|
| A10 | 250 | 100 | 90 | 100 | 100 | 100 |
| A10 | 62.5 | 100 | 90 | 100 | 100 | 100 |
| A12 | 250 | 100 | 80 | 100 | 100 | 100 |
| A12 | 62.5 | 70 | 70 | 60 | 100 | 60 |
| A13 | 250 | 100 | 80 | 100 | 100 | 100 |
| A13 | 62.5 | 90 | 80 | 100 | 100 | 100 |
| A14 | 250 | 80 | 70 | 90 | 100 | 100 |
| A23 | 250 | 100 | 70 | 100 | 100 | 90 |
| A23 | 62.5 | 90 | 50 | 90 | 100 | 90 |
| A24 | 250 | 80 | 0 | 80 | 80 | 50 |
| A24 | 62.5 | 70 | 0 | 60 | 70 | 60 |
| A25 | 250 | 100 | 60 | 100 | 100 | 100 |
| A25 | 62.5 | 100 | 30 | 90 | 100 | 100 |
| A26 | 250 | 100 | 10 | 60 | 100 | 70 |
| A27 | 250 | 100 | 90 | 100 | 100 | 100 |
| A27 | 62.5 | 80 | 80 | 90 | 90 | 90 |
| A28 | 250 | 90 | 80 | 100 | 100 | 90 |
| A28 | 62.5 | 80 | 30 | 70 | 90 | 80 |
| A29 | 250 | 80 | 80 | 80 | 100 | 60 |
| A29 | 62.5 | 60 | 60 | 60 | 90 | 0 |
| A42 | 250 | 100 | 20 | 90 | 100 | 80 |

Biological Example 2

Test 2—Glasshouse Assay for Herbicidal Activity

Seeds of a variety of monocotyledonous and dicotyledonous test plants are sown in standard soil in pots. The plants are cultivated for one day (for pre-emergence) or for about 12 days (for post-emergence) under controlled conditions in a glasshouse (warm climate species at 24/18° C., cool climate species at 20/16° C., both at day/night; 16 hours light; 65% humidity).

An "instant formulation", known as the "IF50", containing 50 g/liter (i.e. 5% w/v) of the "technical" (i.e. unformulated) active ingredient is prepared by dissolving the active ingredient in a mixture of organic solvents and emulsifier, details of which are provided in the Table below. This IF50 is then mixed with a small, variable amount of acetone to aid dissolution, before addition of a 0.2% v/v aqueous solution of the adjuvant X-77 (which is a mixture of alkyl aryl polyoxyethylene glycols and free fatty acids in isopropanol, CAS Registry number 11097-66-8), as the aqueous diluent, to form an aqueous spray solution which contains a predetermined concentration of the active ingredient (which varies depending on the application rate of the active ingredient to the plants) and 0.2% v/v of the adjuvant X-77. This aqueous spray solution is then sprayed onto the plants, after one day's cultivation (for pre-emergence), or after about 12 days' cultivation (range=10-13 days) (for post-emergence).

TABLE

Composition of the mixture of organic solvents and emulsifier to be used as a base for the instant formulation (IF50).

| Component | Supplier | Chemical description | CAS Registry number | Amount/ % w/w |
|---|---|---|---|---|
| Emulsogen EL360 ™ | Clariant | castor oil ethoxylate (as emulsifier) | 61791-12-6 | 11.12 |
| N-methyl-pyrrolidone | widely available | 1-methyl-2-pyrrolidone | 872-50-4 | 44.44 |
| Dowanol DPM ™ glycol ether | Dow | dipropylene glycol monomethyl ether | 34590-94-8 | 44.44 |

The test plants are then grown on, in a glasshouse (greenhouse) under controlled conditions (warm climate species at 24/18° C., cool climate species at 20/16° C., both at day/night; 16 hours light; 65% humidity) and are watered twice daily. 15 days after application of the test herbicide (15DAA) (for post-emergence), and 20 days after application of the test herbicide (20DAA) (for pre-emergence), the test plants are evaluated visually, and an assessed percentage phytotoxicity score is given for each herbicidal application on each plant species (with 100%=total damage to plant; 0%=no damage to plant).

Some of the typical test plants are as follows:

Cool climate crop plants: *Triticum aestivum* (TRZAW, winter wheat), *Brassica napus* (BRSNN, rape, also called oilseed rape or rapeseed), *Beta vulgaris* (BEAVA, sugarbeet). Warm climate crop plants: *Glycine max* (GLXMA, soybean).

Cool climate ("cool season") grassy monocotyledonous weeds: *Alopecurus myosuroides* (ALOMY), *Avena fatua* (AVEFA), *Lolium perenne* (LOLPE).

Warm climate ("warm season") grassy monocotyledonous weeds: *Setaria faberi* (SETFA), *Panicum miliaceum* (PANMI), *Sorghum vulgare* Pers. (SORVU) (or *Sorghum bicolor* (L) Moench ssp. Bicolor), *Digitaria sanguinalis* (DIGSA), *Echinochloa crus-galli* (ECHCG), and *Brachiaria plantaginea* (BRAPL).

Biological Example 2—Table of Pre-Emergence
Herbicidal Activity (Percentage Phytotoxicity)

| Compound Number | Application Rate (g/ha) | LOLPE | SETFA | PANMI | SORVU | DIGSA | ECHCG | BRAPL |
|---|---|---|---|---|---|---|---|---|
| A1  | 125 | 80  | 100 | 100 | 90  | 100 | 90  | 90  |
| A2  | 250 | 80  | 90  | 100 | 80  | 70  | 80  | 80  |
| A3  | 250 | 80  | 80  | 80  | 80  | 90  | 80  | 90  |
| A6  | 250 | 30  | 0   | 0   | 40  | 20  | 50  | -   |
| A7  | 250 | 60  | 90  | 100 | 90  | 100 | 90  | 90  |
| A8  | 250 | 80  | 70  | 90  | 80  | 80  | 60  | -   |
| A10 | 250 | 70  | 100 | 100 | 100 | 100 | 100 | -   |
| A11 | 250 | 60  | 90  | 60  | 80  | 90  | 70  | 100 |
| A12 | 250 | 100 | 100 | 100 | 90  | 100 | 80  | 100 |
| A13 | 250 | 100 | 100 | 100 | 100 | 100 | 100 | 100 |
| A14 | 250 | 70  | 100 | 100 | 90  | 100 | 80  | 100 |
| A15 | 250 | 0   | 20  | 20  | 30  | 50  | 10  | -   |
| A22 | 250 | 20  | 90  | 80  | 70  | 90  | 70  | 90  |
| A23 | 250 | 100 | 90  | 100 | 70  | 90  | 100 | -   |
| A25 | 250 | 90  | 80  | 90  | 90  | 100 | 100 | 100 |
| A42 | 500 | 100 | 80  | 100 | 80  | 70  | 100 | 100 |
| A45 | 125 | 90  | 90  | 100 | 80  | 90  | 80  | 90  |

Note:
a hyphen (-) in the table above indicates that no measurement was made.

Biological Example 2—Table of Post-Emergence
Herbicidal Activity (Percentage Phytotoxicity)

| Compound Number | Application Rate (g/ha) | TRZAW | GLXMA | BRSNN | BEAVA | ALOMY | AVEFA |
|---|---|---|---|---|---|---|---|
| A1  | 125 | 80 | 0  | 70 | 70 | 80  | 100 |
| A1  | 30  | 80 | 0  | 70 | 70 | 60  | 70  |
| A2  | 250 | 90 | 20 | 80 | 50 | 100 | 90  |
| A2  | 30  | 70 | 10 | 50 | 40 | 20  | 60  |
| A3  | 250 | 90 | 70 | 70 | 70 | 100 | 100 |
| A3  | 30  | 80 | 20 | 40 | 40 | 80  | 40  |
| A6  | 250 | 90 | 10 | 40 | 40 | 100 | 80  |
| A6  | 125 | 80 | 10 | 20 | 20 | 80  | 70  |
| A7  | 250 | 90 | 20 | 80 | 70 | 100 | 100 |
| A7  | 30  | 50 | 0  | 60 | 20 | 10  | 20  |
| A8  | 250 | 90 | 40 | 80 | 60 | 80  | 90  |
| A8  | 30  | 30 | 20 | 70 | 10 | 50  | 50  |
| A10 | 250 | 80 | 70 | 80 | 80 | 100 | 100 |
| A10 | 30  | 70 | 40 | 80 | 60 | 50  | 60  |
| A11 | 250 | 90 | 20 | 70 | 70 | 70  | 70  |
| A11 | 30  | 60 | 0  | 30 | 20 | 30  | 20  |
| A12 | 125 | 80 | 0  | 60 | 40 | 80  | 80  |
| A12 | 30  | 40 | 0  | 50 | 40 | 60  | 10  |
| A13 | 125 | 80 | 30 | 80 | 70 | 100 | 80  |
| A13 | 30  | 40 | 20 | 70 | 60 | 30  | 30  |
| A14 | 125 | 40 | 0  | 0  | 10 | 60  | 40  |
| A15 | 250 | 10 | 10 | 60 | 40 | 40  | 10  |
| A18 | 250 | 30 | 40 | 20 | 50 | 30  | 30  |
| A19 | 250 | 30 | 20 | 10 | 0  | 40  | 10  |
| A22 | 125 | 70 | 40 | 70 | 0  | 70  | 70  |
| A22 | 30  | 20 | 0  | 50 | 0  | 50  | 0   |
| A23 | 125 | 20 | 0  | 70 | 30 | 90  | 80  |
| A25 | 125 | 60 | 0  | 20 | 0  | 80  | 100 |
| A25 | 30  | 10 | 0  | 0  | 0  | 50  | 80  |
| A42 | 500 | 10 | 10 | 80 | 30 | 70  | 50  |
| A42 | 125 | 0  | 10 | 20 | 0  | 50  | 0   |
| A45 | 125 | 80 | 10 | 80 | 70 | 90  | 90  |
| A45 | 30  | 80 | 0  | 50 | 70 | 70  | 70  |

| Compound Number | LOLPE | SETFA | PANMI | SORVU | DIGSA | ECHCG | BRAPL |
|---|---|---|---|---|---|---|---|
| A1 | 80 | 100 | 100 | 100 | 100 | 100 | 100 |
| A1 | 70 | 90  | 80  | 90  | 100 | 100 | 100 |
| A2 | 90 | 100 | 100 | 100 | 100 | 100 | 100 |
| A2 | 30 | 100 | 100 | 100 | 100 | 100 | 100 |

-continued

| | | | | | | | |
|---|---|---|---|---|---|---|---|
| A3 | 90 | 100 | 100 | 100 | 100 | 100 | 100 |
| A3 | 30 | 100 | 100 | 100 | 100 | 100 | 80 |
| A6 | 70 | 100 | 100 | 100 | 100 | 100 | - |
| A6 | 30 | 100 | 100 | 100 | 100 | 100 | - |
| A7 | 80 | 100 | 100 | 100 | 100 | 100 | 100 |
| A7 | 30 | 90 | 100 | 100 | 100 | 100 | 100 |
| A8 | 60 | 100 | 100 | 100 | 100 | 100 | - |
| A8 | 40 | 90 | 100 | 100 | 90 | 70 | - |
| A10 | 90 | 100 | 100 | 100 | 100 | 100 | - |
| A10 | 30 | 100 | 100 | 100 | 100 | 100 | - |
| A11 | 40 | 100 | 100 | 100 | 100 | 100 | 100 |
| A11 | 30 | 80 | 100 | 100 | 100 | 100 | 100 |
| A12 | 90 | 100 | 100 | 100 | 100 | 100 | 100 |
| A12 | 30 | 20 | 70 | 90 | 70 | 70 | 70 |
| A13 | 80 | 100 | 100 | 100 | 100 | 100 | 100 |
| A13 | 10 | 100 | 100 | 100 | 100 | 100 | 90 |
| A14 | 20 | 90 | 60 | 100 | 100 | 100 | 30 |
| A15 | 20 | 30 | 70 | 40 | 30 | 70 | - |
| A18 | 10 | 70 | 60 | 70 | 50 | 90 | - |
| A19 | 10 | 60 | 70 | 70 | 70 | 70 | - |
| A22 | 50 | 100 | 100 | 100 | 100 | 100 | 100 |
| A22 | 10 | 80 | 60 | 70 | 70 | 70 | 90 |
| A23 | 90 | 80 | 100 | 90 | 100 | 100 | - |
| A25 | 100 | 100 | 100 | 100 | 100 | 100 | 100 |
| A25 | 90 | 90 | 100 | 100 | 100 | 100 | 100 |
| A42 | 100 | 100 | 100 | 100 | 100 | 100 | 100 |
| A42 | 80 | 90 | 100 | 80 | 90 | 100 | 100 |
| A45 | 100 | 100 | 100 | 100 | 100 | 100 | 100 |
| A45 | 80 | 90 | 100 | 70 | 100 | 100 | 90 |

Note:
a hyphen (-) in the table above indicates that no measurement was made.

Biological Example 3—Assay for Biological Example 3—Glasshouse Assay for Herbicidal Activity, Using Various Adjuvant Systems Materials and Methods Herbicide Application:

Post-emergence foliar spray application, 200 L/ha, usually one or two replicates for the weeds (depending on application rate), and two replicates for soybean.

Climate:

Standard warm conditions (tropical), in glasshouse. Specifically, the glasshouse bay conditions are 24° C./18° C. day/night; 16/8 hours light/dark; 65% humidity.

Plants:

The herbicidal application takes place at the following growth stages for plants which include inter alia one or more of the following plants (usually the herbicidal application takes place on at least the following plants: DIGSA, ELEIN, SETFA, ZEAMX, GLXMA Nikko, and GLXMA TMG133, and often also either BRADC or BRAPP):

Brachiaria decumbens (BRADC)—growth stage (GS) 12 or 13 (or GS 12)—or, if BRADC is not used, then sometimes Brachiaria platyphylla (BRAPP)—growth stage 12 or 13

Digitaria sanguinalis (DIGSA)—growth stage 12 or 13

Eleusine indica (ELEIN)—growth stage 12 or 13

Setaria faberi (SETFA)—growth stage 12 or 13

Echinochloa crus-galli (ECHCG)—growth stage 12 or 13

Sorghum halepense (annual) (SORHA)—growth stage 12 or 13

Panicum dichotomiflorum (PANDI)—growth stage 12 or 13

Zea mays (ZEAMX, maize/corn, e.g. can occur as volunteer corn) cultivar "Garland"—growth stage 12 or 13

Glycine max (GLXMA, soybean) cultivar "Nikko"—growth stage: 1$^{st}$ trifoliate.

Glycine max (GLXMA, soybean) cultivar "TMG133"—which is Roundup Ready™ glyphosate-tolerant soybean cultivar TMG133 (typically available from Monsanto in Brazil)—growth stage: 1$^{st}$ trifoliate.

Herbicidal Compositions Tested:

Each test compound is applied with one of the following adjuvant systems (all percentages are final concentrations in the aqueous spray mixture):

Adjuvant system 1: 0.5% v/v Adigor™*, 1.0% v/v AMS (ammonium sulphate) and 12.5% v/v IPA (isopropyl alcohol).

Adjuvant system 1A: 0.5% v/v Adigor™* and 12.5% v/v IPA (isopropyl alcohol).

Adjuvant system 2: 0.5% v/v Hexamoll™ DINCH**, 1.0% v/v AMS (ammonium sulphate) and 12.5% v/v IPA (isopropyl alcohol).

Adjuvant system 3: 0.5% v/v tris-(2-ethylhexyl)phosphate ("TEHP"), 1.0% v/v AMS (ammonium sulphate) and 12.5% v/v IPA (isopropyl alcohol).

*Adigor™ (currently available in many countries from Syngenta) is an emulsifiable concentrate which consists of:

(i) ethoxylated alcohols, which typically includes ethoxylated higher alcohols (e.g. ethoxylates of alcohols wherein the alcohols are within the range of $C_{12}$-$C_{22}$); and (ii) a mixture of heavy aromatic hydrocarbons, which typically includes (e.g. includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and (iii) about 47% w/w and/or about 45% w/v (with respect to the emulsifiable concentrate) of methylated rapeseed oil (rapeseed oil methyl ester) (e.g. Agnique ME 18 RD-F™), as an adjuvant.

** Hexamoll™ DINCH™ is 1,2-cyclohexane dicarboxylic acid di-isononyl ester

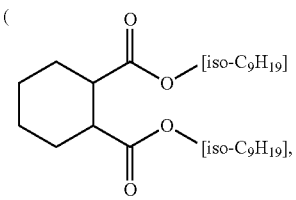

CAS Registry no. 166412-78-8), and is usually available from BASF. "Isononyl" in this context is thought to mean a mixture of two or more branched isomers of $C_9H_{19}$.

Method:

Seeds of the weed (including volunteer) plants, typically including inter alia *Digitaria sanguinalis* (DIGSA), *Eleusine indica* (ELEIN), *Setaria faberi* (SETFA), *Zea mays* (ZEAMX, corn), and sometimes also [either *Brachiaria decumbens* (BRADC) or *Brachiaria platyphylla* (BRAPP)], are sown in seed trays (troughs) containing clay loam soil (pH 7.0, 2.2% organic matter, "Trough Mix A"); and soybean seed is sown in pots containing the same soil with 3 soybean seedlings per pot. The plants are sprayed with the test herbicide when they reach the growth stages mentioned above.

The test herbicidal solutions are prepared by mixing the appropriate aliquots of the test substance(s) and one of the adjuvant systems indicated above *** in deionised water to give the desired treatment concentration.

The herbicidal application is made as a foliar spray, using a tracksprayer. Following the herbicidal application, the plants are watered twice per day for the duration of the test.

A visual assessment of the % herbicidal damage is made 7 and 14 Days After herbicide Application (DAA) (or, in a minority of cases, 7 and 15 DAA), and the results are recorded as % visual herbicidal damage where 0%=no damage to plants and 100%=plant totally killed.

***Adjuvant system=either Adigor™ or Hexamoll DINCH™ or tris-(2-ethylhexyl)phosphate each at 0.5% v/v, and 12.5% v/v IPA (isopropyl alcohol), and 1.0% v/v AMS (ammonium sulphate); or 0.5% v/v Adigor™ and 12.5% v/v IPA (isopropyl alcohol); all percentages are final concentrations in the aqueous spray mixture.

Biological Example 3—Post-Emergence Activity—Results at 14 or 15 Days After Herbicide Application Compounds A2, A7, A11, A12, A14, A20 and A21, which are compounds of formula (I) according to the present invention, were tested in a test method substantially as described above.

Compounds A2 and A7 were tested using the 0.5% v/v Hexamoll™ DINCH™+1.0% v/v AMS+12.5% v/v IPA adjuvant system. Compounds A11, A12, A14, A20 and A21 were tested using the 0.5% v/v tris-(2-ethylhexyl)phosphate ("TEHP")+1.0% v/v AMS+12.5% v/v IPA adjuvant system.

The percentages of herbicidal damage/plant control, at 14 Days After herbicide Application (DAA) (or, in some cases, at 15 DAA), for the Compounds tested and for some of the plants tested, were in the following percentage ranges. For the tested compounds, the phytotoxicity results shown herein are generally the average of 2 or 3 repetitions (for the grassy weeds including corn) or the average of 2 repetitions (for soybean for most of the tested compounds). However, for Compound A2 on soybean there was 1 repetion only.

Control of *Brachiaria decumbens* (BRADC), a Warm-Climate (Warm-Season) Grassy Weed At 14 DAA, Compound A2 showed a percentage control of (phytotoxicity on) *Brachiaria decumbens* (BRADC) of 50% (as an average of 2 repetitions), when applied post-emergence at an application rate of 8 g/ha.

At 14 DAA, Compound A7 showed a percentage control of *Brachiaria decumbens* of 95% (as an average of 3 repetitions), when applied post-emergence at an application rate of 8 g/ha.

At 14 DAA, Compound A11 showed a percentage control of *Brachiaria decumbens* of 99% (as an average of 2 repetitions), when applied post-emergence at an application rate of 8 g/ha.

At 14 or 15 DAA, Compound A12 showed a percentage control of *Brachiaria decumbens* (BRADC) of 99%, when applied post-emergence at an application rate of 8 g/ha.

Control of *Digitaria sanguinalis* (DIGSA), a Warm-Climate (Warm-Season) Grassy Weed At 14 DAA, Compound A2 showed a percentage control of (phytotoxicity on) *Digitaria sanguinalis* (DIGSA) of 90% (as an average of 2 repetitions), when applied post-emergence at an application rate of 8 g/ha.

At 14 DAA, Compound A7 showed a percentage control of *Digitaria sanguinalis* of 95% (as an average of 3 repetitions), when applied post-emergence at an application rate of 8 g/ha.

At 14 DAA, Compound A11 showed a percentage control of *Digitaria sanguinalis* of 99% (as an average of 2 repetitions), when applied post-emergence at an application rate of 8 g/ha.

At 14 or 15 DAA, Compound A12 showed a percentage control of *Digitaria sanguinalis* of 98.5%, when applied post-emergence at an application rate of 8 g/ha.

At 15 DAA, Compound A14 showed a percentage control of *Digitaria sanguinalis* of 85% (as an average of 2 repetitions), when applied post-emergence at an application rate of 8 g/ha.

At 14 or 15 DAA, Compound A20 showed a percentage control of *Digitaria sanguinalis* of 75%, when applied post-emergence at an application rate of 8 g/ha.

At 14 or 15 DAA, Compound A21 showed a percentage control of *Digitaria sanguinalis* of 45%, when applied post-emergence at an application rate of 8 g/ha.

Control of *Eleusine indica* (ELEIN), a Warm-Climate (Warm-Season) Grassy Weed

At 14 DAA, Compound A2 showed a percentage control of (phytotoxicity on) *Eleusine indica* (ELEIN) of 85% (as an average of 2 repetitions), when applied post-emergence at an application rate of 8 g/ha.

At 14 DAA, Compound A7 showed a percentage control of *Eleusine indica* of 91.7% (as an average of 3 repetitions), when applied post-emergence at an application rate of 8 g/ha.

At 14 DAA, Compound A11 showed a percentage control of *Eleusine indica* of 95% (as an average of 2 repetitions), when applied post-emergence at an application rate of 8 g/ha.

At 14 or 15 DAA, Compound A12 showed a percentage control of *Eleusine indica* of 90%, when applied post-emergence at an application rate of 8 g/ha.

At 15 DAA, Compound A14 showed a percentage control of *Eleusine indica* of 20% (as an average of 2 repetitions), when applied post-emergence at an application rate of 8 g/ha.

At 14 or 15 DAA, Compound A20 showed a percentage control of *Eleusine indica* of 15%, when applied post-emergence at an application rate of 8 g/ha.

At 14 or 15 DAA, Compound A21 showed a percentage control of *Eleusine indica* of 25%, when applied post-emergence at an application rate of 8 g/ha.

Control of *Setaria faberi* (SETFA), a Warm-Climate (Warm-Season) Grassy Weed

At 14 DAA, Compound A2 showed a percentage control of (phytotoxicity on) *Setaria faberi* (SETFA) of 90% (as an average of 2 repetitions), when applied post-emergence at an application rate of 8 g/ha.

At 14 DAA, Compound A7 showed a percentage control of *Setaria faberi* of 91.7% (as an average of 3 repetitions), when applied post-emergence at an application rate of 8 g/ha.

At 14 DAA, Compound A11 showed a percentage control of *Setaria faberi* of 98% (as an average of 2 repetitions), when applied post-emergence at an application rate of 8 g/ha.

At 14 or 15 DAA, Compound A12 showed a percentage control of *Setaria faberi* of 95%, when applied post-emergence at an application rate of 8 g/ha.

At 15 DAA, Compound A14 showed a percentage control of *Setaria faberi* of 95% (as an average of 2 repetitions), when applied post-emergence at an application rate of 8 g/ha.

At 14 or 15 DAA, Compound A20 showed a percentage control of *Setaria faberi* of 90%, when applied post-emergence at an application rate of 8 g/ha.

At 14 or 15 DAA, Compound A21 showed a percentage control of *Setaria faberi* of 85%, when applied post-emergence at an application rate of 8 g/ha.

Control of *Zea mays* (ZEAMX, Corn), a Warm-Climate (Warm-Season) Grassy Plant

*Zea mays* (ZEAMX, maize, corn) is often present as a "volunteer" weed ("volunteer" corn) in fields where it was planted as a crop in preceding growing season(s) and where the present field crop is not corn.

At 14 DAA, Compound A2 showed a percentage control of (phytotoxicity on) *Zea mays* (ZEAMX, maize, corn) of 10% (as an average of 2 repetitions), when applied post-emergence at an application rate of 8 g/ha.

At 14 DAA, Compound A7 showed a percentage control of *Zea mays* of 100% (as an average of 3 repetitions), when applied post-emergence at an application rate of 8 g/ha.

At 14 DAA, Compound A11 showed a percentage control of *Zea mays* of 100% (as an average of 2 repetitions), when applied post-emergence at an application rate of 8 g/ha.

At 14 or 15 DAA, Compound A12 showed a percentage control of *Zea mays* of 100%, when applied post-emergence at an application rate of 8 g/ha.

At 15 DAA, Compound A14 showed a percentage control of *Zea mays* of 90% (as an average of 2 repetitions), when applied post-emergence at an application rate of 8 g/ha.

At 14 or 15 DAA, Compound A20 showed a percentage control of *Zea mays* of 90%, when applied post-emergence at an application rate of 8 g/ha.

At 14 or 15 DAA, Compound A21 showed a percentage control of *Zea mays* of 95%, when applied post-emergence at an application rate of 8 g/ha.

Phytotoxicity on *Glycine max* (GLXMA, Soybean) Cultivar "Nikko"

At 14 DAA, Compound A2 showed a percentage phytotoxicity on *Glycine max* cultivar "Nikko" of 10% (1 repetition only), when applied post-emergence at an application rate of 120 g/ha.

At 14 DAA, Compound A7 showed a percentage phytotoxicity on *Glycine max* cultivar "Nikko" of 2.5% (as an average of 2 repetitions), when applied post-emergence at an application rate of 120 g/ha.

At 14 DAA, Compound A11 showed a percentage phytotoxicity on *Glycine max* cultivar "Nikko" of 15% (as an average of 2 repetitions), when applied post-emergence at an application rate of 120 g/ha.

At 14 or 15 DAA, Compound A12 showed a percentage phytotoxicity on *Glycine max* cultivar "Nikko" of 15%, when applied post-emergence at an application rate of 240 g/ha.

At 15 DAA, Compound A14 showed a percentage phytotoxicity on *Glycine max* cultivar "Nikko" of 5% (as an average of 2 repetitions), when applied post-emergence at an application rate of 120 g/ha.

At 14 or 15 DAA, Compound A20 showed a percentage phytotoxicity on *Glycine max* cultivar "Nikko" of 2%, when applied post-emergence at an application rate of 120 g/ha.

At 14 or 15 DAA, Compound A21 showed a percentage phytotoxicity on *Glycine max* cultivar "Nikko" of 5%, when applied post-emergence at an application rate of 120 g/ha.

Phytotoxicity on *Glycine max* (GLXMA, Soybean) Cultivar "TMG133"

*Glycine max* (GLXMA, soybean) cultivar "TMG133" is Roundup Ready™ glyphosate-tolerant soybean cultivar TMG133, and is typically available from Monsanto in Brazil.

At 14 DAA, Compound A2 showed a percentage phytotoxicity on *Glycine max* cultivar "TMG133" of 20% (1 repetition only), when applied post-emergence at an application rate of 120 g/ha.

At 14 DAA, Compound A7 showed a percentage phytotoxicity on *Glycine max* cultivar "TMG133" of 0% (as an average of 2 repetitions), when applied post-emergence at an application rate of 120 g/ha.

At 14 DAA, Compound A11 showed a percentage phytotoxicity on *Glycine max* cultivar "TMG133" of 12.5% (as an average of 2 repetitions), when applied post-emergence at an application rate of 120 g/ha.

At 14 or 15 DAA, Compound A12 showed a percentage phytotoxicity on *Glycine max* cultivar "TMG133" of 15%, when applied post-emergence at an application rate of 240 g/ha.

At 15 DAA, Compound A14 showed a percentage phytotoxicity on *Glycine max* cultivar "TMG133" of 5% (as an average of 2 repetitions), when applied post-emergence at an application rate of 120 g/ha.

At 14 or 15 DAA, Compound A20 showed a percentage phytotoxicity on *Glycine max* cultivar "TMG133" of 10%, when applied post-emergence at an application rate of 120 g/ha.

At 14 or 15 DAA, Compound A21 showed a percentage phytotoxicity on *Glycine max* cultivar "TMG133" of 5%, when applied post-emergence at an application rate of 120 g/ha.

The invention claimed is:
1. A compound of formula (I):

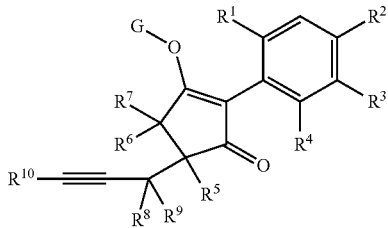

wherein:
R$^1$ is methyl, ethyl, n-propyl, cyclopropyl, trifluoromethyl, vinyl, ethynyl, fluorine, chlorine, bromine, methoxy, difluoromethoxy or trifluoromethoxy; and
either (a): R$^2$ is R$^{2A}$ and R$^3$ is R$^{3A}$;
or (b): R$^2$ is R$^{2B}$ and R$^3$ is R$^{3B}$;
wherein:
R$^{3A}$ is hydrogen, methyl, fluorine or chlorine; and
R$^{2A}$ is hydrogen, methyl, ethyl, n-propyl, isopropyl, cyclopropyl, C$_1$-C$_2$fluoroalkyl, vinyl, prop-1-enyl, —C≡C—R$^{2AA}$, halogen, or (C$_1$-C$_2$fluoroalkyl)-methoxy-; wherein R$^{2AA}$ is hydrogen, fluorine, trifluoromethyl, ethyl or cyclopropyl;
or R$^{2A}$ is phenyl optionally substituted by 1, 2 or 3 substituents independently being halogen, C$_1$-C$_2$alkyl, C$_1$-C$_2$fluoroalkyl, methoxymethyl, vinyl, ethynyl, C$_1$-C$_3$alkoxy, C$_1$-C$_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
or R$^{2A}$ is monocyclic heteroaryl optionally substituted by 1, 2 or 3 substituents independently being halogen, C$_1$-C$_2$alkyl, C$_1$-C$_2$fluoroalkyl, methoxymethyl, vinyl, ethynyl, C$_1$-C$_3$alkoxy, C$_1$-C$_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
and wherein
R$^{2B}$ is hydrogen, methyl or fluorine; and
either R$^{3B}$ is phenyl optionally substituted by 1, 2 or 3 substituents independently being halogen, C$_1$-C$_2$alkyl, C$_1$-C$_2$fluoroalkyl, methoxymethyl, vinyl, ethynyl, C$_1$-C$_2$alkoxy, C$_1$-C$_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
or R$^{3B}$ is monocyclic heteroaryl optionally substituted by 1, 2 or 3 substituents independently being halogen, C$_1$-C$_2$alkyl, C$_1$-C$_2$fluoroalkyl, methoxymethyl, vinyl, ethynyl, C$_1$-C$_2$alkoxy, C$_1$-C$_2$fluoroalkoxy, methylthio, methylsulfinyl, methylsulfonyl, cyano or nitro, provided that either one or none (i.e. no more than one) of these optional substituents are methoxymethyl, vinyl, ethynyl, methylthio, methylsulfinyl, methylsulfonyl or nitro;
and wherein
R$^4$ is hydrogen, methyl, ethyl, n-propyl, cyclopropyl, trifluoromethyl, vinyl, ethynyl, fluorine, chlorine, bromine, C$_1$-C$_3$alkoxy, C$_1$-C$_2$fluoroalkoxy, C$_1$-C$_2$alkoxy-C$_1$-C$_3$alkoxy-, or C$_1$fluoroalkoxy-C$_1$-C$_3$alkoxy-; and
R$^5$, R$^6$ and R$^7$, independently of each other, are hydrogen, C$_1$-C$_5$alkyl, C$_2$-C$_3$ alkenyl, C$_2$-C$_3$alkynyl, C$_1$-C$_2$fluoroalkyl or C$_1$-C$_2$alkoxyC$_1$-C$_2$alkyl;
provided that: either (i) at least two of R$^5$, R$^6$ and R$^7$ are hydrogen, or (ii) two of R$^5$, R$^6$ and R$^7$ are methyl and the remaining one of R$^5$, R$^6$ and R$^7$ is hydrogen; and
R$^8$ and R$^9$, independently of each other, are hydrogen, fluorine or C$_1$-C$_3$alkyl; and
R$^{10}$ is hydrogen or methyl;
and wherein:
G is hydrogen; an agriculturally acceptable metal, or an agriculturally acceptable sulfonium or ammonium group; or
G is —C(X$^a$)—R$^a$, C(X$^b$)—X$^c$—R$^b$, C(X$^d$)—N(R$^c$)—R$^d$, —SO$_2$—R$^e$, —P(X$^e$)(R$^f$)—R$^g$, CH$_2$—X$^f$—R$^h$; or
phenyl-CH$_2$— or phenyl-CH(C$_1$-C$_2$alkyl)- (in each of which the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or heteroaryl-CH$_2$— or heteroaryl-CH(C$_1$-C$_2$alkyl)- (in each of which the heteroaryl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro), or phenyl-C(O)—CH$_2$— (wherein the phenyl is optionally substituted by 1, 2 or 3 of, independently, C$_1$-C$_2$alkyl, C$_1$fluoroalkyl, C$_1$-C$_2$alkoxy, C$_1$fluoroalkoxy, fluorine, chlorine, bromine, cyano or nitro); or C$_1$-C$_6$alkoxy-C(O)—CH$_2$—, C$_1$-C$_6$alkyl-C(O)—CH$_2$—, C$_1$-C$_6$alkoxy-C(O)—CH=CH—, C$_2$-C$_7$alken-1-yl-CH$_2$—, C$_2$-C$_7$alken-1-yl-CH(C$_1$-C$_2$alkyl)-, C$_2$-C$_4$fluoroalken-1-yl-CH$_2$—, C$_2$-C$_7$alkyn-1-yl-CH$_2$—, or C$_2$-C$_7$alkyn-1-yl-CH(C$_1$-C$_2$alkyl)-;
wherein X$^a$, X$^b$, X$^c$, X$^d$, X$^e$ and X$^f$ are independently of each other oxygen or sulfur; and wherein
R$^a$ is H, C$_1$-C$_{21}$alkyl, C$_2$-C$_{21}$alkenyl, C$_2$-C$_{18}$ alkynyl, C$_1$-C$_{10}$fluoroalkyl, C$_1$-C$_{10}$cyanoalkyl, C$_1$-C$_{10}$nitroalkyl, C$_1$-C$_{10}$aminoalkyl, C$_1$-C$_5$alkylamino(C$_1$-C$_5$)alkyl, C$_2$-C$_8$dialkylamino(C$_1$-C$_5$)alkyl, C$_3$-C$_7$cycloalkyl(C C$_1$-C$_5$alkoxy(C$_1$-C$_5$)alkyl, C$_3$-C$_5$alkenyloxy(C$_1$-C$_5$)alkyl, C$_3$-C$_5$alkynyloxy (C$_1$-C$_5$)alkyl, C$_1$-C$_5$alkylthio(C$_1$-C$_5$)alkyl, C$_1$-C$_5$alkylsulfinyl(C$_1$-C$_5$)alkyl, C$_1$-C$_5$alkylsulfonyl (C$_1$-C$_5$)alkyl, C$_2$-C$_8$alkylideneaminoxy(C$_1$-C$_5$)alkyl, C$_1$-C$_5$alkylcarbonyl(C$_1$-C$_5$)alkyl, C$_1$-C$_5$alkoxycarbonyl(C$_1$-C$_5$)alkyl, aminocarbonyl(C$_1$-C$_5$)alkyl, C$_1$-C$_5$alkylaminocarbonyl(C$_1$-C$_5$)alkyl, C$_2$-C$_8$dialkylaminocarbonyl(C$_1$-C$_5$)alkyl, C$_1$-C$_5$alkylcarbonylamino(C$_1$-C$_5$)alkyl, N—(C$_1$-C$_5$)alkylcarbonyl-N—(C$_1$-C$_5$)alkylamino(C$_1$-C$_5$)alkyl, C$_3$-C$_6$trialkylsilyl(C$_1$-C$_5$)alkyl, phenyl(C$_1$-C$_5$)alkyl (wherein the phenyl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), heteroaryl(C$_1$-C$_5$)alkyl (wherein the heteroaryl is optionally substituted by 1, 2 or 3 of, independently, C$_1$-C$_3$alkyl, C$_1$-C$_3$fluoroalkyl, C$_1$-C$_3$alkoxy, C$_1$-C$_3$fluoroalkoxy, C$_1$-C$_3$alkylthio, C$_1$-C$_3$alkylsulfinyl, C$_1$-C$_3$alkylsulfonyl, halogen, cyano, or nitro), C$_2$-C$_5$fluoroalkenyl, C$_3$-C$_8$cycloalkyl;

phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present as an agrochemically acceptable salt thereof.

2. The compound as claimed in claim 1, wherein G is hydrogen; an agriculturally acceptable metal, or an agriculturally acceptable sulfonium or ammonium group; or G is —C($X^a$)—$R^a$ or —C($X^b$)—$X^c$—$R^b$.

3. The compound as claimed in claim 1, wherein $X^a$, $X^b$ and $X^c$ are oxygen;

$R^a$ is $C_1$-$C_{10}$alkyl, $C_2$-$C_6$alkenyl, $C_2$-$C_6$alkynyl, $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$ fluoroalkyl, $C_1$-$C_2$alkoxy, $C_1$ fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; and $R^b$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl, $C_3$-$C_6$cycloalkyl-methyl-, $C_1$-$C_4$alkoxy$C_1$-$C_4$alkyl, phenyl-methyl- (in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano); phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano.

4. The compound as claimed in claim 1, wherein $R^1$ is methyl, ethyl, ethynyl, fluorine, chlorine, bromine, methoxy, difluoromethoxy or trifluoromethoxy.

5. The compound as claimed in claim 1, wherein $R^1$ is methyl, fluorine or chlorine.

6. The compound as claimed in claim 1, wherein $R^2$ is $R^{2A}$ and $R^3$ is $R^{3A}$.

7. The compound as claimed in claim 1, wherein $R^{3A}$ is hydrogen.

8. The compound as claimed in claim 1, wherein:
   $R^{2A}$ is methyl, ethyl, vinyl, prop-1-enyl, —C≡C—$R^{2AA}$, halogen, or $C_1$fluoroalkyl-methoxy-;
   or $R^{2A}$ is phenyl optionally substituted by 1, 2 or 3 substituents independently being halogen, $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro;
   or $R^{2A}$ is monocyclic 6-membered or 5-membered heteroaryl optionally substituted by 1, 2 or 3 substituents independently being halogen, $C_1$-$C_2$alkyl, $C_1$-$C_2$fluoroalkyl, $C_1$-$C_2$alkoxy, $C_1$-$C_2$fluoroalkoxy, cyano or nitro, provided that either one or none (i.e. no more than one) of these optional substituents are $C_1$-$C_2$alkyl, $C_1$-$C_2$alkoxy or nitro.

9. The compound as claimed in claim 1, wherein:
   when $R^{2A}$ is optionally substituted phenyl, then $R^{2A}$ is of sub-formula (a) or (a1):

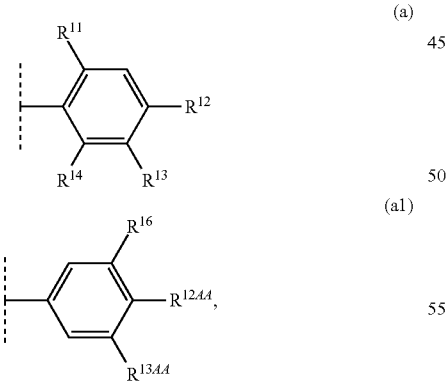

in which:
$R^{11}$ is hydrogen, fluorine or chlorine;
$R^{12}$ is halogen, $C_1$-$C_2$alkyl, $C_1$-$C_2$fluoroalkyl, $C_1$-$C_2$alkoxy, $C_1$-$C_2$fluoroalkoxy, cyano or nitro;
$R^{13}$ is hydrogen, halogen, $C_1$-$C_2$alkyl, $C_1$-$C_2$fluoroalkyl, $C_1$-$C_2$alkoxy, $C_1$-$C_2$fluoroalkoxy, cyano or nitro; and
$R^{14}$ is hydrogen, halogen, $C_1$-$C_2$alkyl, $C_1$-$C_2$fluoroalkyl, $C_1$-$C_2$alkoxy, $C_1$-$C_2$fluoroalkoxy, cyano or nitro;
provided that one or more of $R^{11}$, $R^{13}$ and $R^{14}$ are hydrogen; and provided that either one or none (i.e. no more than one) of $R^{12}$, $R^{13}$ and $R^{14}$ are $C_1$-$C_2$alkyl, $C_1$-$C_2$alkoxy or nitro; and
$R^{12AA}$ is hydrogen, fluorine or chlorine;
$R^{13AA}$ is fluorine or chlorine; and
$R^{16}$ is hydrogen, fluorine or chlorine;
provided that when $R^{12AA}$ is fluorine or chlorine, then $R^{16}$ is fluorine or chlorine; and
provided that either one or none (i.e. no more than one) of $R^{13AA}$ and $R^{16}$ are chlorine;
and wherein, when $R^{2A}$ is optionally substituted monocyclic heteroaryl, then $R^{2A}$ is of sub-formula (b), (c), (d), (e), (f) or (g):

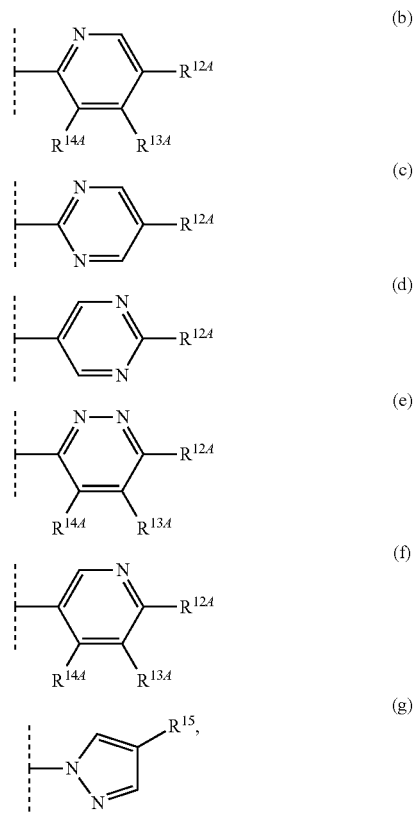

in which:
$R^{12A}$ is halogen, $C_1$-$C_2$alkyl, $C_1$-$C_2$fluoroalkyl, $C_1$-$C_2$alkoxy, $C_1$-$C_2$fluoroalkoxy, cyano or nitro;
$R^{13A}$ is hydrogen, halogen, $C_1$-$C_2$alkyl, $C_1$-$C_2$fluoroalkyl, $C_1$-$C_2$alkoxy, $C_1$-$C_2$fluoroalkoxy, cyano or nitro; and
$R^{14A}$ is hydrogen, halogen, $C_1$-$C_2$alkyl, $C_1$-$C_2$fluoroalkyl, $C_1$-$C_2$alkoxy, $C_1$-$C_2$fluoroalkoxy, cyano or nitro;
provided that either one or none (i.e. no more than one) of $R^{12A}$, $R^{13A}$ and $R^{14A}$ are $C_1$-$C_2$alkyl, $C_1$-$C_2$alkoxy or nitro;
and $R^{15}$ is hydrogen, halogen, methyl, $C_1$fluoroalkyl, $C_1$fluoroalkoxy, or cyano.

10. The compound as claimed in claim 9, wherein:
when $R^{2A}$ is optionally substituted phenyl, then $R^{2A}$ is of sub-formula (a), wherein:
$R^{11}$ is hydrogen;
$R^{12}$ is fluorine, chlorine, bromine, $C_1$fluoroalkyl, $C_1$fluoroalkoxy, or cyano;

$R^{13}$ is hydrogen, fluorine or chlorine; and
$R^{14}$ is hydrogen, fluorine, chlorine, bromine, or $C_1$fluoroalkyl;
and when $R^{2A}$ is optionally substituted monocyclic heteroaryl, then $R^{2A}$ is of sub-formula (b), (c), or (g), wherein:
$R^{12A}$ is fluorine, chlorine, bromine, $C_1$fluoroalkyl, $C_1$fluoroalkoxy, or cyano;
$R^{13A}$ is hydrogen, fluorine or chlorine; and
$R^{14A}$ is hydrogen, fluorine, chlorine, bromine, or $C_1$fluoroalkyl; and
$R^{15}$ is hydrogen, fluorine, chlorine, methyl, $C_1$fluoroalkyl, or $C_1$fluoroalkoxy.

11. The compound as claimed in claim 1, wherein:
when $R^{3B}$ is optionally substituted phenyl, then $R^{3B}$ is of sub-formula (a2):

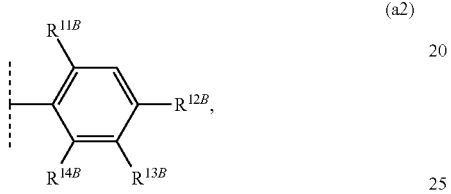
(a2)

in which
$R^{11B}$ is hydrogen, fluorine, chlorine, methyl or methoxy;
$R^{12B}$ is fluorine, chlorine, $C_1$fluoroalkyl, methoxy or $C_1$fluoroalkoxy;
$R^{13B}$ is hydrogen or fluorine; and
$R^{14B}$ is hydrogen or fluorine;
provided that one or more of $R^{11B}$, $R^{13B}$ and $R^{14B}$ are hydrogen;
and wherein, when $R^{3B}$ is optionally substituted monocyclic heteroaryl, then $R^{3B}$ is of sub-formula (b1) or (c1):

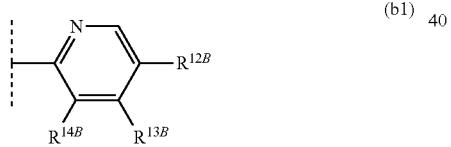
(b1)

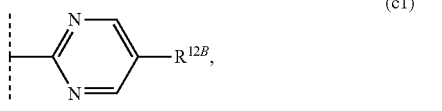
(c1)

in which:
$R^{12B}$ is fluorine, chlorine, $C_1$fluoroalkyl, methoxy or $C_1$fluoroalkoxy;
$R^{13B}$ is hydrogen or fluorine; and
$R^{14B}$ is hydrogen, fluorine or chlorine.

12. The compound as claimed in claim 1, wherein:
$R^{3B}$ is of sub-formula (a2):

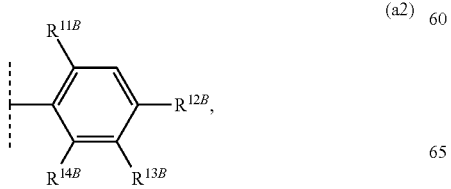
(a2)

$R^{11B}$ is hydrogen, fluorine, chlorine, methyl or methoxy,
$R^{12B}$ is fluorine, chlorine, $C_1$fluoroalkyl, methoxy or $C_1$fluoroalkoxy,
$R^{13B}$ is hydrogen or fluorine, and
$R^{14B}$ is hydrogen or fluorine,
provided that one or more of $R^{11B}$, $R^{13B}$ and $R^{14B}$ are hydrogen;
and $R^{2B}$ is hydrogen.

13. A compound as claimed in claim 1, wherein:
$R^1$ is methyl, fluorine, chlorine, bromine, difluoromethoxy or trifluoromethoxy; and
either (a): $R^2$ is $R^{2A}$ and $R^3$ is $R^{3A}$;
or (b): $R^2$ is $R^{2B}$ and $R^3$ is $R^{3B}$;
and wherein:
$R^{3A}$ is hydrogen or methyl; and
$R^{2A}$ is methyl, —C≡C—$R^{2AA}$ chlorine or bromine;
or $R^{2A}$ is of sub-formula (a) or (a1):

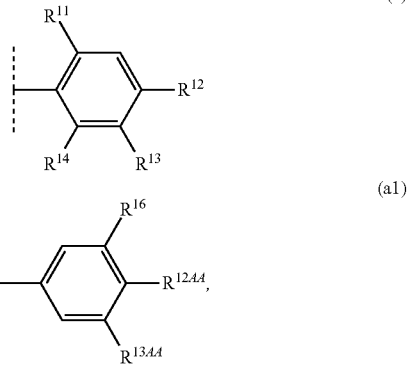
(a)

(a1)

in which:
$R^{11}$ is hydrogen, fluorine or chlorine,
$R^{12}$ is halogen, $C_1$-$C_2$alkyl, $C_1$-$C_2$fluoroalkyl, $C_1$-$C_2$alkoxy, $C_1$-$C_2$fluoroalkoxy, cyano or nitro,
$R^{13}$ is hydrogen, halogen, $C_1$-$C_2$alkyl, $C_1$-$C_2$fluoroalkyl, $C_1$-$C_2$alkoxy, $C_1$-$C_2$fluoroalkoxy, cyano or nitro, and
$R^{14}$ is hydrogen, halogen, $C_1$-$C_2$alkyl, $C_1$-$C_2$fluoroalkyl, $C_1$-$C_2$alkoxy, $C_1$-$C_2$fluoroalkoxy, cyano or nitro,
provided that one or more of $R^{11}$, $R^{13}$ and $R^{14}$ are hydrogen; and provided that either one or none (i.e. no more than one) of $R^{12}$, $R^{13}$ and $R^{14}$ are $C_1$-$C_2$alkyl, $C_1$-$C_2$alkoxy or nitro, and
$R^{12AA}$ is hydrogen, fluorine or chlorine,
$R^{13AA}$ is fluorine or chlorine, and
$R^{16}$ is hydrogen, fluorine or chlorine,
provided that when $R^{12AA}$ is fluorine or chlorine, then $R^{16}$ is fluorine or chlorine, and
provided that either one or none (i.e. no more than one) of $R^{13AA}$ and $R^{16}$ are chlorine;
or $R^{2A}$ is of sub-formula (b), (c), (d), (e), (f) or (g):

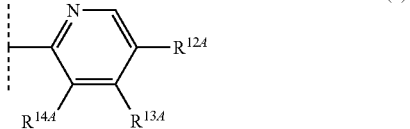
(b)

-continued

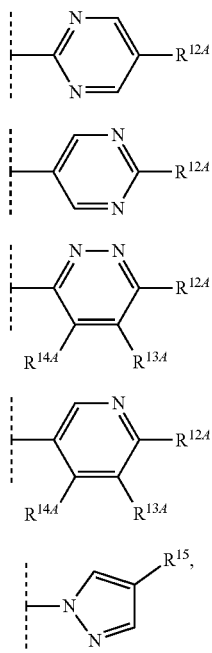

in which:
R$^{12A}$ is halogen, C$_1$-C$_2$alkyl, C$_1$-C$_1$fluoroalkyl, C$_1$-C$_2$alkoxy, C$_1$-C$_1$fluoroalkoxy, cyano or nitro,
R$^{13A}$ is hydrogen, halogen, C$_1$-C$_2$alkyl, C$_1$-C$_2$fluoroalkyl, C$_1$-C$_2$alkoxy, C$_1$-C$_2$fluoro alkoxy, cyano or nitro, and
R$^{14A}$ is hydrogen, halogen, C$_1$-C$_2$alkyl, C$_1$-C$_2$fluoroalkyl, C$_1$-C$_2$alkoxy, C$_1$-C$_2$fluoroalkoxy, cyano or nitro,
provided that either one or none (i.e. no more than one) of R$^{12A}$, R$^{13A}$ and R$^{14A}$ are C$_1$-C$_2$alkyl, C$_1$-C$_2$alkoxy or nitro, and
R$^{15}$ is hydrogen, halogen, methyl, C$_1$fluoroalkyl, C$_1$fluoroalkoxy, or cyano;
and R$^{2B}$ is hydrogen or methyl; and
either R$^{3B}$ is of sub-formula (a2):

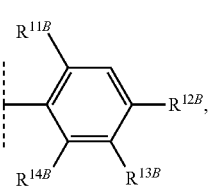

in which
R$^{11B}$ is hydrogen, fluorine, chlorine, methyl or methoxy,
R$^{12B}$ is fluorine, chlorine, C$_1$fluoroalkyl, methoxy or C$_1$fluoroalkoxy,
R$^{13B}$ is hydrogen or fluorine, and
R$^{14B}$ is hydrogen or fluorine,
provided that one or more of R$^{11B}$, R$^{13B}$ and R$^{14B}$ are hydrogen, or R$^{3B}$ is of sub-formula (b1) or (c1):

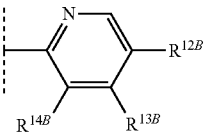

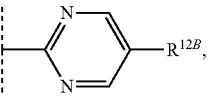

in which:
R$^{12B}$ is fluorine, chlorine, C$_1$fluoroalkyl, methoxy or C$_1$fluoroalkoxy,
R$^{13B}$ is hydrogen or fluorine, and
R$^{14B}$ is hydrogen, fluorine or chlorine;
and wherein:
when R$^2$ is R$^{2A}$ and R$^3$ is R$^{3A}$, then R$^4$ is methyl, ethyl, ethynyl, fluorine, chlorine, methoxy, ethoxy, n-propoxy, C$_1$-C$_2$fluoroalkoxy, or MeO—CH$_2$—CH$_2$—O—;
and, when R$^2$ is R$^{2B}$ and R$^3$ is R$^{3B}$, then R$^4$ is hydrogen, methyl, fluorine or chlorine.

14. The compound as claimed in claim 13, wherein:
when R$^2$ is R$^{2A}$ and R$^3$ is R$^{3A}$, then R$^4$ is methyl, chlorine or methoxy;
and when R$^2$ is R$^{2B}$ and R$^3$ is R$^{3B}$, then R$^4$ is hydrogen.

15. The compound as claimed in claim 1, wherein all of R$^5$, R$^6$ and R$^7$ are hydrogen.

16. The compound as claimed in claim 1, wherein R$^8$ and R$^9$ are both hydrogen.

17. The compound as claimed in claim 1, wherein R$^{10}$ is hydrogen.

18. The compound as claimed in claim 1, wherein the compound of formula (I) is a compound of formula (IC):

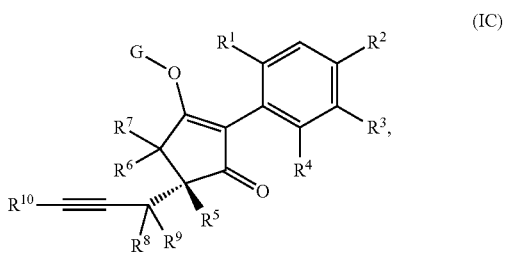

and wherein 40% or more by molarity of the compound of formula (IC) has the indicated stereochemistry at the ring-carbon atom bonded to R$^5$ and —CR$^8$R$^9$—C≡C—R$^{10}$.

19. The compound as claimed in claim 1, which is any of compounds:
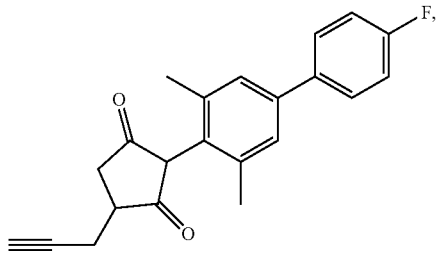
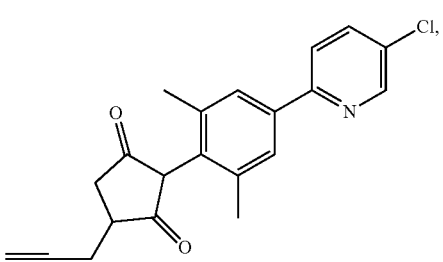
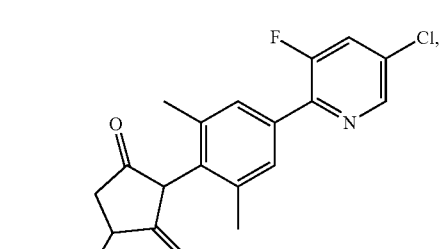
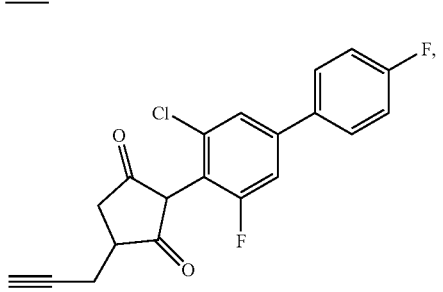
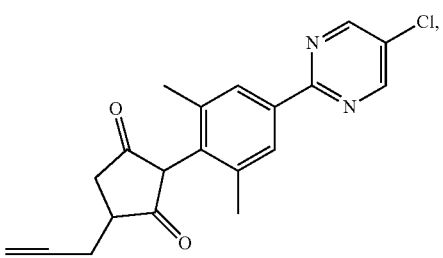
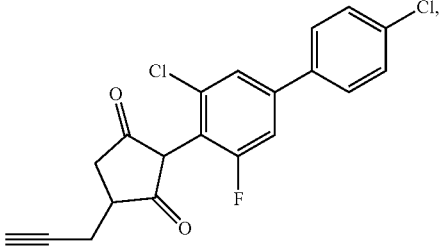
-continued
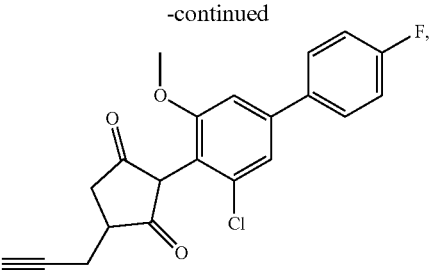
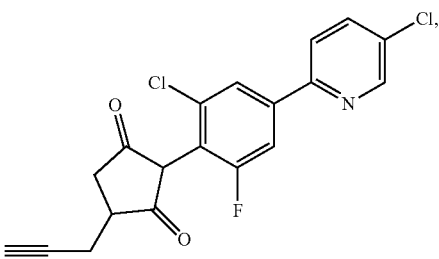
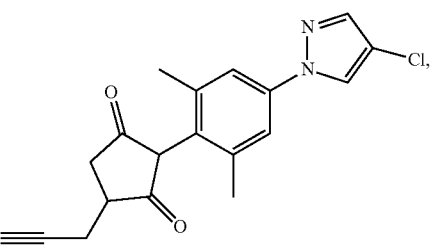
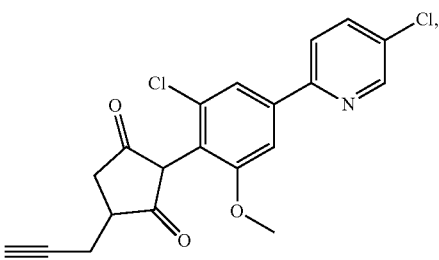
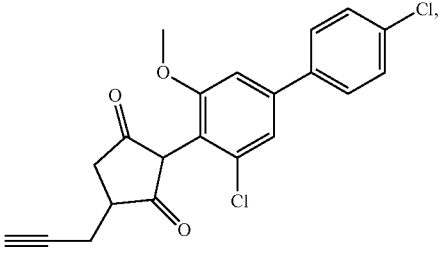
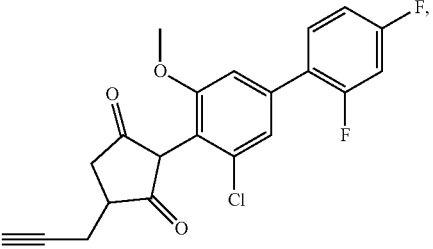

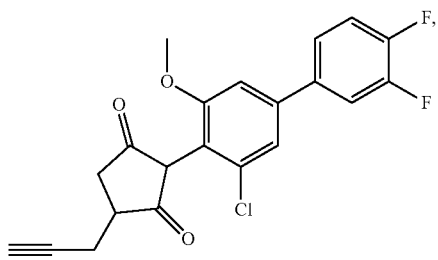
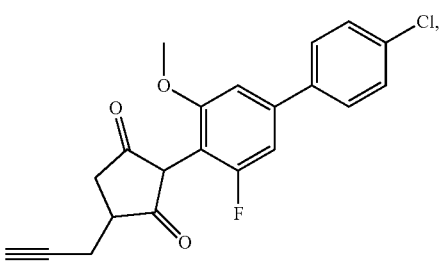
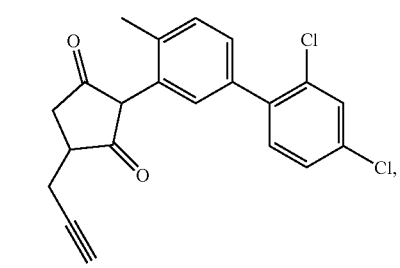
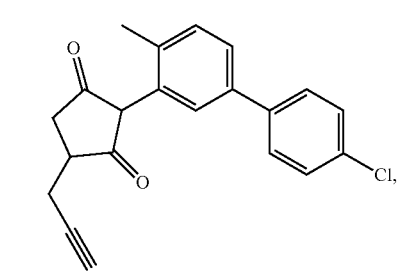
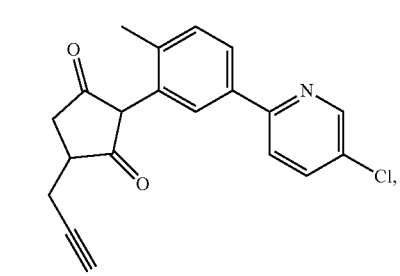
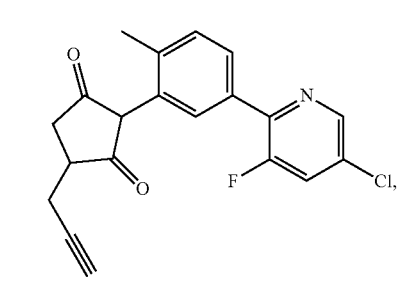
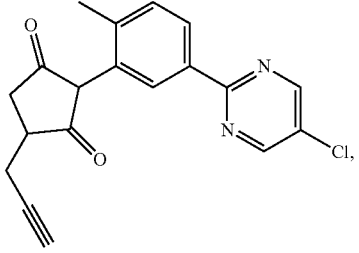
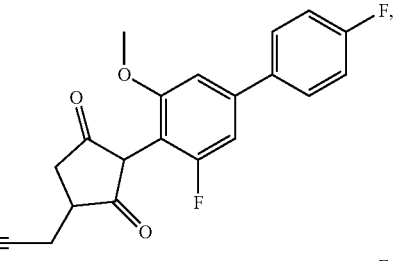
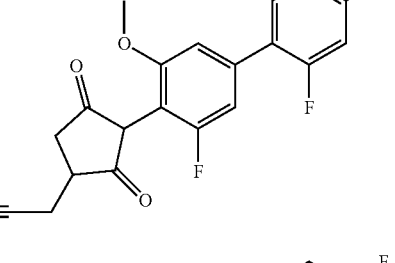
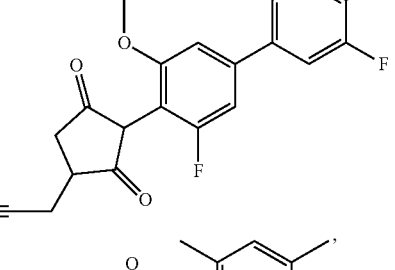
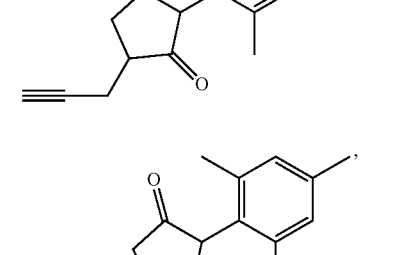
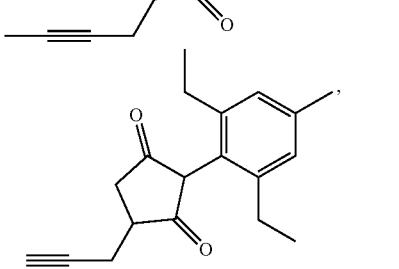

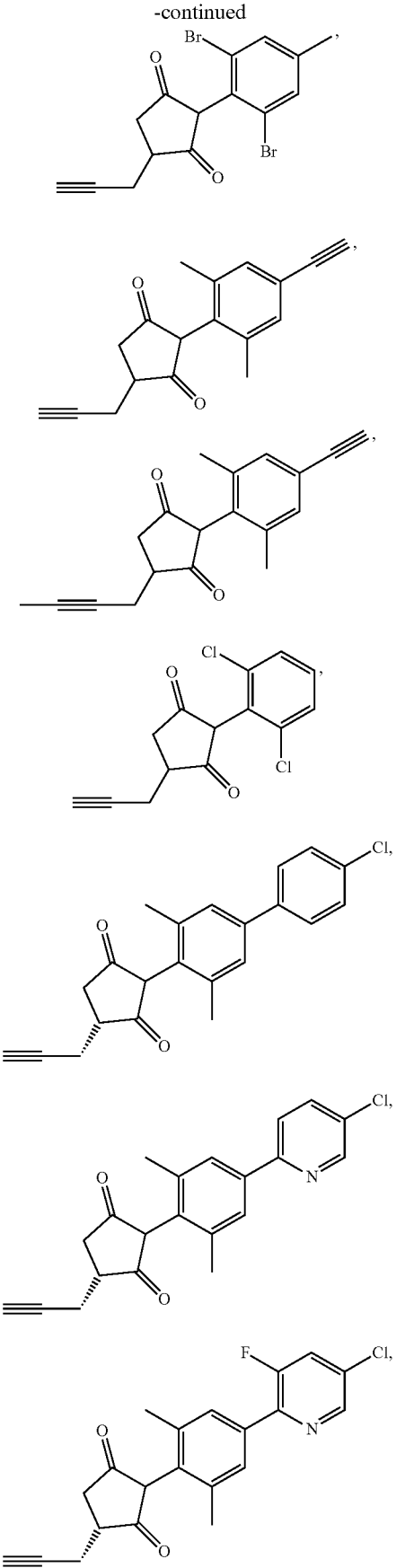
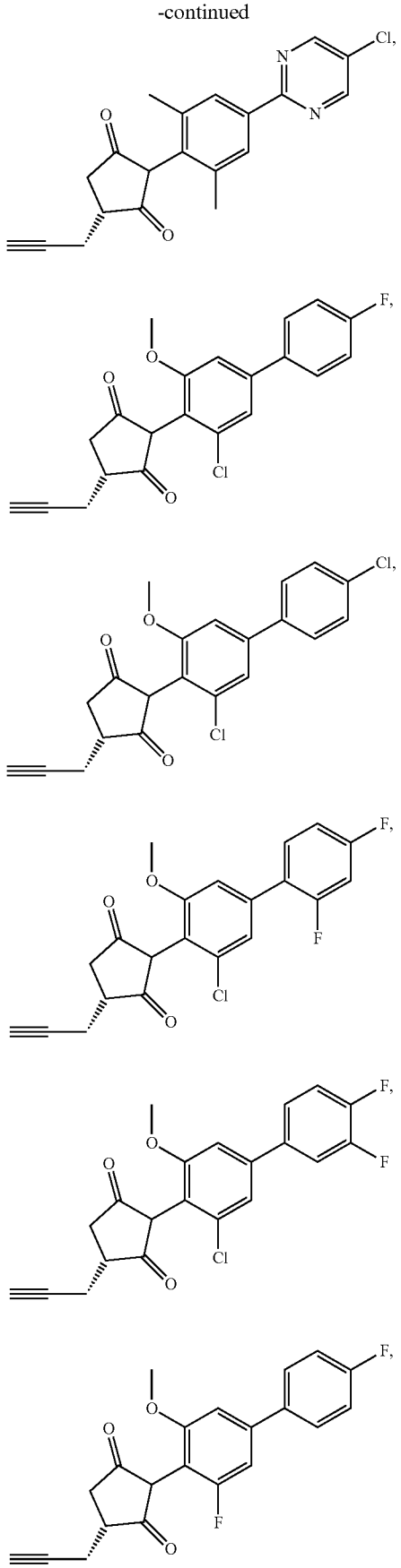

-continued

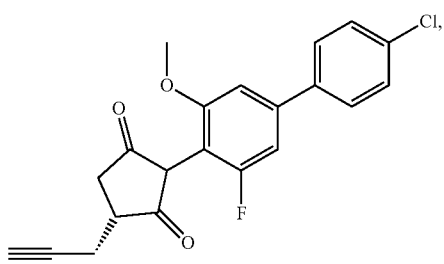

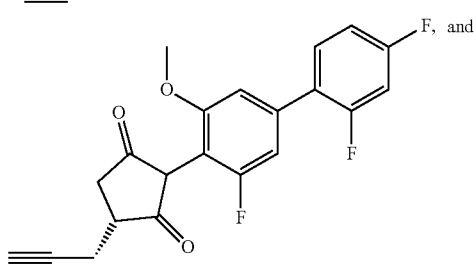

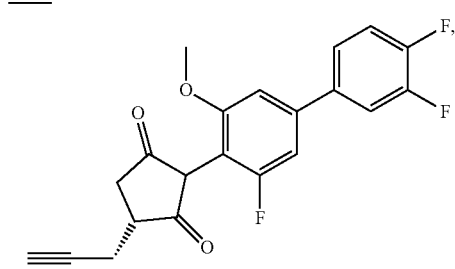

present either as a free compound and/or present as an agrochemically acceptable salt thereof.

20. The compound as claimed in claim 1, wherein the compound has the formula:

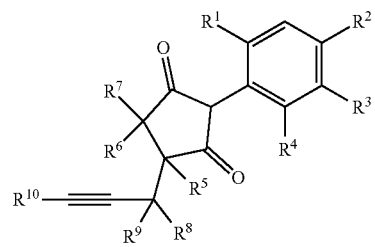

wherein $R^1$ is methyl, $R^4$ is methyl, $R^{10}$ is hydrogen and $R^3$, $R^5$, $R^6$, $R^7$, $R^8$, and $R^9$ are hydrogen, or

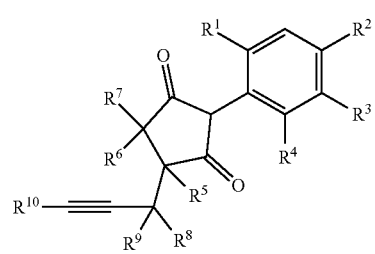

wherein $R^1$ is methyl, $R^4$ is hydrogen, $R^{10}$ is hydrogen and all of $R^3$, $R^5$, $R^6$, $R^7$, $R^8$, and $R^9$ are hydrogen, or

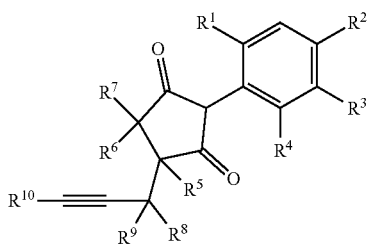

wherein $R^1$ is methyl, $R^4$ is ethyl, $R^{10}$ is hydrogen and all of $R^3$, $R^5$, $R^6$, $R^7$, $R^8$, and $R^9$ are hydrogen, or wherein $R^1$ is ethyl, $R^4$ is hydrogen, $R^{10}$ is hydrogen and all of $R^3$, $R^5$, $R^6$, $R^7$, $R^8$, and $R^9$ are hydrogen, or wherein $R^1$ is methyl, $R^4$ is methoxy, $R^{10}$ is hydrogen and all of $R^3$, $R^5$, $R^6$, $R^7$, $R^8$, and $R^9$ are hydrogen, or wherein $R^1$ is methyl, $R^4$ is ethoxy, $R^{10}$ is hydrogen and all of $R^3$, $R^5$, $R^6$, $R^7$, $R^8$, and $R^9$ are hydrogen, or wherein $R^1$ is methyl, $R^4$ is 2-methoxyethoxy, $R^{10}$ is hydrogen and all of $R^3$, $R^5$, $R^6$, $R^7$, $R^8$, and $R^9$ are hydrogen, or

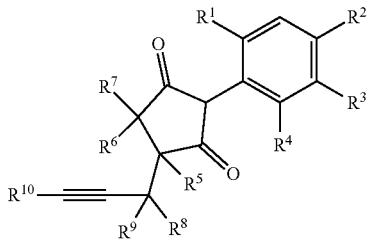

wherein $R^1$ is methyl, $R^4$ is 2,2,2-trifluoroethoxy, $R^{10}$ is hydrogen and all of $R^3$, $R^5$, $R^6$, $R^7$, $R^8$, and $R^9$ are hydrogen, or

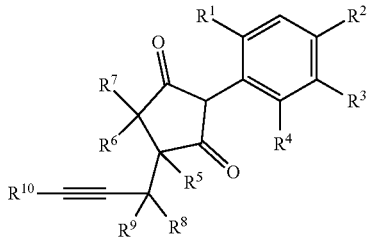

wherein $R^1$ is chloro, $R^4$ is methoxy, $R^{10}$ is hydrogen and all of $R^3$, $R^5$, $R^6$, $R^7$, $R^8$, and $R^9$ are hydrogen, or

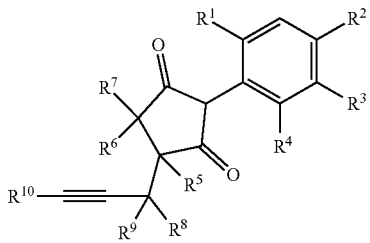

wherein $R^1$ is chloro, $R^4$ is ethoxy, $R^{10}$ is hydrogen and all of $R^3$, $R^5$, $R^6$, $R^7$, $R^8$, and $R^9$ are hydrogen, or

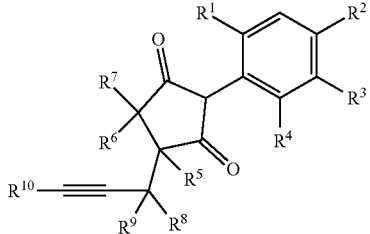

wherein $R^1$ is chloro, $R^4$ is 2-methoxyethoxy, $R^{10}$ is hydrogen and all of $R^3$, $R^5$, $R^6$, $R^7$, $R^8$, and $R^9$ are hydrogen

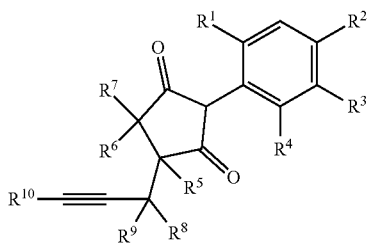

wherein $R^1$ is chloro, $R^4$ is 2,2,2-trifluoroethoxy, $R^{10}$ is hydrogen and all of $R^3$, $R^5$, $R^6$, $R^7$, $R^8$, and $R^9$ are hydrogen, or

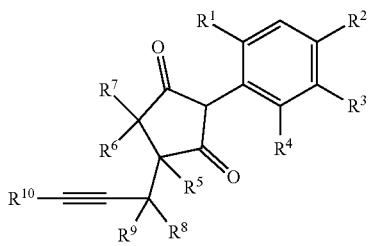

wherein $R^1$ is fluoro, $R^4$ is methoxy, $R^{10}$ is hydrogen and all of $R^3$, $R^5$, $R^6$, $R^7$, $R^8$, and $R^9$ are hydrogen, or

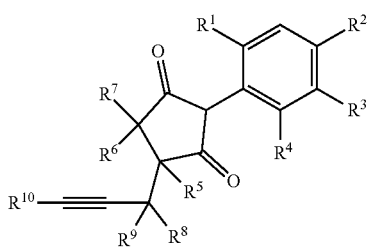

wherein $R^1$ is fluoro, $R^4$ is ethoxy, $R^{10}$ is hydrogen and all of $R^3$, $R^5$, $R^6$, $R^7$, $R^8$, and $R^9$ are hydrogen

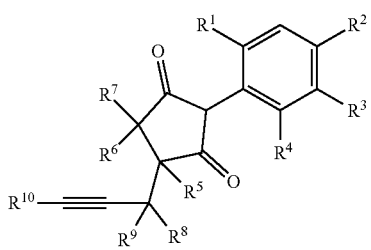

wherein $R^1$ is fluoro, $R^4$ is 2-methoxyethoxy, $R^{10}$ is hydrogen and all of $R^3$, $R^5$, $R^6$, $R^7$, $R^8$, and $R^9$ are hydrogen, or

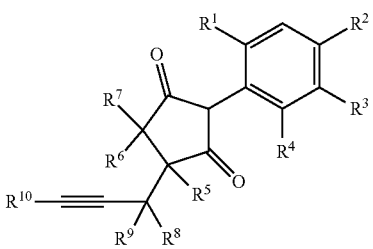

wherein R¹ is fluoro, R⁴ is 2,2,2-trifluoroethoxy, R¹⁰ is hydrogen and all of R³, R⁵, R⁶, R⁷, R⁸, and R⁹ are hydrogen, or

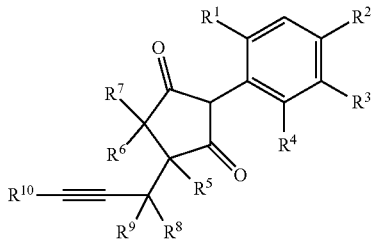

wherein R¹ is bromo, R⁴ is methoxy, R¹⁰ is hydrogen and all of R³, R⁵, R⁶, R⁷, R⁸, and R⁹ are hydrogen, or

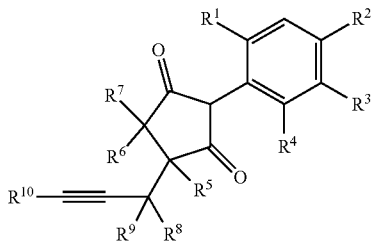

wherein R¹ is bromo, R⁴ is ethoxy, R¹⁰ is hydrogen and all of R³, R⁵, R⁶, R⁷, R⁸, and R⁹ are hydrogen, or

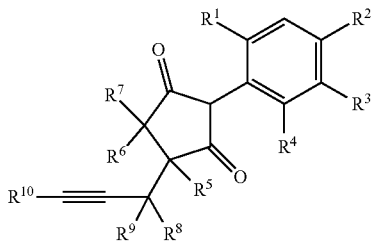

wherein R¹ is bromo, R⁴ is 2-methoxyethoxy, R¹⁰ is hydrogen and all of R³, R⁵, R⁶, R⁷, R⁸, and R⁹ are hydrogen, or

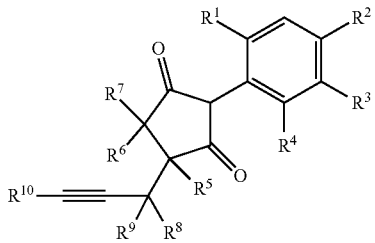

wherein R¹ is bromo, R⁴ is 2,2,2-trifluoroethoxy, R¹⁰ is hydrogen and all of R³, R⁵, R⁶, R⁷, R⁸, and R⁹ are hydrogen, or

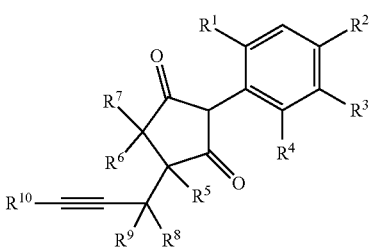

wherein R¹ is chloro, R⁴ is hydrogen, R¹⁰ is hydrogen and all of R³, R⁵, R⁶, R⁷, R⁸, and R⁹ are hydrogen, or

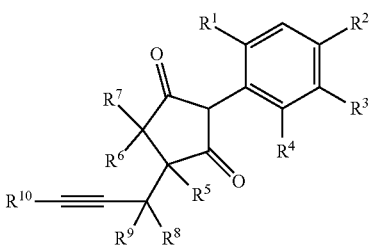

wherein R¹ is chloro, R⁴ is chloro, R¹⁰ is hydrogen and all of R³, R⁵, R⁶, R⁷, R⁸, and R⁹ are hydrogen, or

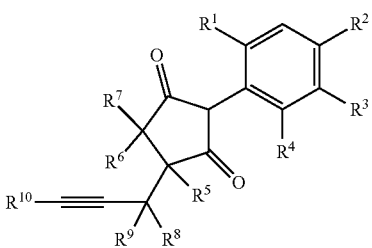

wherein R¹ is fluoro, R⁴ is hydrogen, R¹⁰ is hydrogen and all of R³, R⁵, R⁶, R⁷, R⁸, and R⁹ are hydrogen, or

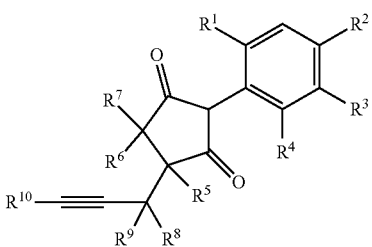

wherein R¹ is bromo, R⁴ is hydrogen, R¹⁰ is hydrogen and all of R³, R⁵, R⁶, R⁷, R⁸, and R⁹ are hydrogen, or

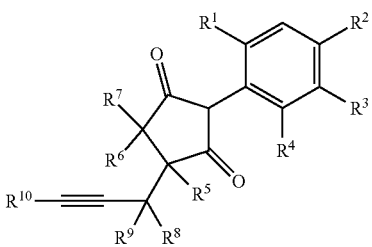

wherein R¹ is fluoro, R⁴ is fluoro, R¹⁰ is hydrogen and all of R³, R⁵, R⁶, R⁷, R⁸, and R⁹ are hydrogen, or

173

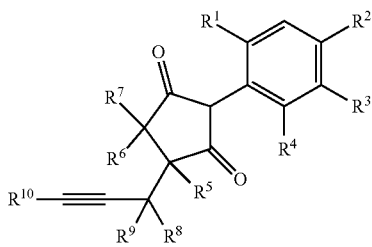

wherein $R^1$ is fluoro, $R^4$ is chloro, $R^{10}$ is hydrogen and all of $R^3$, $R^5$, $R^6$, $R^7$, $R^8$, and $R^9$ are hydrogen, or

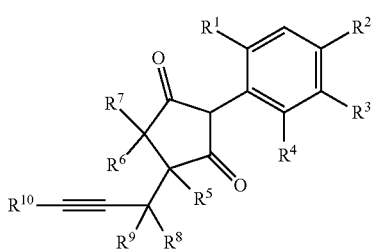

wherein $R^1$ is methyl, $R^4$ is methyl, $R^{10}$ is methyl and all of $R^3$, $R^5$, $R^6$, $R^7$, $R^8$, and $R^9$ are hydrogen, or

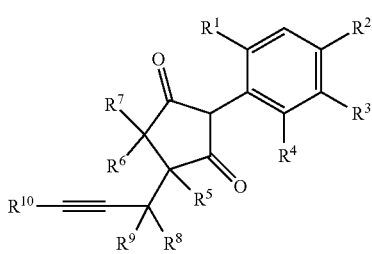

wherein $R^1$ is methyl, $R^4$ is hydrogen, $R^{10}$ is methyl and all of $R^3$, $R^5$, $R^6$, $R^7$, $R^8$, and $R^9$ are hydrogen, or

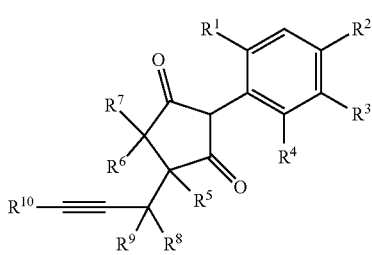

wherein $R^1$ is methyl, $R^4$ is ethyl, $R^{10}$ is methyl and all of $R^3$, $R^5$, $R^6$, $R^7$, $R^8$, and $R^9$ are hydrogen, or

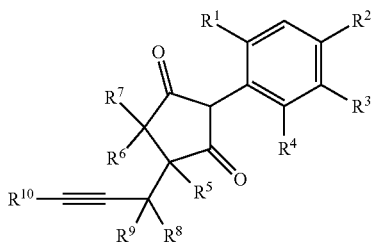

wherein $R^1$ is ethyl, $R^4$ is hydrogen, $R^{10}$ is methyl and all of $R^3$, $R^5$, $R^6$, $R^7$, $R^8$, and $R^9$ are hydrogen, or

174

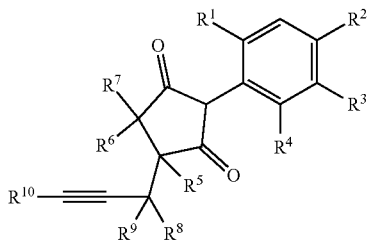

wherein $R^1$ is methyl, $R^4$ is methoxy, $R^{10}$ is methyl and all of $R^3$, $R^5$, $R^6$, $R^7$, $R^8$, and $R^9$ are hydrogen, or

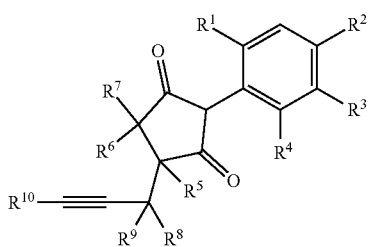

wherein $R^1$ is methyl, $R^4$ is ethoxy, $R^{10}$ is methyl and all of $R^3$, $R^5$, $R^6$, $R^7$, $R^8$, and $R^9$ are hydrogen, or

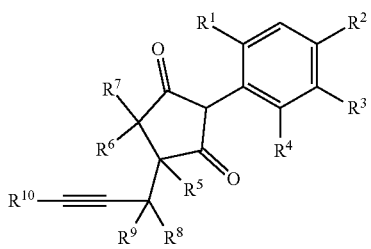

wherein $R^1$ is methyl, $R^4$ is 2-methoxyethoxy, $R^{10}$ is methyl and all of $R^3$, $R^5$, $R^6$, $R^7$, $R^8$, and $R^9$ are hydrogen, or

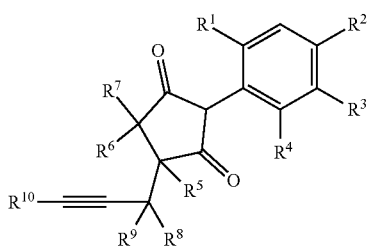

wherein $R^1$ is methyl, $R^4$ is 2,2,2-trifluoroethoxy, $R^{10}$ is methyl and all of $R^3$, $R^5$, $R^6$, $R^7$, $R^8$, and $R^9$ are hydrogen, or

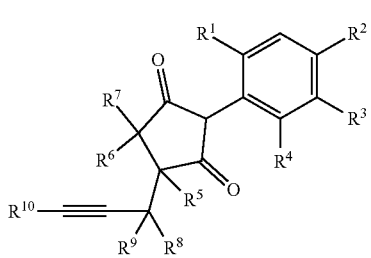

wherein $R^1$ is chloro, $R^4$ is methoxy, $R^{10}$ is methyl and all of $R^3$, $R^5$, $R^6$, $R^7$, $R^8$, and $R^9$ are hydrogen, or

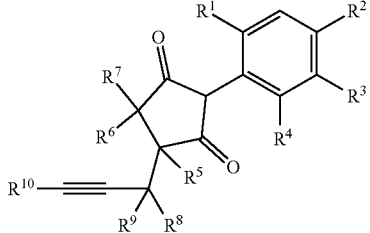

wherein $R^1$ is chloro, $R^4$ is ethoxy, $R^{10}$ is methyl and all of $R^3$, $R^5$, $R^6$, $R^7$, $R^8$, and $R^9$ are hydrogen, or

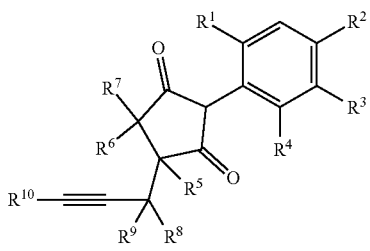

wherein $R^1$ is chloro, $R^4$ is 2-methoxyethoxy, $R^{10}$ is methyl and all of $R^3$, $R^5$, $R^6$, $R^7$, $R^8$, and $R^9$ are hydrogen, or

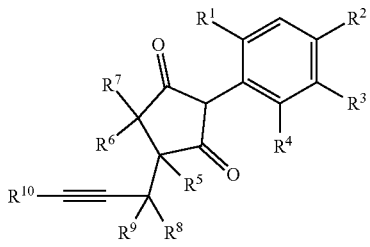

wherein $R^1$ is chloro, $R^4$ is 2,2,2-trifluoroethoxy, $R^{10}$ is methyl and all of $R^3$, $R^5$, $R^6$, $R^7$, $R^8$, and $R^9$ are hydrogen, or

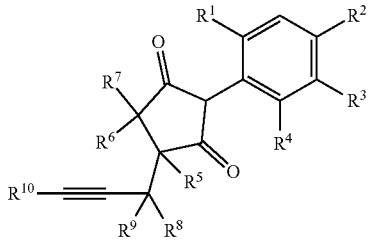

wherein $R^1$ is fluoro, $R^4$ is methoxy, $R^{10}$ is methyl and all of $R^3$, $R^5$, $R^6$, $R^7$, $R^8$, and $R^9$ are hydrogen, or

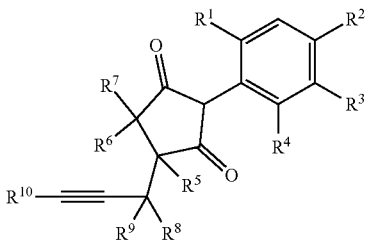

wherein $R^1$ is fluoro, $R^4$ is ethoxy, $R^{10}$ is methyl and all of $R^3$, $R^5$, $R^6$, $R^7$, $R^8$, and $R^9$ are hydrogen, or

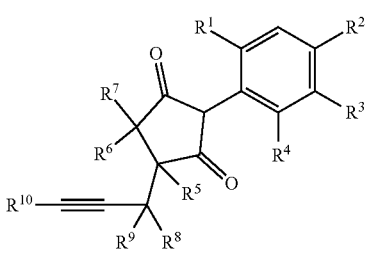

wherein $R^1$ is fluoro, $R^4$ is 2-methoxyethoxy, $R^{10}$ is methyl and all of $R^3$, $R^5$, $R^6$, $R^7$, $R^8$, and $R^9$ are hydrogen, or

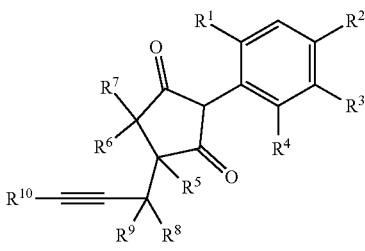

wherein $R^1$ is fluoro, $R^4$ is 2,2,2-trifluoroethoxy, $R^{10}$ is methyl and all of $R^3$, $R^5$, $R^6$, $R^7$, $R^8$, and $R^9$ are hydrogen, or

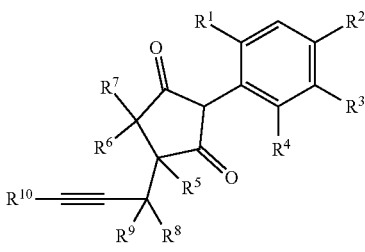

wherein $R^1$ is bromo, $R^4$ is methoxy, $R^{10}$ is methyl and all of $R^3$, $R^5$, $R^6$, $R^7$, $R^8$, and $R^9$ are hydrogen, or

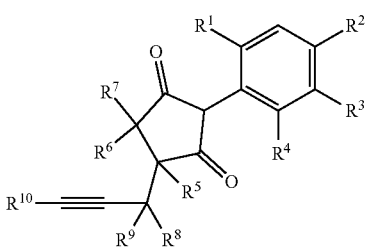

wherein $R^1$ is bromo, $R^4$ is ethoxy, $R^{10}$ is methyl and all of $R^3$, $R^5$, $R^6$, $R^7$, $R^8$, and $R^9$ are hydrogen, or

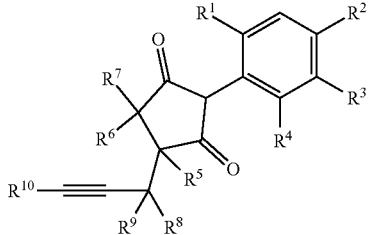

wherein $R^1$ is bromo, $R^4$ is 2-methoxyethoxy, $R^{10}$ is methyl and all of $R^3$, $R^5$, $R^6$, $R^7$, $R^8$, and $R^9$ are hydrogen, or

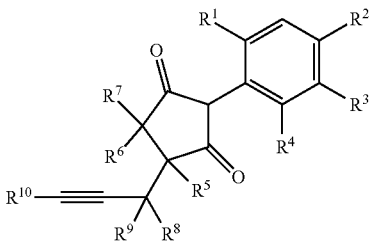

wherein $R^1$ is bromo, $R^4$ is 2,2,2-trifluoroethoxy, $R^{10}$ is methyl and all of $R^3$, $R^5$, $R^6$, $R^7$, $R^8$, and $R^9$ are hydrogen, or

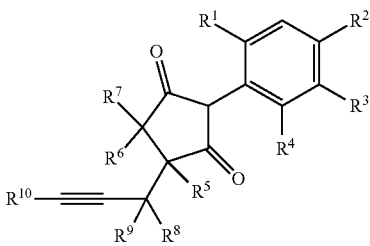

wherein $R^1$ is chloro, $R^4$ is hydrogen, $R^{10}$ is methyl and all of $R^3$, $R^5$, $R^6$, $R^7$, $R^8$, and $R^9$ are hydrogen, or

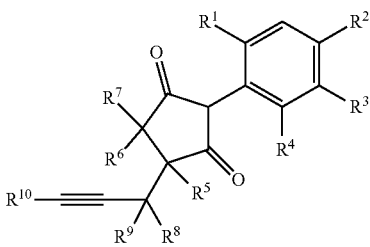

wherein $R^1$ is chloro, $R^4$ is chloro, $R^{10}$ is methyl and all of $R^3$, $R^5$, $R^6$, $R^7$, $R^8$, and $R^9$ are hydrogen, or

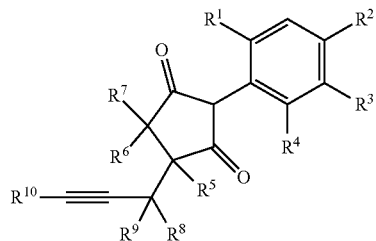

wherein $R^1$ is fluoro, $R^4$ is hydrogen, $R^{10}$ is methyl and all of $R^3$, $R^5$, $R^6$, $R^7$, $R^8$, and $R^9$ are hydrogen

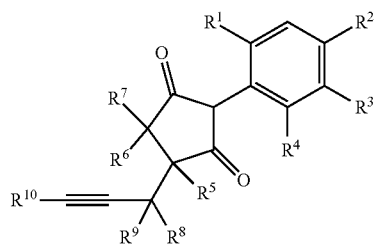

wherein $R^1$ is bromo, $R^4$ is hydrogen, $R^{10}$ is methyl and all of $R^3$, $R^5$, $R^6$, $R^7$, $R^8$, and $R^9$ are hydrogen, or

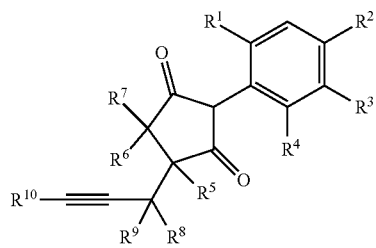

wherein $R^1$ is fluoro, $R^4$ is fluoro, $R^{10}$ is methyl and all of $R^3$, $R^5$, $R^6$, $R^7$, $R^8$, and $R^9$ are hydrogen, or

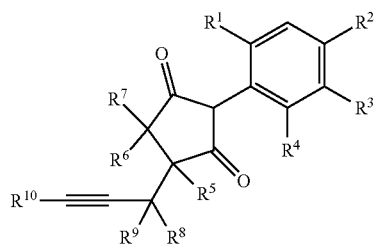

wherein $R^1$ is fluoro, $R^4$ is chloro, $R^{10}$ is methyl and all of $R^3$, $R^5$, $R^6$, $R^7$, $R^8$, and $R^9$ are hydrogen, and
$R^2$ is selected from the group consisting of:
phenyl,
3-fluorophenyl,
4-fluorophenyl,
3-chlorophenyl,
4-chlorophenyl,
3-bromophenyl,
4-bromophenyl,
4-iodophenyl,
4-methylphenyl, 4-cyanophenyl,
4-methoxyphenyl,
3-difluoromethoxyphenyl,
4-difluoromethoxyphenyl,
3-difluoromethylphenyl,
4-difluoromethylphenyl,
3-trifluoromethylphenyl,
4-trifluoromethylphenyl,
3-trifluoromethoxyphenyl,
4-trifluoromethoxyphenyl,
4-methylthiophenyl,
4-methylsulfinylphenyl,
4-methylsulfonylphenyl,
2,4-difluorophenyl,
3,4-difluorophenyl,
3,5-difluorophenyl,
2,4-dichlorophenyl,
3,4-dichlorophenyl,
4-chloro-2-fluorophenyl,
4-chloro-3-fluorophenyl,
4-chloro-2-methoxyphenyl,
4-chloro-3-methoxyphenyl,
4-chloro-2-methylphenyl,
4-chloro-3-methylphenyl,
2-fluoro-4-cyanophenyl,
2-chloropyridin-5-yl,
5-chloropyridin-2-yl,
3-fluoro-5-chloropyridin-2-yl,
5-trifluoromethylpyridin-2-yl,
3-chloro-5-trifluoromethylpyridin-2-yl,
5-fluoropyridin-2-yl,
5-bromopyridin-2-yl,
6-chloropyridazin-3-yl,
5-bromopyrimidin-2-yl,
5-chloropyrimidin-2-yl,
5-fluoropyrimidin-2-yl,
4-chlorothien-2-yl,
5-chlorothien-2-yl,
3-chloropyrazol-1-yl, and
4-chloropyrazol-1-yl; or
wherein the compound has the formula:

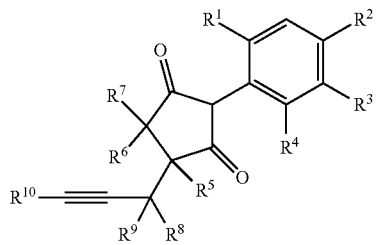

wherein $R^1$ is methyl, $R^4$ is hydrogen, $R^{10}$ is hydrogen and all of $R^2$, $R^5$, $R^6$, $R^7$, $R^8$, and $R^9$ are hydrogen, or

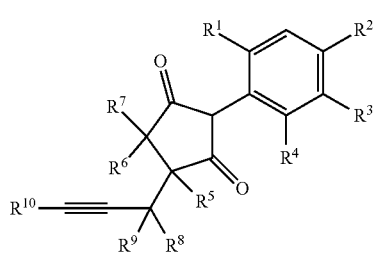

wherein $R^1$ is ethyl, $R^4$ is hydrogen, $R^{10}$ is hydrogen and all of $R^2$, $R^5$, $R^6$, $R^7$, $R^8$, and $R^9$ are hydrogen, or

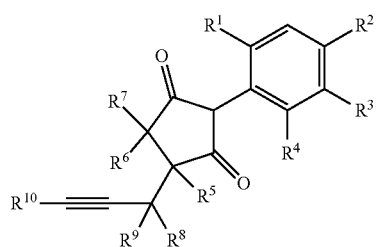

wherein $R^1$ is chloro, $R^4$ is hydrogen, $R^{10}$ is hydrogen and all of $R^2$, $R^5$, $R^6$, $R^7$, $R^8$, and $R^9$ are hydrogen, or

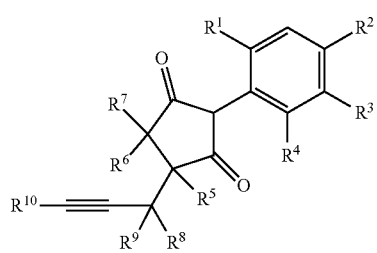

wherein $R^1$ is fluoro, $R^4$ is hydrogen, $R^{10}$ is hydrogen and all of $R^2$, $R^5$, $R^6$, $R^7$, $R^8$, and $R^9$ are hydrogen, or

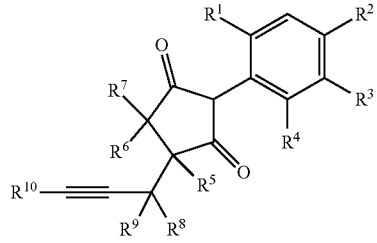

wherein $R^1$ is methyl, $R^4$ is hydrogen, $R^{10}$ is methyl and all of $R^2$, $R^5$, $R^6$, $R^7$, $R^8$, and $R^9$ are hydrogen, or

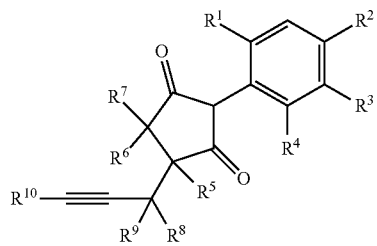

wherein $R^1$ is ethyl, $R^4$ is hydrogen, $R^{10}$ is methyl and all of $R^2$, $R^5$, $R^6$, $R^7$, $R^8$, and $R^9$ are hydrogen, or

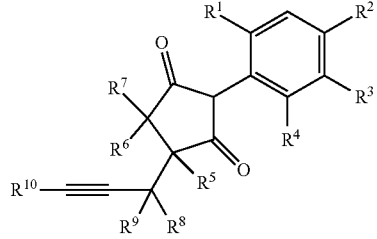

wherein $R^1$ is chloro, $R^4$ is hydrogen, $R^{10}$ is methyl and all of $R^2$, $R^5$, $R^6$, $R^7$, $R^8$, and $R^9$ are hydrogen, or

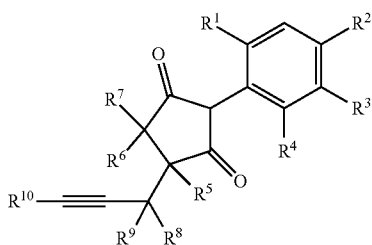

wherein R¹ is fluoro, R⁴ is hydrogen, R¹⁰ is methyl and all of R², R⁵, R⁶, R⁷, R⁸, and R⁹ are hydrogen, and R³ is selected from the group consisting of:
phenyl,
3-fluorophenyl,
4-fluorophenyl,
3-chlorophenyl,
4-chlorophenyl,
3-bromophenyl,
4-bromophenyl,
4-iodophenyl,
4-methylphenyl,
4-cyanophenyl,
4-methoxyphenyl,
3-difluoromethoxyphenyl,
4-difluoromethoxyphenyl,
3-difluoromethylphenyl,
4-difluoromethylphenyl,
3-trifluoromethylphenyl,
4-trifluoromethylphenyl,
3-trifluoromethoxyphenyl,
4-trifluoromethoxyphenyl,
4-methylthiophenyl,
4-methylsulfinylphenyl,
4-methylsulfonylphenyl,
2,4-difluorophenyl,
3,4-difluorophenyl,
3,5-difluorophenyl,
2,4-dichlorophenyl,
3,4-dichlorophenyl,
4-chloro-2-fluorophenyl,
4-chloro-3-fluorophenyl,
4-chloro-2-methoxyphenyl,
4-chloro-3-methoxyphenyl,
4-chloro-2-methylphenyl,
4-chloro-3-methylphenyl,
2-fluoro-4-cyanophenyl,
2-chloropyridin-5-yl,
5-chloropyridin-2-yl,
3-fluoro-5-chloropyridin-2-yl,
5-trifluoromethylpyridin-2-yl,
3-chloro-5-trifluoromethylpyridin-2-yl,
5-fluoropyridin-2-yl,
5-bromopyridin-2-yl,
6-chloropyridazin-3-yl,
5-bromopyrimidin-2-yl,
5-chloropyrimidin-2-yl,
5-fluoropyrimidin-2-yl,
4-chlorothien-2-yl,
5-chlorothien-2-yl,
3-chloropyrazol-1-yl,
4-chloropyrazol-1-yl; and
may be present either as a free compound and/or present as an agrochemically acceptable salt thereof.

21. A herbicidal composition which comprises:
   (i) a compound of formula (I), as defined in claim 1, and
   (ii) an agrochemically acceptable carrier, diluent and/or solvent;
   (iii) optionally one or more further herbicides; and
   (iv) optionally a safener.

22. A method of controlling grassy monocotyledonous weeds in crops of useful plants, comprising applying a compound of formula (I), as defined in claim 1, or a herbicidal composition comprising such a compound, to the weeds, to the plants, or to the locus thereof.

23. The method as claimed in claim 22, wherein the crops of useful plants comprise wheat, barley, rye, triticale, sugarcane, soybean, peanut, pulse crops, cotton, rape, sunflower, linseed, sugarbeet, fodder beet, potato, and/or dicotyledonous vegetables.

24. A compound of formula (II):

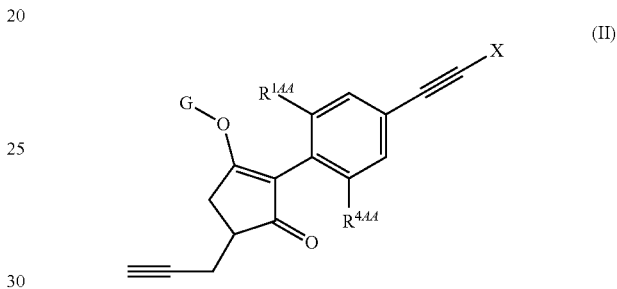

wherein:
X is methyl or chlorine;
$R^{1AA}$ is methoxy, ethoxy, $C_1$fluoroalkoxy, ethyl, n-propyl, cyclopropyl or ethynyl;
$R^{4AA}$ is hydrogen, methoxy, ethoxy, $C_1$fluoroalkoxy or ethyl; and
G is hydrogen, an agriculturally acceptable metal, or an agriculturally acceptable sulfonium or ammonium group; or G is —C(O)—$R^{AA}$ or —C(O)—$X^{CC}$—$R^{BB}$; wherein $X^{CC}$ is oxygen or sulfur;
$R^{AA}$ is $C_1$-$C_{10}$alkyl, $C_2$-$C_6$alkenyl, $C_2$-$C_6$alkynyl, $C_3$-$C_6$cycloalkyl, $C_3$-$C_6$cycloalkyl-methyl-, $C_1$-$C_3$alkoxy$C_1$-$C_3$alkyl; phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or phenyl-methyl- in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; and
$R^{BB}$ is $C_1$-$C_{10}$alkyl, $C_2$-$C_5$alkenyl-$CH_2$—, $C_2$-$C_4$alkenyl-CH(Me)-, $C_2$-$C_5$alkynyl-$CH_2$—, $C_2$-$C_4$alkynyl-CH(Me)-, $C_3$-$C_6$cycloalkyl, $C_3$-$C_6$cycloalkyl-methyl-, $C_1$-$C_3$alkoxy$C_1$-$C_3$alkyl; phenyl or phenyl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; monocyclic heteroaryl or monocyclic heteroaryl substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano; or phenyl-methyl- in which the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine or cyano;

and wherein the compound of formula (II) is optionally present as an agrochemically acceptable salt thereof.

25. The compound as claimed in claim 24, wherein
X is methyl;
$R^{1AA}$ is methoxy, ethyl or n-propyl;
$R^{4AA}$ is hydrogen, methoxy or ethyl; and
G is hydrogen, an agriculturally acceptable metal, or an agriculturally acceptable sulfonium or ammonium group.

\* \* \* \* \*